United States Patent
Daniels

(10) Patent No.: US 11,732,040 B2
(45) Date of Patent: Aug. 22, 2023

(54) ANTI-CD33 AND ANTI-CD7 COMBINATION TREATMENT

(71) Applicant: BiVictriX Limited, Macclesfield (GB)

(72) Inventor: Tiffany Jane Daniels, Cheshire (GB)

(73) Assignee: BIVICTRIX LIMITED, Macclesfield (GB)

( * ) Notice: Subject to any disclaimer, the term of this patent is extended or adjusted under 35 U.S.C. 154(b) by 35 days.

(21) Appl. No.: 16/767,470

(22) PCT Filed: Nov. 27, 2018

(86) PCT No.: PCT/GB2018/053429
§ 371 (c)(1),
(2) Date: May 27, 2020

(87) PCT Pub. No.: WO2019/102234
PCT Pub. Date: May 31, 2019

(65) Prior Publication Data
US 2021/0139580 A1    May 13, 2021

(30) Foreign Application Priority Data
Nov. 27, 2017  (GB) ..................... 1719646

(51) Int. Cl.
*C07K 16/28* (2006.01)
*A61K 35/17* (2015.01)
*A61K 39/00* (2006.01)

(52) U.S. Cl.
CPC .......... *C07K 16/2803* (2013.01); *A61K 35/17* (2013.01); *A61K 2039/505* (2013.01); *C07K 2317/31* (2013.01); *C07K 2317/732* (2013.01); *C07K 2317/77* (2013.01); *C07K 2319/55* (2013.01)

(58) Field of Classification Search
CPC ........ C07K 16/00–468; C07K 14/7051; C07K 2317/31
See application file for complete search history.

(56) References Cited

U.S. PATENT DOCUMENTS

| | | | |
|---|---|---|---|
| 4,978,744 A | 12/1990 | Pettit et al. | |
| 5,202,238 A | 4/1993 | Fell, Jr. et al. | |
| 5,204,244 A | 4/1993 | Fell et al. | |
| 5,635,483 A | 6/1997 | Pettit et al. | |
| 5,780,588 A | 6/1998 | Pettit et al. | |
| 2010/0291112 A1* | 11/2010 | Kellner | A61P 35/00 435/69.6 |

FOREIGN PATENT DOCUMENTS

| | | | |
|---|---|---|---|
| CN | 107109419 A | 8/2017 | |
| JP | 2016514457 A | 5/2016 | |
| JP | 2017522880 A | 8/2017 | |
| WO | WO 03/011161 A1 | 2/2003 | |
| WO | WO-2013104804 A2 * | 7/2013 | .............. A61P 1/04 |
| WO | WO-2016014576 A1 * | 1/2016 | ........... A61K 31/436 |
| WO | WO-2017213979 A1 * | 12/2017 | ............. A61K 35/15 |
| WO | WO-2018045325 A1 * | 3/2018 | ............. A61K 35/17 |
| WO | 2019102234 A1 | 5/2019 | |
| WO | 2020102589 A1 | 5/2020 | |
| WO | 2020142659 A2 | 7/2020 | |

OTHER PUBLICATIONS

Peipp et al., Cancer Res 62:2848-2855 (Year: 2002).*
Schwemmlein et al., Br. J Haematol 133:141-151 (Year: 2006).*
Brinkmann & Kontermann, MABS 9:182-212 (Year: 2017).*
Vazquez-Lombardi et al., Drug Discovery Today 20(10): 1271-83 (Year: 2015).*
Gleason et al., Blood 123(19):3016-26 (Year: 2014).*
Hoseini & Cheung, Blood Cancer J., 7,e522; doi: 10.1038/bcj.2017.2 (Year: 2017).*
Tang et al., Oncotarget 7(23): 34070-83 (Year: 2016).*
Gross & Eshhar, Annu. Rev. Pharmacol. Toxicol. 56:59-83 (Year: 2016).*
Kenderian et al., Leukemia 29:1637-47 (Year: 2015).*
Wang et al., Mol Therapy 23: 184-191 (Year: 2015).*
Gomes-Silva et al., Blood 130(d):285-296 (Year: 2017).*
Schneider et al., J Immunother Cancer, 5:42; DOI 10.1186/S40425-017-0246-1 (Year: 2017).*
Ossenkoppele et al., Br. J. Haematol. 153:421-36 (Year: 2011).*
Blum et al., Leukemia Res; 60:63-73 (Year: 2017).*
M. Cianfriglia, Ann lst Super Sanitia 49(2):150-168 (Year: 2013).*
Andreev et al. Mol Cancer Ther; 16(4):681-93 (Year: 2017).*
Alley et al., "Antibody-drug conjugates: targeted drug delivery for cancer." Curr. Opin. Chem. Biol., vol. 14, pp. 529-537 (2010).
Asou et al., "Establishment of an Undifferentiated Leukemia Cell Line (Kasumi-3) with t(3;7)(q27;q22) and Activation of the EVI1 Gene." Jpn. J. Cancer Res., vol. 87, pp. 269-274 (1996).
Barcena et al., "Tracing the Expression of CD7 and other Antigens during T- and Myeloid-cell Differentiation in the Human Fetal Liver and Thymus." Leukemia and Lymphoma, vol. 17, pp. 1-11 (1994).
Bhatnagar et al., "Marine Antitumor Drugs: Status, Shortfalls and Strategies." Mar. Drugs, vol. 8, pp. 2702-2720 (2010).
Bird et al., "Single-chain antigen-binding proteins." Science, vol. 242:423-426 (1988).
Boerner et al., "Production of antigen-specific human monoclonal antibodies from in vitro-primed human splenocytes." J. Immunol., vol. 147, pp. 86-95 (1991).
Boger, "Design, synthesis, and evaluation of DNA minor groove binding agents: the duocarmycins." Pure & Appl. Chem., vol. 66(4), pp. 837-844 (1994).

(Continued)

*Primary Examiner* — Jessica H Roark
(74) *Attorney, Agent, or Firm* — KDW Firm PLLC

(57) ABSTRACT

This invention relates to the dual targeting of cell inhibiting agents to the cell surface receptors CD7 and CD33 in the treatment of hematological malignancy. In particular, the invention relates to cell inhibiting agents that bispecifically binds to CD33 and CD7 for use in the treatment of a CD7+CD33+ hematological malignancy. Such agents may comprise bispecific antibody drug conjugates.

9 Claims, 18 Drawing Sheets

(56) References Cited

OTHER PUBLICATIONS

Bremner, "Traumatic stress: effects on the brain." Dial. Clin. Neurosci., vol. 8(4), pp. 445-461 (2006).
Carter et al., "Antibody-Drug Conjugates for Cancer Therapy," Cancer J., vol. 14(3), pp. 154-169 (2008).
Chang, "Prognostic relevance of immunophenotyping in 379 patients with acute myeloid leukemia." Leukemia Research, vol. 28, pp. 43-48 (2004).
Chen et al., "Immunophenotypic Features of Myeloid Stem Cell Neoplasms Associated with Monosomy 7." Blood, vol. 124, p. 1051 (2014).
Clynes et al., "Inhibitory Fc receptors modulate in vivo cytoxicity against tumor targets." Nat. Med., vol. 6(4), pp. 443-446 (2000).
Cotta et al., "Diagnosis of Mycosis Fungoides: A Comparative Immunohistochemical Study of T-Cell Markers Using a Novel Anti-CD7 Antibody." Appl. Immunohistochem. Mol. Morphol., vol. 14, pp. 291-295 (2006).
De Kouchkovsky et al., "Acute myeloid leukemia: a comprehensive review and 2016 update." Blood Cancer Journal, vol. 6, pp. 1-10 (2016).
De Propris et al., "High CD33 expression levels in acute myeloid leukemia cells carrying the nucleophosmin (NPM1) mutation." Haemotological, vol. 96, pp. 1548-1551 (2011).
Del Poeta et al., "CD7 Expression in Acute Myeloid Leukemia." Leuk. Lymphoma, vol. 17, pp. 111-119 (1995).
Drake et al., "Biacore surface matrix effects on the binding kinetics and affinity of antigen/antibody complex." Analy. Biochem., vol. 429, pp. 58-69 (2012).
Dubowchik et al., "Receptor-mediated and enzyme-dependent targeting of cytotoxic anticancer drugs." Pharm. Therapeutics, vol. 83, pp. 67-123 (1999).
Ehninger et al., "Distribution and levels of cell surface expression of CD33 and CD123 in acute myeloid leukemia." Blood Cancer Journal, vol. 4, pp. 1-10 (2014).
Estey, "Therapeutic Options for Acute Myelogenous Leukemia." Cancer, vol. 92(5), pp. 1059-1073 (2001).
Eto et al., "Biological characteristics of CD7 positive acute myelogeneous leukemia." British Journal of Haematology, vol. 82, pp. 508-514 (1992).
Frankel et al., "Therapy of Patients with T-cell Lymphomas and Leukemias Using an Anti-CD7 Monoclonal Antibody-Rich a Chain Immunotoxin." Leuk. & Lymph., vol. 26(3-4), pp. 287-298 (1997).
GB Search Report corresponding to Application No. GB 1719646.0 dated Aug. 22, 2018.
Hao, "Electrorheological Fluids." Adv. Mater., vol. 13(24), pp. 1847-1857 (2001).
Heinrich et al., "Comparison of the results obtained by ELISA and surface plasmon resonance for the determination of antibody affinity." J. Immunol. Meth., vol. 352, pp. 13-22 (2010).
Hoogenboom et al., "By-passing immunisation: Human antibodies from synthetic repertoires of germline VH gene segments rearranged in vitro." J. Mol. Biol., vol. 227, pp. 381-388 (1992).
Huston et al., "Protein engineering of antibody binding sites: recovery of specific activity in an anti-digoxin single-chain Fv analogue produced in *Escherichia coli*." Proc. Natl. Acad. Sci. USA, vol. 85, pp. 5879-5883 (1988).
Huston, "Protein engineering of single-chain Fv analogs and fusion proteins," Methods in Enzymol., vol. 203, pp. 46-88 (1991).
International Preliminary Report on Patentability Corresponding to International application No. PCT/GB 2018/053429 dated Jun. 2, 2020.
International Search Report and Written Opinion of the International Searching Authority Corresponding to International application No. PCT/GB 2018/053429 dated Feb. 18, 2019.
Jakobovits et al., "Analysis of homozygous mutant chimeric mice: deletion of the immunoglobulin heavy-chain joining region blocks B-cell development and antibody production." Proc. Natl. Acad. Sci. USA, vol. 90, pp. 2551-2555 (1993).
Jakobovits et al., "Germ-line transmission and expression of a human-derived yeast artificial chromosome." Nature, vol. 362, pp. 255-258 (1993).
Johnsson et al., "Immobilization of proteins to a carboxymethyldextran-modified gold surface for biospecific interaction analysis in surface plasmon resonance sensors," Analytical Biochemistry, vol. 198, pp. 268-277 (1991).
Johnson et al., "Anti-tumor activity of CC49-doxorubicin immunoconjugates," Anticancer Res., vol. 15, pp. 1387-1393 (1995)[Abstract].
Johnsson et al., "Comparison of methods for immobilization to carboxymethyl dextran sensor surfaces by analysis of the specific activity of monoclonal antibodies." J. Mol. Recognit., vol. 8, pp. 125-131 (1995).
Jonsson et al., "Introducing a biosensor based technology for real-time biospecific interaction analysis," Ann. Biol. Clin., vol. 51, pp. 19-26 (1993)[Abstract].
Jonsson et al., "Real-time biospecific interaction analysis using surface plasmon resonance and a sensor chip technology." Biotechniques, vol. 11, pp. 620-627 (1991).
Kahl et al., "CD7+ and CD56+ Acute Myelogenous Leukemia is a Distinct Biologic and Clinical Disease Entity." Haematology and Blood Transfusion, vol. 40, pp. 112-119 (2001).
Khalil et al., "The future of cancer treatment: immunomodulation, CARs and combination immunotherapy." Nature Reviews; Clinical Oncology, vol. 13, pp. 273-290 (2016).
Khaw et al., "Technetium-99m Labeling of Antibodies to Cardiac Myosin Fab." J. Nucl. Med., vol. 23, pp. 1011-1019 (1982).
Kita et al., "Clinical Importance of CD7 Expression in Acute Myelocytic Leukemia." Blood, vol. 81, pp. 2399-2405 (1993).
Klein et al., "Chronic pain as a manifestation of potassium channel-complex autoimmunity." Neurology, vol. 79, pp. 1136-1144 (2012).
Kouchkovsky et al., "Acute myeloid leukemia: a comprehensive review and 2016 update." Blood Cancer J., vol. 6, Article ID e441 (10 pages) (2016).
Lau et al., "Conjugation of doxorubicin to monoclonal anti-carcinoembryonic antigen antibody via novel thiol-directed cross-linking reagents." Bioorg-Med-Chem., vol. 3, pp. 1299-1304 (1995).
Lau et al., "Novel Doxorubicin-Monoclonal Anti-carcinoembryonic Antigen Antibody Immunoconjugate Activity in vitro." Bioog-Med-Chem, vol. 3, pp. 1305-1312 (1995).
Lazarovits et al., "Expression and function of the MAdCAM-1 receptor, integrin alpha 4 beta 7, on human leukocytes." J. Immunol., vol. 153, pp. 517-528 (1994).
Lefranc, "Nomenclature of the Human Immunoglobulin Genes." Curr. Protocol. Immunol., A.1p. 1-A.1 p. 37 (2000).
Lo Coco et al., "CD7 positive acute myeloid leukaemia: a subtype associated with cell immaturity." British Journal of Haematology, vol. 73, 480-485 (1989).
Lobach et al., "Human T cell antigen expression during the early stages of fetal thymic maturation." J. Immunol., vol. 135, pp. 1752-1759 (1985).
Marks et al., "By-passing immunization: Human antibodies from V-gene libraries displayed on phage." J. Mol. Biol., vol. 222, pp. 581-597 (1991).
Maus et al., "Antibody-modified T cells: CARs take the front seat for Hematologic malignancies." Blood, vol. 123(17), pp. 2625-2635 (2014).
Morrison et al., "Chimeric human antibody molecules: Mouse antigen-binding domains with human constant region domains." Proc. Natl. Acad. Sci. USA, vol. 81, pp. 6851-6855 (1984).
Neuberger et al., "A hapten-specific chimaeric IgE antibody with human physiological effector function." Nature, vol. 314, pp. 268-270 (1985).
Peipp et al., "A Recombinant CD7-specific Single-Chain Immunotoxin Is a Potent Inducer of Apoptosis in Acute Leukemic T Cells." Cancer Res., vol. 62, pp. 2848-2855 (2002).
Pivot et al., "Novel Cytotoxic Agents in Chemotherapy-resistant Metastatic Breast Cancer—The Epothilones," European Oncology, vol. 4(2), pp. 42-45 (2008).
Presta, "Engineering of therapeutic antibodies to minimize immunogenicity and optimize function." Adv. Drug Deliv. Rev., vol. 58, pp. 640-656 (2006).

(56) References Cited

OTHER PUBLICATIONS

Rausei-Mills et al., "Aberrant Expression of CD7 in Myeloblasts Is Highly Associated With De Novo Acute Myeloid Leukemias With FLT3/ITD Mutation." Am. J. Clin. Pathol., vol. 129, pp. 624-629 (2008).
Reading et al., "Expression of unusual immunophenotype combinations in acute myelogenous leukemia." Blood, vol. 81, pp. 3083-3090 (1993).
Riechmann et al., "Reshaping human antibodies for therapy." Nature, vol. 332, pp. 323-327 (1988).
Rohrs et al., "CD7 in acute myeloid leukemia: correlation with loss of wild-type CEBPA, consequence of epigenetic regulation." Journal of Hematology & Oncology, vol. 3(15) (2010).
Rousseaux et al., "Optimal conditions for the preparation of proteolytic fragments from monoclonal IgG of different rat IgG subclasses." Methods Enzymology, vol. 121, pp. 663-669, Academic Press, (1986).
Sempowski et al., "Structure and Function of the CD7 Molecule." Crit. Rev. Immunol., vol. 19, pp. 331-348 (1999).
Shimamoto et al., "Clinical and Biological Characteristic of CD7+ Acute Myeloid Leukaemia." Cancer Genet Cyrogenet, vol. 73, pp. 69-74 (1994).
Simmons et al., "Marine natural products as anticancer drugs." Mol. Cancer Ther., vol. 4(2), pp. 333-342 (2004).
Smith et al., "The Enediyne Antibiotics," J. Med. Chem., vol. 39(11), pp. 2103-2117 (1996).
Stasi et al., "Analysis of Treatment Failure in Patients with Minimally Differentiated Acute Myeloid Leukemia (AML-M0)." Blood, vol. 83(6), pp. 1619-1625 (1994).
Stillwell et al., "Sustaining Evidence-Based Practice Through Organizational Policies and an Innovative Model." Amer. J. Nursing, vol. 111 (9), pp. 57-60 (2011).
Tien et al., "CD7 Positive Hematopoietic Progenitors and Acute Myeloid Leukemia and other Minimally Differentiated Leukemia." Leukemia and Lymphoma, vol. 3, pp. 93-98 (1998).
Vallera et al., "Laboratory preparation of a deglycosylated ricin toxin a chain containing immunotoxin directed against a CD7 T lineage differentiation antigen for phase I human clinical studies involving T cell malignancies." J. Immunol. Methods, vol. 197, pp. 69-83 (1996).
Van Dijk et al., "Human antibodies as next generation therapeutics." Curr. Opin. Chem. Biol., vol. 5, pp. 368-374 (2001).
Waurzyniak et al., "Pharmacokinetic Features, Immunogenicity, and Toxicity of B43(anti-CD19)-Pokeweed Antiviral Protein Immunotoxin in Cynomolgus Monkeys." Clin. Cancer Res., vol. 3, pp. 325-337 (1997).
Weiner, "Monoclonal antibody mechanisms of action in cancer." Immunol. Res., vol. 39, pp. 271-278 (2007).
Weng et al., "Two immunoglobulin G fragment C receptor polymorphisms independently predict response to rituximab in patients with follicular lymphoma." J. Clin. Oncol., vol. 21(21), pp. 3940-3947 (2003).
OssenKoppele, Gert J. et al, "Review of the relevance of aberrant antigen expression by flow cytometry in myeloaid neoplasms," British Journal of Haematology, vol. 153, No. 4, pp. 421-436, Mar. 9, 2011.
Diogo Gomes-Silvia et al., "CD7-edited T cells expressing a CD7-specific CAR for the therapy of T-cell malignancies," Blood, vol. 130, No. 3, May 24, 2017.

Walter, Roland B, et al, "ITIM-dependant endocytosis of CD33-related Siglecs: role of intracellular domain, tyrosine phosphorylation, and the tyrosine phosphatases, Shp1 and Shp2," Journal of Leukocyte Biology, vol. 83, No. 1, pp. 200-211, Oct. 18, 2007.
Yuan Yu, et al, "Humanized CD7 nanobody-based immunotoxins exhibit promising anti-T-cell acute lymphoblastic leukemia potential," International Journal of Nanomedicine, vol. 12, pp. 1969-1983, Mar. 13, 2017.
Chinese Office Action for Application No. 2018800878667 dated Mar. 24, 2023.
D'Arena et al. "Predictive Parameters for Mobilized Peripheral Blood CD34+ Progenitor Cell Collection in Patients With Hematological Malignancies," American Journal of Hematology 58, pp. 255-262 (1998).
Mizutani et al., "Cellular characteristics of acute leukemia cells simultaneously expressing CD13/CD33, CD7 and CD19," International Journal of Hematology, 66, pp. 479-491 (1997).
Office Action corresponding to Japanese Patent Application No. 2020-545898 dated Dec. 6, 2022.
Saxena et al., "Biologic and Clinical Significance of CD7 Expression in Acute Myeloid Leukemia," American Journal of Hematology, 58, pp. 278-284 (1998).
Shalabi et al. "Preclinical Development of a T-Cell ALL CAR Demonstrates That Differences in CAR Membrane Distribution May Impact Efficacy," Abstract, Blood, 128(22), 4019 (2016): https://doi.org/10.1182/blood.V128.22.4019.4019.
Japanese Office Action for Application No. 2020545898 dated Mar. 28, 2023.
International Search Report for Application No. PCT/GB2021/053432 dated Mar. 18, 2022.
International Search Report for Application No. PCT/GB2021/053433 dated Mar. 21, 2022.
Bethell, Richard et al, "Bispecific antibody drug conjugates targeting CD7 and CD33 for the treatment of actue myeloid leukemia," Cancer Research, Aug. 15, 2020.
Khaw, BA "Diagnosis of Acute Myocarditis with Radiolabeled Monoclonal Antimyosin Antibody: Immunoscintigraphic Evaluationn," Cardiac Unit Massachusetts General Hosptial Boston, 1982.
Levine, MN et al, "Randomized trial of intensive cyclophosphamdide, epirubicin, and flucrouracll chemotherapy compared with cyclophosphamide, methotrexate, and fluorouracil in premenopausal womanwith node-positive breastcancer," National Cancer Instituteof Canada Clinical Trials Group, Journal of Clinical Oncology, 1998.
International ImMunoGeneTics Information System dated acquired Jun. 6, 2023.
Octet & Biacore services-Precision Antibody date acquired Jun. 6, 2023.
Lau, Achilles et al, "Novel doxorubincin-monodonal anti-carcinoembryonic antigen antibodyimmunoconjugate activity in vitro," Bioorganic & Medicinal Chemistry, vol. 3, Issue 10, Oct. 1995.
Lau, Achilles et al, "Conjugation of doxorbuicin to monoclonal anti-carcinoembryonic antigen antibody via novel thiol-directed cross-linking reagents," Bioorganic & Medicinal Chemistry, vol. 3, Issue 10, Oct. 1995.

* cited by examiner

Cell Kill Assay: Kasumi-3 Treated with WT BiFab + aHFab-

Cell Kill Assay: Kasumi-3 Treated with BiFab-

A

B

C

A

B

C

A

B

ANTI-CD33 AND ANTI-CD7 COMBINATION TREATMENT

This invention relates to the dual targeting of cell inhibiting agents to the cell surface receptors CD7 and CD33 in the treatment of hematological malignancy.

BACKGROUND

Acute Myelogenous Leukaemia or Acute Myeloid Leukaemia (AML) is a heterogeneous haematological malignancy involving the clonal expansion of myeloid blasts in the bone marrow and peripheral blood. AML represents >90% of cases of adult acute leukaemia and remains a largely aggressive disease with a fulminant clinical course. Despite advances in therapeutic regimens and the current understanding of successful Haematopoietic Stem Cell Transplantation (HSCT), the mortality rate for patients with AML is still high. Of all adults diagnosed with AML, on average only a quarter will live for 5 years or more. In people aged over 65 years, the outlook reduces further to a mere 12% surviving for more than 5 years (www.cancerresearchuk.org). This is substantially lower than many other high incidence cancers which have received much greater investment over the last few decades, such as Breast, Prostate and Bowel Cancer, where 5-year survival is now 87%, 85%, 59%, respectively (www.cancerresearchuk.org). This highlights the degree of unmet need in AML and the urgent drive for more investment into novel therapeutics.

Current guidelines recommend that intensive treatment of AML be comprised of induction chemotherapy (including an anthracycline in combination with cytarabine) followed by consolidation therapy once patients have reached clinical and haematological remission. The mainstay of induction therapy consists of the '7+3' or similar '10+3' regimen, which combines 7 or 10 days of continuous infusion cytarabine with 3 days of an anthracycline. It is generally offered to patients with an intermediate to favourable prognosis and a low risk of treatment related mortality. Unfortunately, minimal residual disease often persists in Complete Remission (CR), and relapse is almost inevitable if treatment is discontinued. Therefore, any patient with a favourable response to induction therapy should either receive a second induction regimen or go on to receive consolidation therapy to achieve lasting remission.

Anthracyclines and cytarabine belong to the antimetabolite class of potent cytotoxic drugs and are commonly used in chemotherapy regimens as they target cells with a high Proliferative Index (PI) by inhibiting DNA replication. Debilitating side effects are a common occurrence with these agents as they are not sufficiently selective for malignant cells and therefore exhibit substantial damage to healthy tissues which also carry a high PI. Common side effects include bone marrow suppression associated with a high risk of life-threatening infections, nausea and vomiting, hair loss, bruising and bleeding complications and tumour lysis syndrome (www.macmillan.org.uk). The degree of toxicity associated with these drugs requires hospitalisation within infection control wards in specialised regional hospitals. Patients must remain hospitalised for on average 4-5 weeks until the bone marrow has fully recovered following one cycle of treatment. Many, even younger patients, do not survive the first course of intensive therapy.

Allogenic HSCT, whilst currently the only option for a cure in this disease setting, is still considered a last resort for many disease indications due to the high risk of mortality and morbidity associated with this treatment, often with treatment-related mortality rates as high as 40%. This treatment option is reliant on a suitable donor being available, and of those that do find a donor and survive the procedure, 30-45% of these patients will go on to relapse, many requiring additional transplants.

Treatment options in the elderly patient population of >60 years are minimal with the optimal approach not yet established. Elderly patients with adverse cytogenetics are less likely to respond to chemotherapy and are often more susceptible to treatment-related toxicities. Hypomethylating agents, such as azacitidine, originally used to treat Myelodysplastic Syndrome (MDS), has recently shown some benefit in elderly patients, including bridging them to induction chemotherapy to achieve CR (De Kouchkovsky, & Abdul-Hay, M. (2016) 'Acute myeloid leukemia: a comprehensive review and 2016 update'. *Blood Cancer Journal*, 6 1-10).

AML represents a problematic disease to treat as many of the proposed tumour antigens available for targeted therapies are non-specific for the malignant cell population. Conventional therapeutic approaches indicated in AML aim to target a single antigen expressed on the surface of the leukaemic blasts. Whilst these therapeutics are deemed 'targeted therapies', the antigens that they target are also expressed at high levels on a range of healthy heamatopoietic cells, required for a healthy immune system. This degree of on-target off-tissue toxicity on healthy cells demonstrated by these therapies, substantially limits their utility in the disease setting. This often results in clinicians having no option but to administer suboptimal doses to patients and a substantial number of patients dying as a result of the therapy alone.

CD33 is an AML antigen that has been extensively investigated in this setting and is a well-established and validated AML target, which is still the antigen of choice for many existing and novel therapeutics. Additionally, CD33 has also been shown to be a validated ADC target antigen, displaying a sufficient antigen density and internalisation. This is evident through the marketed ADC therapeutic Mylotarg, launched in 2000, this ADC targets the CD33 antigen in AML.

Whilst CD33 is a preferred target for many drug developers in AML due to the wide expression of this antigen on AML cells and the perceived reduced expression on earlier CD34+ haematopoietic stem cells, the CD33 antigen is also a prevalent myeloid marker in healthy cell populations. Therefore, as expected with any CD33 targeting treatment, therapies targeting this antigen also have many off-target effects on healthy cell populations, causing significant depletion of any myeloid cell harbouring the antigen. These cells are a requirement for a healthy immune system and thus depletion renders the patient in need of hospitalisation in a specialised infection controlled room, with high susceptibility to life-threatening infections. In line with this, Seattle Genetics, a prominent ADC pharma company, announced in June 2017 that they had halted all trials involving their clinical candidate SGN-CD33A, an ADC targeting CD33, after seeing a higher rate of patient deaths—including fatal infections compared to placebo in a phase III trial (fiercebiotech.com).

CD7 is an antigen commonly associated with thymocytes and mature T cells and is believed to play an essential role in T cell interactions and T/B cell interactions in early lymphoid development. This antigen does not currently represent a commonly targeted antigen in therapeutic development, assumed to be due to the extensive expression of this antigen on healthy T cell populations.

Since the late 1980s, it has been evident that certain AML cell populations express CD7, an otherwise lymphoid restricted antigen, in this disease specific manner. Expression of this antigen in AML has been reported by several groups and is suggested to be found on between 10-38% of AML cases (Poeta, G. D., et al. (1995) CD7 Expression in Acute Myeloid Leukemia. *Leuk. Lymphoma*, 17, 111-119; Rohrs, S., et al. (2010) CD7 in acute myeloid leukemia: correlation with loss of wild-type CEBPA, consequence of epigenetic regulation, *Journal of Hematology & Oncology*, 3 1-7; Rausei-M ills, V., et al. (2008) Aberrant Expression of CD7 in Myeloblasts Is Highly Associated With De Novo Acute Myeloid Leukemias With FLT3/ITD Mutation, *Am J Clin Pathol*, 129 624-629; Shimamoto, T., et al. (1994) Clinical and Biological Characteristic of CD7+ Acute Myeloid Leukaemia, *Cancer Genet Cytogenet* 73 69-74; Reading, C. L., et al. (1993) Expression of unusual immunophenotype combinations in acute myelogenous leukemia, Blood 81 3083-3090; Ossenkoppele, G. J., et al (2011) Review of the relevance of aberrant antigen expression by flow cytometry in myeloid neoplasms *British Journal of Haematology*; Lo Coco, F., et al. (1989) CD7 positive acute myeloid leukaemia: a subtype associated with cell immaturity, *British Journal of Haematology* 73 480-485; Kita, K., et al. (1983) Clinical Importance of CD7 Expression in Acute Myelocytic Leukemia, Blood 81, 2399-2405; Eto, T., et al. (1992) Biological characteristics of CD7 positive acute myelogenous leukaemia, British *lournal ol Haernatology* 82 508-511; Chang, H. (2004) Prognostic relevance of immunophenotyping in 379 patients with acute myeloid leukemia, *Leukemia Research* 28 43-48) and linked to poorer outcome.

The CD7+ subtype of AML is associated with increased leucocytosis, poor response to chemotherapy and poor overall and disease-free survival (Kahl, C., et al. (2001) CD7+ and CD56+ Acute Myelogenous Leukemia is a Distinct Biologic and Clinical Disease Entity. *Haematology and Blood Transfusion*, 40 112-119). Clinically, CD7+ AML patients are younger, more frequently males, have a higher incidence of central nervous system involvement and are often associated with less well differentiated subtypes of AML, further linked to poorer outcome (Tien, H. and Wang, C. (1998) CD7 Positive Hematopoietic Progenitors and Acute Myeloid Leukemia and other Minimally Differentiated Leukemia, *Leukemia and Lymphoma*, 3 93-98). The immaturity of the CD7+ AML cells has been further supported by the high expression of CD34 in this population. One study by Poeta et al, 1995, found that patients with CD7+ leukaemia had a significantly lower CR than those with the CD7− phenotype (32% versus 74%), indicating the degree of relapse and/or refractory nature of this subtype to standard of care (Poeta, G. D., et al. (1995) CD7 Expression in Acute Myeloid Leukemia. *Leuk. Lymphoma*, 17, 111-119).

CD7 is tightly correlated with and believed to be a hallmark of the FLT3-ITD+ AML subgroup. This subtype is associated with poorer clinical outcome due to deregulation of the FLT3 tyrosine kinase receptor, which signals to down regulate the translation of apoptotic proteins. As a result, deregulation in this receptor induces resistance to chemotherapy-induced cell death in the AML cell population (Rausei-Mills, V., et al. (2008) Aberrant Expression of CD7 in Myeloblasts Is Highly Associated With De Novo Acute Myeloid Leukemias With FLT3/ITD Mutation, *Am J Clin Pathol*, 129 624-629). As a particularly poor prognostic subtype of AML, the FLT3 AML subgroup is a desirable disease class for novel drug developers to target, with many new therapeutics, including kinase inhibitors and monospecific ADCs, specifically targeting this population.

Several mechanisms have been described to explain the aberrant expression of CD7 in AML. These include disease-specific irregular gene expression in leukemic cells (lineage infidelity), malignant transformation of pluripotent progenitor cells capable of lymphoid and myeloid differentiation or proliferation and maturation arrest of rare progenitor cells which may transiently express markers of different cell lineages during their normal cell differentiation (lineage promiscuity) (Tien, H. and Wang, C. (1998) CD7 Positive Hematopoietic Progenitors and Acute Myeloid Leukemia and other Minimally Differentiated Leukemia, *Leukemia and Lymphoma*, 3 93-98).

Transient CD7 expression has been reported in a subset of early progenitor cells capable of producing cells of both myeloid and lymphoid origin, but is lost during mature myeloid transformation (Tien, H. and Wang, C. (1998) CD7 Positive Hematopoietic Progenitors and Acute Myeloid Leukemia and other Minimally Differentiated Leukemia, *Leukemia and Lymphoma*, 3 93-98). In line with this, one study found that minimal and transitory co-expression of these two antigens had been identified on certain subsets of healthy heamatopoietic cells, including pluripotent stem cells ($CD33^{low}/CD7^{+/-}$), some myeloid progenitor cells ($CD33^{high}/CD7^{+/-}$) and some T cell progenitors ($CD33^{+/-}/CD7^{med}$), with co-expression lost during development (Barcena, A., et al. (1994) Tracing the Expression of CD7 and other Antigens during T- and Myeloid-cell Differentiation in the Human Fetal Liver and Thymus, Leukaemia and *Lymphoma* 17 1-11). It is therefore plausible that this co-expression pattern may be a result of the clonal expansion of a certain subset of progenitor cells, captured at a particular stage in development whereby these two antigens are transiently seen together, and that co-expression is amplified during the malignant transformation.

Whilst some transient co-expression may be evident for these two antigens in certain progenitor subsets, it is clear that the degree of expression of each antigen is low to negative. CD33 and CD7 do not exhibit a high level of co-expression within any stage of early haematopoietic development, with limited expression on selected minor subpopulations of early progenitors, not reflected across the entire progenitor pool.

Accordingly, there remains a need for more effective therapies with improved specificity for treating hematological malignancy, including AML.

BRIEF SUMMARY OF THE DISCLOSURE

In a first aspect, the invention provides a cell inhibiting agent that binds to CD33 for use in the treatment of a CD7+CD33+ hematological malignancy, wherein: said cell inhibiting agent that binds to CD33 is for administration in combination with a cell inhibiting agent that binds to CD7; or wherein said cell inhibiting agent that binds to CD33 additionally binds to CD7.

In a related aspect, the invention provides a method of treating a CD7+CD33+ hematological malignancy in an individual in need therefore, where the method comprises administering a cell inhibiting agent that binds to CD33 to the individual, wherein: said cell inhibiting agent that binds to CD33 is for administration in combination with a cell inhibiting agent that binds to CD7; or wherein said cell inhibiting agent that binds to CD33 additionally binds to CD7. It is preferred that the cell inhibiting agent is artificially generated.

In another related aspect, the invention provides a cell inhibiting agent that binds to CD33 for use in the manufacture of a medicament for a treatment of a CD7+CD33+ hematological malignancy, wherein: said cell inhibiting agent that binds to CD33 is for administration in combination with a cell inhibiting agent that binds to CD7; or wherein said cell inhibiting agent that binds to CD33 additionally binds to CD7.

In an embodiment, said cell inhibiting agent that binds to CD33 is capable of inducing CD33 receptor mediated internalization of said first cell inhibiting agent into a CD33+ cell, optionally wherein the CD33+ cell is an AML cell.

The said cell inhibiting agent that binds to CD33 may specifically bind to CD33.

In one embodiment, said cell inhibiting agent is an anti-CD33 antibody or antigen binding portion thereof capable of mediating antibody dependent cellular cytotoxicity. If the cell inhibiting agent is an anti-CD33 antibody, then such an antibody may be a full length antibody.

In one embodiment, said cell inhibiting agent is an anti-CD33 CAR-T. The cell inhibiting agent may comprises an immune effector cell. The immune effector cell may comprises a T cell and/or a NK cell. The immune effector cell is a T cell. The T cell may comprises a CD33+ T cell.

In one embodiment, said cell inhibiting agent comprises a cell killing portion and a CD33 binding portion. Optionally, said CD33 binding portion comprises an antibody or antigen binding fragment thereof. Optionally said cell killing portion is a cytotoxin. Said cytotoxin may be selected from: i) a peptide toxin or ii) a chemical toxin. Optionally, said cell inhibiting agent further comprises a linking portion. Said linking portion will preferably be between the cell killing portion and a CD33 binding portion.

In a further aspect, the invention provides a cell inhibiting agent that binds to CD7 for use in the treatment of a CD7+CD33+ hematological malignancy, wherein: the cell inhibiting agent that binds to CD7 is for administration in combination with a cell inhibiting agent that specifically binds to CD33; or wherein said inhibiting agent that binds to CD7 additionally binds to CD33.

In a related aspect, the invention provides a method of treating a CD7+CD33+ hematological malignancy in an individual in need of treatment thereof, wherein the method comprises the administration of: a cell inhibiting agent that binds to CD7 is for administration in combination with a cell inhibiting agent that specifically binds to CD33; or a cell inhibiting agent that binds to CD7 additionally binds to CD33. It is preferred that the cell inhibiting agent is artificially generated.

In a further related aspect, the invention provides a cell inhibiting agent that binds to CD7 for use in the manufacture of a medicament for the treatment of a CD7+CD33+ hematological malignancy, wherein: the cell inhibiting agent that binds to CD7 is for administration in combination with a cell inhibiting agent that specifically binds to CD33; or wherein said inhibiting agent that binds to CD7 additionally binds to CD33.

In an embodiment, said cell inhibiting agent that binds to CD7 is capable of inducing CD7 receptor-mediated internalization of said first cell inhibiting agent into a CD7+ cell, optionally wherein the CD7+ cell is an AML cell.

The said cell inhibiting agent that binds to CD7 may specifically bind to CD7.

In one embodiment, said cell inhibiting agent is an anti-CD7 antibody or antigen binding portion thereof capable of mediating antibody dependent cellular cytotoxicity. If the cell inhibiting agent is an anti-CD7 antibody, then such an antibody may be a full length antibody.

In one embodiment, said cell inhibiting agent is an anti-CD7 CAR-T. The cell inhibiting agent may comprises an immune effector cell. The immune effector cell may comprises a T cell and/or a NK cell. The immune effector cell is a T cell. The T cell may comprises a CD7+ T cell.

In one embodiment said cell inhibiting agent comprises a cell killing portion and a CD7 binding portion. Optionally, said CD7 binding portion comprises an antibody or antigen binding fragment thereof. Optionally, said cell killing portion is a cytotoxin. Said cytotoxin may selected from: i) a peptide toxin or ii) a chemical toxin. Optionally, said cell inhibiting agent further comprises a linking portion. Said linking portion will preferably be between the cell killing portion and a CD7 binding portion.

In a further aspect, the invention provides a combination of a cell inhibiting agent that binds to CD33 and a cell inhibiting agent binds to CD7 for use in treating a CD7+CD33+ hematological malignancy.

In a related aspect, the invention provides a method of treating a CD7+CD33+ hematological malignancy in an individual in need of treatment thereof, comprising administering a combination of a cell inhibiting agent that binds to CD33 and a cell inhibiting agent binds to CD7. It is preferred that the cell inhibiting agent is artificially generated.

In a further related aspect, the invention provides a combination of a cell inhibiting agent that binds to CD33 and a cell inhibiting agent binds to CD7 for use in the manufacture of a medicament for treating a CD7+CD33+ hematological malignancy.

In an embodiment, said cell inhibiting agent that binds to CD33 is capable of inducing CD33 receptor-mediated internalization of said first cell inhibiting agent into a CD33+ cell, optionally wherein the CD33+ cell is an AML cell.

In the combination, the cell inhibiting agent that binds to CD33 may specifically bind to CD33.

In an embodiment, said cell inhibiting agent that binds to CD33 is an anti-CD33 antibody or antigen binding portion thereof capable of mediating antibody dependent cellular cytotoxicity. If the cell inhibiting agent is an anti-CD33 antibody, such an antibody may be a full length antibody.

In an embodiment, said cell inhibiting agent that binds to CD33 is an anti-CD33 CAR-T. The cell inhibiting agent may comprises an immune effector cell. The immune effector cell may comprises a T cell and/or a NK cell. The immune effector cell is a T cell. The T cell may comprises a CD33+ T cell.

In an embodiment, said cell inhibiting agent that binds to CD33 comprises a cell killing portion and a CD33 binding portion. Optionally, said CD33 binding portion comprises an antibody or antigen binding fragment thereof. Optionally, said cell killing portion is a cytotoxin. Said cytotoxin may be selected from: i) a peptide toxin or ii) a chemical toxin.

Optionally, said cell inhibiting agent further comprises a linking portion. Said linking portion may be between the cell killing portion and a CD33 binding portion.

In an embodiment, said cell inhibiting agent that binds to CD7 is capable of inducing CD7 receptor mediated internalization of said first cell inhibiting agent into a CD7+ cell, optionally the CD7+ cell is an AML cell.

The said cell inhibiting agent that binds to CD7 may specifically bind to CD7.

In an embodiment, said cell inhibiting agent that binds to CD7 is an anti-CD7 antibody or antigen binding portion thereof capable of mediating antibody dependent cellular cytotoxicity.

In an embodiment, said cell inhibiting agent that binds to CD7 is an anti-CD7 CAR-T. The cell inhibiting agent may comprises an immune effector cell. The immune effector cell may comprises a T cell and/or a NK cell. The immune effector cell is a T cell. The T cell may comprises a CD7+ T cell.

In an embodiment, said cell inhibiting agent that binds to CD7 comprises a cell killing portion and a CD7 binding portion. Optionally, said CD7 binding portion comprises an antibody or antigen binding fragment thereof. Optionally, said cell killing portion is a cytotoxin. Said cytotoxin may selected from: i) a peptide toxin or ii) a chemical toxin. Optionally, said cell inhibiting agent that binds to CD7 further comprises a linking portion. Said linking portion will preferably be between the cell killing portion and a CD7 binding portion.

In a further aspect, the invention provides a cell inhibiting agent that bispecifically binds to CD33 and CD7 for use in the treatment of a CD7+CD33+ hematological malignancy.

In a related aspect, the invention provides a method of treating a CD7+CD33+ hematological malignancy in an individual in need thereof, comprising the administration of a cell inhibiting agent that bispecifically binds to CD33 and CD7. It is preferred that the cell inhibiting agent is artificially generated.

In a further related aspect, the invention provides a cell inhibiting agent that bispecifically binds to CD33 and CD7 for use in the manufacture of a medicament for the treatment of a CD7+CD33+ hematological malignancy.

In one embodiment, said cell inhibiting agent is capable of inducing CD33 and CD7 receptor mediated internalization of said cell inhibiting agent into a CD33+ and CD7+ cell, optionally wherein the CD33+ and CD7+ cell is an AML cell.

In one embodiment, said cell inhibiting agent is a bispecific antibody or antigen binding portion thereof, optionally wherein said bispecific antibody or antigen binding portion thereof is capable of mediating antibody dependent cellular cytotoxicity. If the cell inhibiting agent is an bispecific antibody, then such an antibody may be a full length antibody.

In one embodiment, said cell inhibiting agent is a bispecific anti-CD33 anti-CD7 CAR-T. The cell inhibiting agent may comprises an immune effector cell. The immune effector cell may comprises a T cell and/or a NK cell. The immune effector cell is a T cell. The T cell may comprises a CD33+ T cell, a CD7+ T cell, or a combination thereof.

In one embodiment, said cell inhibiting agent comprises: i) a cell killing portion; ii) a CD7 binding portion and ii) a CD33 binding portion. Optionally said CD33 binding portion comprises an antigen binding fragment of an antibody and/or said CD7 binding portion comprises an antigen binding fragment of an antibody. Optionally said cell killing portion is a cytotoxin. Said cytotoxin may be selected from: i) a peptide toxin or ii) a chemical toxin. Optionally, said cell inhibiting agent further comprises a linking portion. Said linking portion will preferably be between the cell killing portion and a CD33 and/or CD7 binding portion.

Features, integers, characteristics, binding moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and figures), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and figures), or to any novel one, or any novel combination, of the steps of any method or process so disclosed.

BRIEF DESCRIPTION OF THE DRAWINGS

Embodiments of the invention are further described hereinafter with reference to the accompanying drawings, in which.

DETAILED DESCRIPTION

Figure 1:
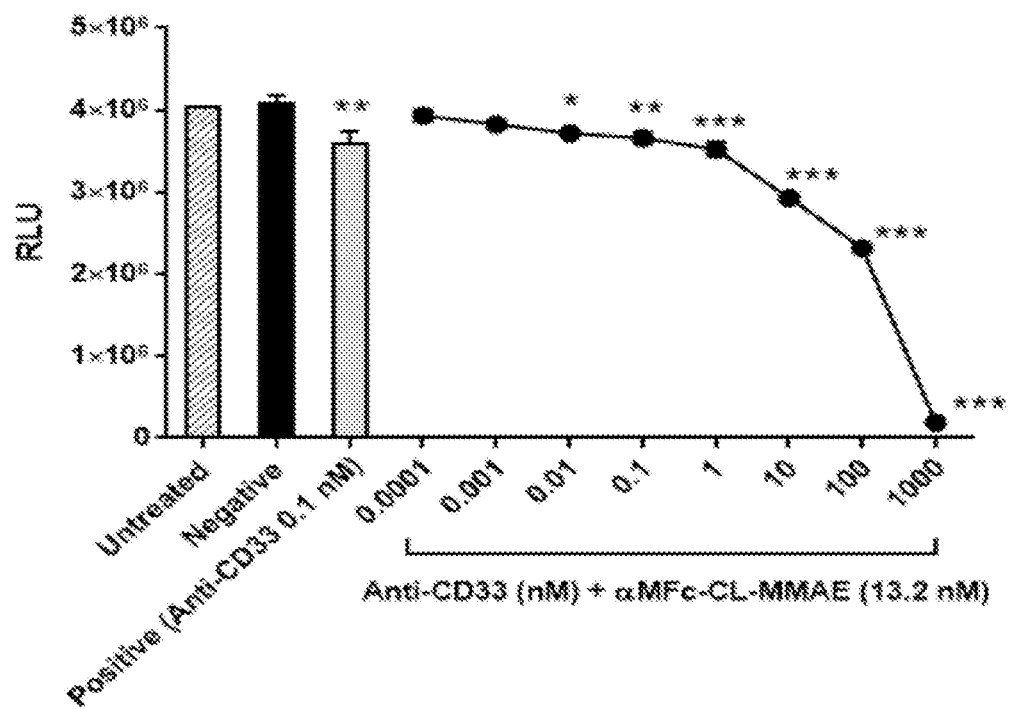
FIG. 1 is a graph showing the cytotoxic profile of Anti-CD33 in the presence of αMFc-CL-MMAE represented as RLU.

The inventors have surprisingly demonstrated that the dual targeting of CD7 and CD33 on AML cells provides a synergistic therapeutic effect. The inventors have demonstrated that this dual targeting provides a significant synergistic effect on the induction of AML cell death. Specifically, the inventors surprisingly identified that dual targeting of CD7 and CD33 in an AML disease cell line resulted in a 20-fold increase in cancer cell death compared to single targeting.

The inventors performed a panel of cell viability assays (Promega CellTiter-Glo®) to investigate the application of different potential target antigen combinations in AML. AML cell lines expressing the two antigens in each target antigen combination were selected, and incubated with an increasing concentration of primary monoclonal antibody, either alone or in combination. The addition of a defined concentration of secondary anti-Mouse Fc antibody linked to a cytotoxic payload, MMAE, with a cleavable linker was added to exert the 'ADC' effect. Post internalisation, the MMAE payload from the secondary antibody was released within the lysosome and resulted in cell death. The percentage viability of the cells was calculated and an $IC_{50}$ value was derived from the dataset.

The assay demonstrated that both the CD7 and CD33 antigens possess the required qualities for an ADC therapeutic. Both antigens, when bound by an antibody, internalised and directed the antibody towards the lysosome for payload release, resulting in cell death.

When targeted alone, both the CD7 and CD33 antibodies elicited poor cytotoxicity towards the antigen positive cells, with $IC_{50}$s of 158.2 nM and 163.6 nM respectively. However, when incubated in combination, a 20-fold increase in potency, 8.2 nM, was recorded. This suggests that targeting the two receptors in tandem drives rapid internalisation, resulting in a greater degree of payload reaching the lysosome at a given dose. This was not evident with the alternative combinations tested.

CD7 is a pan-leucocytic receptor expressed on progenitors of T and B lymphocytes, natural killer cells and dendritic cells (Hao, 2001; Sempowki, 1999) that plays an accessory role in T cell activation (Lazarovits, 1994; Stillwell, 2011) and persists on the surface of mature CD4<+>cells (Cotta, 2006; Lobac, 1985). CD7 has been widely studied as a target for delivery of cytotoxic molecules for leukaemia and lymphoma treatment (Peipp, 2002; Bremmer, 2006; Franker, 1997; Vallera, 1996; Waurzyniak, 1997).

CD33 is a 67 kDa plasma membrane protein that binds to sialic acid and is a member of the sialic acid-binding Ig-related lectin (SIGLEC) family of proteins. CD33 is known to be expressed on myeloid cells. CD33 expression has also been reported on a number of malignant cells.

Whilst CD33, a common myeloid antigen, is expressed on the majority of AML cells (De Propris, M. S., et al. (2011) High CD33 expression levels in acute myeloid leukemia cells carrying the nucleophosmin (NPM1) mutation, haematological, 96 1548-1551; Ehninger, A., et al. (2014) Distribution and levels of cell surface expression of CD33 and CD123 in acute myeloid leukemia, *Blood Cancer Journal*, 4 1-10) CD7, a common T and NK cell marker, is aberrantly expressed on a chemotherapy-resistant subpopulation (representing roughly 22%) of AML cells which confers a poor prognostic phenotype (Poeta, G. D., et al. (1995) CD7 Expression in Acute Myeloid Leukemia. *Leuk. Lymphoma*, 17, 111-119; Rohrs, S., et al. (2010) CD7 in acute myeloid leukemia: correlation with loss of wild-type CEBPA, consequence of epigenetic regulation, *Journal of Hematology & Oncology*, 3 1-7; Rausei-Mills, V., et al. (2008) Aberrant Expression of CD7 in Myeloblasts Is Highly Associated With De Novo Acute Myeloid Leukemias With FLT3/ITD Mutation, *Am J Clin Pathol*, 129 624-629; Shimamoto, T., et al. (1994) Clinical and Biological Characteristic of CD7+ Acute Myeloid Leukaemia, *Cancer Genet Cytogenet* 73 69-74; Reading, C. L., et al. (1993) Expression of unusual immunophenotype combinations in acute myelogenous leukemia, Blood 81 3083-3090; Ossenkoppele, G. J., et al (2011) Review of the relevance of aberrant antigen expression by flow cytometry in myeloid neoplasms *British Journal of Haematology* 153 421-436; Lo Coco, F., et al. (1989) CD7 positive acute myeloid leukaemia: a subtype associated with cell immaturity, *British Journal of Haematology* 73 480-485; Kita, K., et al. (1983) Clinical Importance of CD7 Expression in Acute Myelocytic Leukemia, Blood 81, 2399-2405; Eto, T., et al. (1992) Biological characteristics of CD7 positive acute myelogenous leukaemia, British *lournal ol Haernatology* 82 508-511; Chang, H. (2004) Prognostic relevance of immunophenotyping in 379 patients with acute myeloid leukemia, *Leukemia Research* 28 43-48).

The CD7+ subtype of AML is associated with increased leucocytosis, poor response to chemotherapy and poor overall and disease-free survival (Kahl, C., et al. (2001) CD7+ and CD56+ Acute Myelogenous Leukemia is a Distinct Biologic and Clinical Disease Entity. *Haematology and Blood Transfusion*, 40 112-119). Clinically, CD7 AML patients are younger, more frequently males, have a higher incidence of central nervous system involvement and are often associated with less well differentiated subtypes of AML, further linked to poorer outcome (Tien, H. and Wang, C. (1998) CD7 Positive Hematopoietic Progenitors and Acute Myeloid Leukemia and other Minimally Differentiated Leukemia, *Leukemia and Lymphoma*, 3 93-98). The immaturity of the CD7+ AML cells has been further supported by the high expression of CD34 in this population. One study by Poeta et al, 1995, found that patients with CD7+ leukaemia had a significantly lower CR than those with the CD7– phenotype (32% versus 74%), indicating the degree of relapse and/or refractory nature of this subtype to standard of care (Poeta, G. D., et al. (1995) CD7 Expression in Acute Myeloid Leukemia. *Leuk. Lymphoma*, 17, 111-119).

CD7 is tightly correlated with and believed to be a hallmark of the FLT3-ITD+ AML subgroup. This subtype is associated with poorer clinical outcome due to deregulation of the FLT3 tyrosine kinase receptor, which signals to down regulate the translation of apoptotic proteins and as a result, induces resistance to chemotherapy-induced cell death in the AML cell population (Rausei-Mills, V., et al. (2008) Aberrant Expression of CD7 in Myeloblasts Is Highly Associated With De Novo Acute Myeloid Leukemias With FLT3/ITD Mutation, *Am J Clin Pathol*, 129 624-629). As a particularly poor prognostic subtype of AML, the FLT3 AML subgroup is a desirable disease class for novel drug developers to target, with many new therapeutics, including kinase inhibitors and monospecific ADCs, specifically targeting this population.

Several mechanisms have been described to explain the aberrant expression of CD7 in AML. These include disease-specific irregular gene expression in leukemic cells (lineage infidelity), malignant transformation of pluripotent progenitor cells capable of lymphoid and myeloid differentiation or proliferation and maturation arrest of rare progenitor cells which may transiently express markers of different cell lineages during their normal cell differentiation (lineage promiscuity) (Tien, H. and Wang, C. (1998) CD7 Positive Hematopoietic Progenitors and Acute Myeloid Leukemia and other Minimally Differentiated Leukemia, *Leukemia and Lymphoma*, 3 93-98).

Transient CD7 expression has been reported in a subset of early progenitor cells capable of producing cells of both myeloid and lymphoid origin, but is lost during mature myeloid and lymphoid transformation (Tien, H. and Wang, C. (1998) CD7 Positive Hematopoietic Progenitors and Acute Myeloid Leukemia and other Minimally Differentiated Leukemia, *Leukemia and Lymphoma*, 3 93-98). In line with this, one study found that co-expression of these two antigens at low levels had been identified on certain subsets of healthy heamatopoietic cells, including pluripotent stem cells ($CD33^{low}/CD7^{+/-}$), some myeloid progenitor cells ($CD33^{high}/CD7^{+/-}$) and some T cell progenitors ($CD33^{+/-}/CD7^{med}$), but co-expression was lost during development (Barcena, A., et al. (1994) Tracing the Expression of CD7 and other Antigens during T- and Myeloid-cell Differentiation in the Human Fetal Liver and Thymus, *Leukaemia and Lymphoma* 17 1-11). It is therefore plausible that this co-expression pattern may be a result of the clonal expansion of a certain subset of progenitor cells, captured at a particular stage in development whereby these two antigens are transiently seen together and this expression is amplified during the malignant transformation.

Advantageously, whilst some transient co-expression may be evident for these two antigens in certain progenitor subsets, it is clear that the degree of expression of each antigen is low to negative. CD33 and CD7 do not exhibit a high level of co-expression within any stage of early haematopoietic development, with limited expression on selected minor subpopulations of early progenitors, not reflected across the entire progenitor pool.

This antigen combination was selected from a panel of potential AML combinations based on the fidelity of the co-expression pattern for leukaemic blasts. The synergistic action of the dual targeting was entirely unexpected and could not have been predicted.

The present invention provides a dual targeting therapeutic approach that simultaneously targets the disease specific co-expression of two cell surface antigens, CD7 and CD33, that are exclusive to the AML cell population, avoiding off target effects on healthy cells that may express just one of the two antigens. As such, the bispecific ADC proposed will have improved selectivity over other AML therapies. This selectivity will enable higher, more efficacious doses of the therapeutic to be delivered over an extended duration.

Accordingly, the invention provides a cell inhibiting agent that specifically binds to CD33 and a cell inhibiting agent that specifically binds to CD7 and therapeutic compositions thereof that can be administered simultaneously, separately or sequentially in a dual targeting therapy for treating a CD7+CD33+ hematological malignancy.

In a further aspect, the invention provides a combination of a cell inhibiting agent that specifically binds to CD33 and a cell inhibiting agent that specifically binds to CD7 and therapeutic compositions thereof for treating a CD7+CD33+ hematological malignancy.

The invention also provides a cell inhibiting agent that specifically binds to CD33 and to CD7 for treating a CD7+CD33+ hematological malignancy.

In a first aspect, the invention provides a cell inhibiting agent that specifically binds to CD33 for use in treating a CD7+CD33+ hematological malignancy, wherein said cell inhibiting agent that specifically binds to CD33 is prepared for administration in combination with a cell inhibiting agent that specifically binds to CD7.

In a further aspect, the invention provides a cell inhibiting agent that specifically binds to CD7 for use in treating a CD7+CD33+ hematological malignancy, wherein the cell inhibiting agent that specifically binds to CD7 is prepared for administration in combination with a cell inhibiting agent that specifically binds to CD33.

In a further aspect, the invention provides a combination of a cell inhibiting agent that specifically binds to CD33 and a cell inhibiting agent that specifically binds to CD7 for use in treating a CD7+CD33+ hematological malignancy.

In a further aspect, the invention provides a cell inhibiting agent that specifically binds to CD33 and CD7 for use in treating a CD7+CD33+ hematological malignancy.

In another aspect, the invention provides a cell inhibiting agent that specifically binds to CD33 and a cell inhibiting agent that specifically binds to CD7 and therapeutic compositions thereof that can be administered simultaneously, separately or sequentially in a dual targeting therapy for preventing or delaying recurrence of CD7+CD33+ hematological malignancy. In a further aspect, the invention provides a combination of a cell inhibiting agent that specifically binds to CD33 and a cell inhibiting agent that specifically binds to CD7 and therapeutic compositions thereof for preventing or delaying recurrence of CD7+CD33+ hematological malignancy. In a further aspect, the invention provides a cell inhibiting agent that specifically binds to CD33 and to CD7 and therapeutic compositions thereof for preventing or delaying recurrence of CD7+CD33+ hematological malignancy.

The cell inhibiting agents and therapeutic compositions thereof described herein may be for use in the manufacture of a medicament. As used herein "a medicament" refers to a substance used for medical treatment (i.e. a medicine). The medicament may be, e.g. a T cell product that is for use in adoptive cell transfer.

The cell inhibiting agents and therapeutic compositions thereof described herein may be used in a method for treating a CD7+CD33+ hematological malignancy in a subject in need thereof or for preventing or delaying recurrence of CD7+CD33+ hematological malignancy in a subject in need thereof.

Accordingly, a method for treating a CD7+CD33+ hematological malignancy in a subject in need thereof comprises:
i) administering to the subject an effective amount of cell inhibiting agent that specifically binds to CD33,
ii) administering to the subject a cell inhibiting agent that specifically binds to CD7,
wherein steps i) and ii) are separate, simultaneous or sequential, and in any order.

As used herein CD7 is preferably human CD7 and CD33 is preferably human CD33. In certain embodiments, the cell inhibiting agents specifically bind to CD7 and CD33 that are cell surface expressed. As used herein, the expression "cell surface-expressed" means one or more CD7 and/or CD33 protein(s) that is/are expressed on the surface of a cell in vitro or in vivo, such that at least a portion of a CD7 and/or a CD33 protein is exposed to the extracellular side of the cell membrane and is accessible to the cell inhibiting agents of the invention.

The term "CD7+CD33+ hematological malignancy" refers to a hematological malignancy characterized by the expression of both CD7 and CD33 on the surface of the malignant cells (e.g., a hematological malignancy that over expresses CD33 and/or CD7 on their cell surface and/or that express CD33 and/or CD7 at levels considered acceptable for therapy with the cell inhibiting agent that specifically binds to CD33, the cell inhibiting agent that specifically binds to CD7, or the cell inhibiting agent that specifically binds to CD7 and CD33).

CD7+CD33+ hematological malignancies include, but are not limited to, acute myeloid leukemia (AML), a myelodysplastic syndrome, a T-cell acute lymphoblastic leukemia, and a blastic plasmacytoid dendritic cell neoplasm (BPDCN).

In a preferred embodiment, the CD7+CD33+ hematological malignancy is AML.

The cell inhibiting agents of the invention can be administered intravenously or subcutaneously to a patient.

In another aspect, the invention provides a cell inhibiting agent that specifically binds to CD33 and a cell inhibiting agent that specifically binds to CD7 and therapeutic compositions thereof that can be administered simultaneously, separately or sequentially in a dual targeting therapy for preventing or delaying recurrence of CD7+CD33+ hematological malignancy. In a further aspect, the invention provides a combination of a cell inhibiting agent that specifically binds to CD33 and a cell inhibiting agent that specifically binds to CD7 and therapeutic compositions thereof for preventing or delaying recurrence of CD7+CD33+ hematological malignancy. In a further aspect, the invention provides a cell inhibiting agent that specifically binds to CD33 and to CD7 and therapeutic compositions thereof for preventing or delaying recurrence of CD7+CD33+ hematological malignancy.

As used herein, the terms "treat", "treating" and "treatment" are taken to include an intervention performed with the intention of preventing the development or altering the pathology of a disorder or symptom. Accordingly, "treatment" refers to both therapeutic treatment and prophylactic or preventative measures, wherein the object is to prevent or slow down (lessen) the targeted disorder or symptom. Accordingly, the term "treating" encompasses treating and/or preventing the development of a disorder or symptom. As used herein, "therapy" refers to the prevention or treatment of a disease or disorder. Therapy may be prophylactic or therapeutic.

In such aspects, the cell inhibiting agents of the invention are administered to a patient in remission from the hematological malignancy, resulting in preventing or delaying recurrence of the underlying hematological malignancy.

As used herein, a "patient" is typically a human who is undergoing treatment for, or has been diagnosed as having, hematological malignancy, preferably a CD7+CD33+ hematological malignancy. In some embodiments, the cell inhibiting agents are administered to a patient in remission from CD7+CD33+ hematological malignancy, whereby the recurrence of the hematological malignancy is prevented or delayed. In some embodiments, the patient lacks detectable cells of the hematological malignancy. As used herein, a "lack of detectable cells" is determined by standard diagnostic or prognostic methods. A patient in remission from AML typically exhibits resolution of abnormal clinical features, return to normal blood counts and normal hematopoiesis in the bone marrow with <5% blast cells, a neutrophil count of >1.000-1,500, a platelet count of >100,000, and disappearance of the leukemic clone. See, e.g., The Merck Manual, Sec. 11, Ch. 138 (17th ed. 1997): Estey, 2001, Cancer 92(5): 1059-1073.

In some embodiments, the patient in remission from the CD7+CD33+ hematological malignancy has not undergone a bone marrow transplant. In other embodiments, the patient in remission from the CD7+CD33+ hematological malignancy has undergone a bone marrow transplant. The bone marrow transplant can be either an autologous or an allogeneic bone marrow transplant.

In embodiments treating a CD7+CD33+ hematological malignancy (for example AML) and delaying preventing or delaying recurrence of CD7+CD33+ hematological malignancy (for example AML) involves the inducing AML cancer cell death and/or inhibiting AML cancer cell growth.

Cell inhibiting agents may be part of a composition (e.g. a therapeutic composition) that comprises the compound (i.e. the cell inhibiting agent(s)) and one or more other components. A composition may be a therapeutic composition that comprises the cell inhibiting agent and a pharmaceutically acceptable excipient, adjuvant, diluent and/or carrier. Therapeutic compositions may routinely contain pharmaceutically acceptable concentrations of salt, buffering agents, preservatives, compatible carriers, supplementary immune potentiating agents such as adjuvants and cytokines and optionally other therapeutic agents or compounds.

As used herein, "pharmaceutically acceptable" refers to a material that is not biologically or otherwise undesirable, i.e., the material may be administered to an individual along with the selected compound without causing any undesirable biological effects or interacting in a deleterious manner with any of the other components of the pharmaceutical composition in which it is contained.

Excipients are natural or synthetic substances formulated alongside an active ingredient (e.g. the vaccine, cell cycle inhibitor, modulator of an immune suppression mechanism, or immune check point inhibitor (as appropriate)), included for the purpose of bulking-up the formulation or to confer a therapeutic enhancement on the active ingredient in the final dosage form, such as facilitating drug absorption or solubility. Excipients can also be useful in the manufacturing process, to aid in the handling of the active substance concerned such as by facilitating powder flowability or non-stick properties, in addition to aiding in vitro stability such as prevention of denaturation over the expected shelf life. Pharmaceutically acceptable excipients are well known in the art. A suitable excipient is therefore easily identifiable by one of ordinary skill in the art. By way of example, suitable pharmaceutically acceptable excipients include water, saline, aqueous dextrose, glycerol, ethanol, and the like.

Adjuvants are pharmacological and/or immunological agents that modify the effect of other agents in a formulation. Pharmaceutically acceptable adjuvants are well known in the art. A suitable adjuvant is therefore easily identifiable by one of ordinary skill in the art.

Diluents are diluting agents. Pharmaceutically acceptable diluents are well known in the art. A suitable diluent is therefore easily identifiable by one of ordinary skill in the art.

Carriers are non-toxic to recipients at the dosages and concentrations employed and are compatible with other ingredients of the formulation. The term "carrier" denotes an organic or inorganic ingredient, natural or synthetic, with which the active ingredient is combined to facilitate the application. Pharmaceutically acceptable carriers are well known in the art. A suitable carrier is therefore easily identifiable by one of ordinary skill in the art As used herein, the terms "effective amount" and "therapeutically effective amount" refer to the quantity of the active therapeutic agent sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of, but not limited to, the following: (a) the inhibition of cancer cell growth (e.g. AML cells); and (b) the killing of cancer cells (e.g. AML cells).

The dose of cell inhibiting agents and therapeutic compositions thereof administered to a patient may vary depending upon the age and the size of the patient, target disease, conditions, route of administration, and the like. The preferred dose is typically calculated according to body weight or body surface area.

Methods of administration of the cell inhibiting agents and therapeutic compositions thereof include, but are not limited to, intradermal, intramuscular, intraperitoneal, intravenous, subcutaneous, intranasal, epidural, and oral routes. The cell inhibiting agents and therapeutic compositions thereof may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

Preferably, the dual targeting therapy described herein will provide a benefit to the treatment of a CD7+CD33+ hematological malignancy in a subject in need thereof. For example, the dual targeting therapy may have an additive or synergistic effect on the treatment of AML in a subject in need thereof. A dual targeting therapy is defined as affording an "additive effect", "synergistic effect" or a "synergistic treatment" if the effect is therapeutically superior, as measured by, for example, the extent of the response (e.g. apoptosis or cell viability), the response rate, the time to disease progression or the survival period, to that achievable on dosing one or other of the components of the dual targeting therapy at its conventional dose. For example, the effect of the dual targeting therapy is additive if the effect is therapeutically superior to the effect achievable with a cell inhibiting agent that specifically binds to CD33 alone or a cell inhibiting agent that specifically binds to CD7 alone. For example, the effect of the combination treatment may be synergistic if the effect of the combination treatment supersedes the effect of the individual treatments added together. Further, the effect of the combination is beneficial (e.g. additive or synergistic) if a beneficial effect is obtained in a group of subjects that does not respond (or responds poorly) to a cell-inhibiting agent that specifically binds to CD33 alone or a cell-inhibiting agent that specifically binds to CD7 alone. In addition, the effect of the combination treatment is defined as affording a benefit (e.g. additive or synergistic effect) if one of the components is dosed at its conventional dose and the other component is dosed at a reduced dose and the therapeutic effect, as measured by, for example, the extent of the response, the response rate, the time to disease progression or the survival period, is equivalent to or better than that achievable on dosing conventional amounts of either one of the components of the combination treatment. In particular, a benefit is deemed to be present if the conventional dose of cell inhibiting agent that specifically binds to CD33 or a cell inhibiting agent that specifically binds to CD7 may be reduced without detriment to one or more of the extent of the response, the response rate, the time to disease progression and survival data, in particular without detriment to the duration of the response, but with fewer and/or less troublesome side-effects than those that occur when conventional doses of each component are used.

The cell-inhibiting agent that specifically binds to CD33 and the cell-inhibiting agent that specifically binds to CD7 may be provided in a form which is suitable for sequential (consecutive), separate (before or after) and/or simultaneous (concurrent) administration to the subject, in any order. For example, a cell-inhibiting agent that specifically binds to CD33 may be provided in a form that is suitable for sequential, separate and/or simultaneous administration with a cell-inhibiting agent that specifically binds to CD7 (or vice versa).

In cases where the cell-inhibiting agent that specifically binds to CD33 and the cell-inhibiting agent that specifically binds to CD7 are administered simultaneously, the cell-inhibiting agent that specifically binds to CD33 and the cell-inhibiting agent that specifically binds to CD7 that are administered simultaneously may be administered as separate compositions that are administered at the same time, or may be administered as a combined composition that includes both.

The cell inhibiting agent that specifically binds to CD33 may be administered in any manner that allows the cell inhibiting agent to be in contact with the a CD33+CD7+ AML cell in a subject at the same point as the cell inhibiting agent that specifically binds to CD7 is in contact with a CD33+CD7+ AML cell in a subject. A person of ordinary skill in the art is able to identify an appropriate administration regimen.

Where the administration of the cell inhibiting agent that specifically binds to CD33 and the cell inhibiting agent that specifically binds to CD7 is sequential or separate, the delay in administering the second formulation should not be such as to lose the beneficial effect of the combination therapy.

In the context of the present invention, "targeting" and "dual targeting" are used herein to indicate that the cell inhibiting agent that specifically binds to CD33 and the cell inhibiting agent that specifically binds to CD7 serve to localize themselves preferentially to at least one tissue site at which their presence is desired. In the present invention, the cell inhibiting agents specifically bind to CD33, CD7 or CD33 and CD7 and thereby provide greater than average localization to at least one desired site in the body of a subject following administration to that subject. The targeting moiety in the present case will be selected to bind specifically to cell-surface receptor CD33. Where CD33 and CD7 are expressed and/or over-expressed in cells having certain disease states (such as for example AML), the cell inhibiting agent that specifically binds to CD33 and the cell inhibiting agent that specifically binds to CD7 may serve to target the complex to such disease-affected cells.

As used herein the term "cell inhibiting agent" refers to any agent that induces cell killing of a target cell or inhibits cell growth of a target cell. As used herein, "killing of a target cell" relates to an inhibition of protein synthesis, for example such that cell viability is reduced, or an induction of apoptosis resulting in elimination or death of target cells.

Assays to determine cell killing and apoptosis are well known in the art. Cytotoxicity assays assess the number of live and dead cells in a population after treatment with a pharmacological substance (e.g. an LDH cytotoxicity assay, or a live-dead cell assay). Apoptosis assays assess how cells are dying by measuring markers that are activated upon cell death (e.g. a PS exposure assay, a caspase activation assay, a DNA fragmentation assay, a GSH/GSSG determination, a LDH cytotoxicity assay, a live-dead cell assay, or a non-caspase protease activation assay).

As used herein "inhibit the cell growth" (e.g., referring to target cells) refers to any measurable decrease in the growth or proliferation of a target cell when contacted with a cell inhibiting agent according to the present invention as compared to the growth of the same cell not in contact with a cell inhibiting agent according to the present disclosure, e.g., the inhibition of growth of a cell by at least about 10%, 20%, 30%, 40%, 50%, 60%, 70%, 80%, 90%, 99%, or 100%. Assays to determine cell viability or proliferation are well known in the art. Cell viability assays assess how healthy the cells are by measuring markers of cellular activity (e.g. an ATP and ADP determination assay, a cell cycle assay, a cell proliferation assay, a cell viability assay, an LHD cytotoxicity assay, or a live-dead cell assay). Cell proliferation assays assess the growth rate of a cell population or to detect daughter cells in a growing population (e.g. a cell cycle assay, a cell proliferation assay, a cell viability assay, or a senescence assay).

As used herein, "CD33 expressing cell" and "CD33+ cell" refers to a cell with CD33 as surface antigen. As used herein, "CD7 expressing cell" and "CD7+ cell" refers to a cell with CD7 as surface antigen. As used herein, "CD33 and CD7 expressing cell" and "CD33+CD7+ cell" refers to a cell with both CD33 and CD7 as surface antigens.

As used herein "target cell" refers to a cell or cell-type characterized by the expression or overexpression of the target molecule CD7 and CD33. Any type of cell expressing CD7 and CD33 may be envisaged as a target cell for treatment with the cell inhibiting agents of the invention. In certain embodiments, the cell is a tumour cell, for example a tumour cell from a hematological malignancy, such as an AML cell.

In certain embodiments, the cell inhibiting agents described herein are capable of inducing CD33 receptor mediated internalization of said cell inhibiting agent into a CD33+ cell, and/or CD7 receptor mediated internalization of said cell inhibiting agent into a CD7+ cell. In certain embodiments, the cell inhibiting agent is a cell inhibiting agent that specifically binds to both CD33 and CD7 and is capable of inducing internalization of the agent into a CD7+CD33+ cell upon binding of both CD7 and CD33 on a cell surface.

As used herein, "CD33 receptor mediated internalization" refers to taken up by (i.e., entry of) a CD33+ cell upon binding to CD33 on the cell surface. For therapeutic applications, internalization in vivo is contemplated. As used herein, "CD7 receptor mediated internalization" refers to taken up by (i.e., entry of) a CD7+ cell upon binding to CD7 on the cell surface. For therapeutic applications, internalization in vivo is contemplated.

For therapeutic applications, the number of cell inhibiting agents internalized will be sufficient or adequate to kill an CD33+CD7+ cell, especially an CD7+CD33+ hematological cancer cell, such as an AML cell. Depending on the potency of the cell inhibiting agents, in some instances, the uptake of a single molecule into the cell is sufficient to kill the target cell to which the agent binds. Whether a cell inhibiting agent induces CD33 and/or CD7 receptor mediated internalization can be determined by various assays well known in the art. For internalization in vitro, the cells can be incubated in tissue culture dishes in the presence or absence of the relevant cell inhibiting agents added to the culture media and processed for microscopic analysis at desired time points. The presence of an internalized, labeled cell inhibiting agents in the cells can be directly visualized by microscopy or by autoradiography if radiolabeled cell inhibiting agents are used. Alternatively, in a quantitative biochemical assay, a population of cells comprising CD33+ CD7+ cells are contacted in vitro or in vivo with a radiolabeled test cell inhibiting agents and the cells (if contacted in vivo, cells are then isolated after a suitable amount of time) are treated with a protease or subjected to an acid wash to remove uninternalized cell inhibiting agents on the cell surface. The cells are ground up and the amount of protease resistant, radioactive counts per minute (cpm) associated with each batch of cells is measured by passing the homogenate through a scintillation counter. Based on the known specific activity of the radiolabeled cell inhibiting agents, the number of cell inhibiting molecules internalized per cell can be deduced from the scintillation counts of the ground-up cells. Cells are "contacted" with cell inhibiting agent in vitro preferably in solution form such as by adding the cells to the cell culture media in the culture dish or flask and mixing the antibody well with the media to ensure uniform exposure of the cells to the cell inhibiting agent. Instead of adding to the culture media, the cells can be contacted with the test cell inhibiting agent in an isotonic solution such as PBS in a test tube for the desired time period. In vivo, the cells are contacted with cell inhibiting agent by any suitable method of administering the test cell inhibiting agent such as the methods of administration described below when administered to a patient.

In certain embodiments, the cell inhibiting agents of the invention may be, but not limited to, antibodies and fragments thereof, ADC's, small-molecule drug conjugates (SMDCs), immunotoxins, peptide and non-peptide conjugates, imaging agents, therapeutic vaccines, nanoparticles. In particular embodiments, the cell inhibiting agents are antibodies and fragments thereof.

The terms "antibody" or "antibodies" as used herein refer to molecules or active fragments of molecules that bind to known antigens, particularly to immunoglobulin molecules and to immunologically active portions of immunoglobulin molecules, i.e. molecules that contain a binding site that immunospecifically binds an antigen (i.e. CD7 or CD33). The immunoglobulin according to the invention can be of any class (IgG, IgM, IgD, IgE, IgA and IgY) or subclass (e.g. IgG1, IgG2, IgG3, IgG4, IgA1 and IgA2) or subclasses (isotypes) of immunoglobulin molecule (e.g. IgG in IgG1, IgG2, IgG3, and IgG4, or IgA in IgA1 and IgA2).

Within the scope of the present invention the terms "antibody" or "antibodies" include monoclonal, polyclonal, chimeric, single chain, bispecific, human and humanized antibodies as well as active fragments thereof. Examples of active fragments of molecules that bind to known antigens include Fab, F(ab'), F(ab')$^2$, scFv and Fv fragments, including the products of a Fab immunoglobulin expression library and epitope-binding fragments of any of the antibodies and fragments mentioned above.

As used herein, the term "monoclonal antibody" refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody. For the purpose of the present invention, "monoclonal antibody" is also to be understood to comprise antibodies that are produced by a mother clone which has not yet reached full monoclonality.

As used herein, the term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are exemplary embodiments. Such mouse/human chimeric antibodies are the product of expressed immunoglobulin genes comprising DNA segments encoding mouse immunoglobulin variable regions and DNA segments encoding human immunoglobulin constant regions. Other forms of "chimeric antibodies" encompassed by the present disclosure are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. Nos. 5,202,238 and 5,204,244.

As used herein the term "humanized antibody" or "humanized version of an antibody" refers to antibodies in which the framework or "complementarity determining regions" (CDR) have been modified to comprise the CDR of an immunoglobulin of different specificity as compared to that of the parent immunoglobulin. In some exemplary embodiments, the CDRs of the VH and VL are grafted into the framework region of human antibody to prepare the "humanized antibody." See e.g. Riechmann, L., et al., Nature 332 (1988) 323-327; and Neuberger, M. S., et al., Nature 314 (1985) 268-270. The heavy and light chain variable framework regions can be derived from the same or different human antibody sequences. The human antibody sequences can be the sequences of naturally occurring human antibodies. Human heavy and light chain variable framework regions are listed e.g. in Lefranc, M.-P., Current Protocols in Immunology (2000)—Appendix 1P A.1P.1-A.1P.37 and are accessible via IMGT, the international ImMunoGeneTics information System® (http://imgt.cines.fr) or via http://vbase.mrc-cpe.cam.ac.uk, for example. Optionally the framework region can be modified by further mutations. Exemplary CDRs correspond to those representing sequences recognizing the antigens noted above for chimeric antibodies. In some embodiments, such humanized version is chimerized with a human constant region. The term "humanized antibody" as used herein also comprises such antibodies which are modified in the constant region to generate the properties according to the disclosure, especially in regard to C1q binding and/or FcR binding, e.g. by "class switching" i.e. change or mutation of Fc parts (e.g. from IgG1 to IgG4 and/or IgG1/IgG4 mutation).

As used herein the term "human antibody" is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice results in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M. D., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, A., et al. and Boerner, P., et al. are also available for the preparation of human monoclonal antibodies (Cole, A., et al., Monoclonal Antibodies and Cancer Therapy, Liss, A. R. (1985) p. 77; and Boerner, P., et al., J. Immunol. 147 (1991) 86-95). As already mentioned, according to the instant disclosure the term "human antibody" as used herein also comprises such antibodies which are modified in the constant region to generate the properties according to the disclosure, for example in regard to C1q binding and/or FcR binding, e.g. by "class switching" i.e. change or mutation of Fc parts (e.g. from IgG1 to IgG4 and/or IgG1/IgG4 mutation).

As used herein "single chain antibody" refers to single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883 or a bispecific single chain Fv (WO 03/11161).

As used herein the term "antibody fragment" refers to a portion of a full length antibody, the term "antigen binding fragment" refers to a variable domain thereof, or at least an antigen binding site thereof, for example the CDRs. Examples of antibody fragments include diabodies, single-chain antibody molecules, and multispecific antibodies formed from antibody fragments. scFv antibodies are, e.g., described in Huston, J. S., Methods in Enzymol. 203 (1991) 46-88. Antibody fragments can be derived from an antibody of the present invention by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

As used herein the term "bispecific antibodies" refers to antibodies that bind to two (or more) different antigens. A bispecific antibody typically comprises at least two different variable domains, wherein each variable domain is capable of specifically binding to a separate antigen. In certain aspects, the bispecific antibodies of the invention are human antibodies. As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs, specifically binds to a particular antigen. In the context of the present invention, the first antigen-binding domain specifically binds a first antigen (e.g., CD7), and the second antigen-binding domain specifically binds a second, distinct antigen (e.g., CD33). In certain aspects, the bispecific molecules are capable of simultaneously binding to human CD7 and human CD33.

In certain embodiments, a cell inhibiting agent that specifically binds to CD7 and CD33 is a bispecific antibody, such antibodies may be referred to as "anti-CD7×CD33" or "anti-CD7/anti-CD33" and so forth.

Any bispecific antibody format or technology may be used to make the bispecific antigen-binding molecules of the present invention. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, Mab2 bispecific formats (see, e.g., Klein et al. 2012, imAbs 4:6, 1-1 1, and references cited therein, for a review of the foregoing formats) and Fab-based bispecific formats. In certain embodiments, the bispecific antibody is a Fab-based anti-CD7×CD33 bispecific.

As used herein the term "specific" and "specifically" are used interchangeably to indicate that biomolecules other than CD7 or CD33 (or where the biomolecule is a bispecific molecule both CD7 and CD33) do not significantly bind to the antibody. In some embodiments, the level of binding to a biomolecule other than CD7 or CD33 is negligible (e.g., not determinable) by means of ELISA or an affinity determination.

By "negligible binding" a binding is meant, which is at least about 85%, particularly at least about 90%, more particularly at least about 95%, even more particularly at least about 98%, but especially at least about 99% and up to 100% less than the binding to CD7 or CD33.

The binding affinity of an antibody to a peptide or epitope may be determined with a standard binding assay, such as surface plasmon resonance technique (BIAcore®, GE-Healthcare Uppsala, Sweden). The term "surface plasmon resonance," as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51: 19-26; Jonsson, U., et al. (1991) Biotechniques 11:620-627; Johnsson, B., et al. (1995) J. Mol. Recognit. 8: 125-131; and Johnnson, B., et al. (1991) Anal. Biochem. 198:268-277.

In one embodiment, the cell inhibiting agents of the invention are capable of mediating antibody dependent cell cytotoxicity. Preferably in such embodiments, the cell inhibiting agents are antibodies, for example a fully human, humanized or chimeric antibody, or a bispecific antibody. Antibody dependent cellular cytotoxicity (ADCC) is an immune effector cell mediated mechanism which may contribute to anti-tumor activity of monoclonal antibodies (Weiner G J. Monoclonal antibody mechanisms of action in cancer. Immunol Res. 2007, 39(1-3):271-8). The relevance of ADCC for anti-tumor efficacy has been demonstrated in preclinical models, e.g. in mouse tumor models (e.g. Clynes R A, Towers T L, Presta L G, Ravetch J V. Inhibitory Fc receptors modulate in vivo cytoxicity against tumor targets. Nat Med. 2000 April; 6(4):443-6). Data from clinical trials support the relevance of ADCC for clinical efficacy of therapeutic antibodies (e.g. Weng W K, Levy R Two immunoglobulin G fragment C receptor polymorphisms independently predict response to rituximab in patients with follicular lymphoma. J Clin Oncol. 2003 November I; 21(21): 3940-7. Epub 2003 Sep. 15). Interactions of monoclonal antibodies with Fc receptors on immune cells contribute to ADCC. The Fc of antibodies can be modified in order to display enhanced affinity to Fc receptors (e.g. Presta LG Engineering of therapeutic antibodies to minimize immunogenicity and optimize function. Adv Drug Deliv Rev. 2006 Aug. 7; 58(5-6):640-56. Epub 2006 May 23). Such enhanced affinity to Fc receptors results in increased ADCC activity which may lead to increased anti-tumor efficacy in patients.

In an alternative embodiment, the cell inhibiting agents of the invention are immunoresponsive cells which expresses a chimeric antigen T cell receptor protein (CAR), wherein the chimeric T cell receptor protein specifically binds to CD7 or CD33. In one embodiment immunoresponsive cell is bispecific and which a chimeric antigen T cell receptor protein (CAR), wherein the chimeric T cell receptor protein specifically binds to CD7 and a chimeric antigen T cell receptor protein (CAR), wherein the chimeric T cell receptor protein specifically binds to CD33. The immunoresponsive cell expressing the CAR may be selected from the group consisting of a T cell, a hematopoietic stem cell, a natural killer cell, a natural killer T cell, a B cell and a cell of monocytic lineage. In a particular embodiment, the immunoresponsive cell is a T cell.

In some embodiments, the immunoresponsive cell is autologous to the subject. In another embodiment, the immunoresponsive cell is not autologous to the subject. In a particular embodiment, the immunoresponsive cell is a T cell and is autologous to the subject to be treated.

In some embodiments, the cell inhibiting agent (e.g. the cell inhibiting agent that specifically binds to CD33 and/or the cell inhibiting agent that specifically binds to CD7, or the cell inhibiting agent that specifically binds to CD7 and CD33) comprises a binding portion (i.e. a CD33 binding portion, a CD7 binding portion, or a CD7 and a CD33 binding portion) and a cell killing portion. In certain embodiments, the cell binding portion is an antibody or antigen binding fragment thereof, an aptamer, a peptide or a non-peptide small molecule. In particular embodiments the cell binding portion is an antibody or antigen binding fragment thereof. In one embodiment, the cell inhibiting agent comprises a binding portion and a cell killing portion, wherein the binding portion is an anti-CD7 antibody or binding portion thereof. In one embodiment, the cell inhibiting agent comprises a binding portion and a cell killing portion, wherein the binding portion is an anti-CD33 antibody or binding portion thereof. In one embodiment, the cell inhibiting agent comprises a binding portion and a cell killing portion, wherein the binding portion is an anti-CD7 anti-CD33 bispecific antibody or binding portion thereof.

In some embodiments, the cell inhibiting agent comprises a cytotoxic or cytostatic agent, i.e. a compound that kills or inhibits tumour cells. Such agents may impart their cytotoxic and cytostatic effects by mechanisms including tubulin binding, DNA binding, proteasome and/or topoisomerase inhibition.

The cytotoxic or cytostatic agent may be, for example, a peptide toxin, a small molecule toxin or a radioisotope.

In one embodiment the cytotoxic or cytostatic agent may be a tubulin inhibitor; or a DNA interacting agent. Tubulin inhibitors modulate tubulin polymerization. DNA interacting agents target cellular DNA.

In an embodiment the cytotoxic or cytostatic agent is a tubulin inhibitor. In an embodiment, the tubulin inhibitor is selected from the group consisting of: (a) an auristatin; and (b) a maytansine derivative. In an embodiment, the cytotoxic or cytostatic agent is an auristatin. Auristatins include synthetic derivatives of the naturally occurring compound Dolastatin-10. Auristatins are a family of antineoplastic/cytostatic pseudopeptides. Dolastatins are structurally unique due to the incorporation of 4 unusual amino acids (Dolavaine, Dolaisoleuine, Dolaproine and Dolaphenine) identified in the natural biosynthetic product. In addition, this class of natural product has numerous asymmetric centres defined by total synthesis studies by Pettit et al (U.S. Pat. No. 4,978,744). It would appear from structure activity relationships that the Dolaisoleuine and Dolaproine residues appear necessary for antineoplastic activity (U.S. Pat. Nos. 5,635,483 and 5,780,588). In an embodiment, the auristatin is selected from the group consisting of: Auristatin E (AE); Monomethylauristatin E (MMAE); Auristatin F (MMAF); vcMMAE; and vcMMAF. In an embodiment, the cytotoxic or cytostatic agent is a maytansine or a structural analogue of maytansine. In an embodiment, the cytotoxic or cytostatic agent is a maytansine. Maytansines include structurally complex antimitotic polypeptides. Maytansines are potent inhibitors of microtubulin assembly which leads towards apoptosis of tumour cells. In an embodiment the maytansine is selected from the group consisting of: Mertansine (DM1); and a structural analogue of maytansine such as DM3 or DM4. Preferably, the drug is mertansine (DM1).

In an embodiment, the cytotoxic or cytostatic agent is DNA interacting agent. In an embodiment, the DNA interacting agent is selected from the group consisting of: (a) calicheamicins, (b) duocarmycins and (c) pyrrolobenzodiazepines (PBDs). In an embodiment, the cytotoxic or cytostatic agent is a calicheamicin. Calicheamicin is a potent cytotoxic agent that causes double-strand DNA breaks, resulting in cell death. Calicheamicin is a naturally occurring enediyne antibiotic (A. L. Smith et al, J. Med. Chem., 1996, 39, 11, 2103-2117). Calicheamicin was found in the soil microorganism Micromonosporaechinospora. In an embodiment, the calicheamicin is calicheamicin gamma 1. In an embodiment, the drug is a duocarmycin. Duocarmycins are potent anti-tumour antibiotics that exert their biological effects through binding sequence-selectively in the minor groove of DNA duplex and alkylating the N3 of adenine (D. Boger, Pure & Appl. Chem., 1994, 66, 4, 837-844). In an embodiment, the duocarmycin is selected from the group consisting of: Duocarmycin A; Duocarmycin B1; Duocarmycin B2; Duocarmycin C1; Duocarmycin C2; Duocarmycin D; Duocarmycin SA; Cyclopropylbenzoindole (CBI) duocarmycin; Centanamycin; Rachelmycin (CC-1065); Adozelesin; Bizelesin; and Carzelesin. In an embodiment, the cytotoxic or cytostatic agent is a pyrrolobenzodiazepine. Pyrrolobenzodiazepines (PBDs) are a class of naturally occurring anti-tumour antibiotics. Pyrrolobenzodiazepines are found in *Streptomyces*. PBDs exert their anti-tumour activity by covalently binding to the DNA in the minor groove specifically at purine-guanine-purine units. They insert on to the N2 of guamine via an aminal linkage and, due to their shape, they cause minimal disruption to the DNA helix. It is believed that the formation of the DNA-PBD adduct inhibits nucleic acid synthesis and causes excision-dependent single and double stranded breaks in the DNA helix. As synthetic derivatives the joining of two PBD units together via a flexible polymethylene tether allows the PBD dimers to cross-link opposing DNA strands producing highly lethal lesions. In an embodiment, the cytotoxic or cytostatic agent is a synthetic derivative of two pyrrolobenzodiazepines units joined together via a flexible polymethylene tether. In an embodiment, the pyrrolobenzodiazepine is selected from the group consisting of: Anthramycin (and dimers thereof); Mazethramycin (and dimers thereof); Tomaymycin (and dimers thereof); Prothracarcin (and dimers thereof); Chicamycin (and dimers thereof); Neothramycin A (and dimers thereof); Neothramycin B (and dimers thereof); DC-81 (and dimers thereof); Sibiromycin (and dimers thereof); Porothramycin A (and dimers thereof); Porothramycin B (and dimers thereof); Sibanomycin (and dimers thereof); Abbeymycin (and dimers thereof); SG2000; and SG2285.

In an embodiment, the cytotoxic or cytostatic agent is a drug that targets DNA interstrand crosslinks through alkylation. A drug that targets DNA interstrand crosslinks through alkylation is selected from: a DNA targeted mustard; a guanine-specific alkylating agent; and a adenine-specific alkylating agent. In an embodiment, the cytotoxic or cytostatic agent is a DNA targeted mustard. For example, the DNA targeted mustard may be selected from the group consisting of: an oligopyrrole; an oligoimidazole; a Bis-(benzimidazole) carrier; a Polybenzamide Carrier; and a 9-Anilinoacridine-4-carboxamide carrier.

In an embodiment, the cytotoxic or cytostatic agent is selected from the group consisting of: Netropsin; Distamycin; Lexitropsin; Tallimustine; Dibromotallimustine; PNU 157977; and MEN 10710.

In an embodiment, the cytotoxic or cytostatic agent is a Bis-(benzimidazole) carrier. Preferably, the drug is Hoechst 33258.

A guanine-specific alkylating agent is a highly regiospecific alkylating agents that reacts at specific nucleoside positions. In an embodiment, the cytotoxic or cytostatic agent is a guanine-specific alkylating agent selected from the group consisting of: a G-N2 alkylators; a A-N3 alkylator; a mitomycin; a carmethizole analogue; a ecteinascidin analogue. In an embodiment, the mitomycin is selected from: Mitomycin A; Mitomycin C; Porfiromycin; and KW-2149. In an embodiment, the a carmethizole analogue is selected from: Bis-(Hydroxymethyl)pyrrolizidine; and NSC 602668. In an embodiment, the ecteinascidin analogue is Ecteinascidin 743.

Adenine-specific alkylating agents are regiospecific and sequence-specific minor groove alkylators reacting at the N3 of adenines in polypyrimidines sequences.

Cyclopropaindolones and duocamycins may be defined as adenine-specific alkylators. In an embodiment, the cytotoxic or cytostatic agent is a cyclopropaindolone analogue. Preferably, the drug is selected from: adozelesin; and carzelesin.

In an embodiment, the cytotoxic or cytostatic agent is a benz[e]indolone. Preferably, the cytotoxic or cytostatic agent is selected from: CBI-TMI; and iso-CBI.

In an embodiment, the cytotoxic or cytostatic agent is bizelesin.

In an embodiment, the cytotoxic or cytostatic agent is a Marine Antitumor Drug. Marine Antitumor Drugs has been a developing field in the antitumor drug development arena (I. Bhatnagar et al, Mar. Drugs 2010, 8, P 2702-2720 and T. L. Simmons et al, Mol. Cancer Ther. 2005, 4(2), P 333-342). Marine organisms including sponges, sponge-microbe symbiotic association, gorgonian, actinomycetes, and soft coral have been widely explored for potential anticancer agents.

In an embodiment, the cytotoxic or cytostatic agent is selected from: Cytarabine, Ara-C; Trabectedin (ET-743); and EribulinMesylate. In an embodiment, the EribulinMesylate is selected from: (E7389); Soblidotin (TZT 1027); Squalamine lactate; CemadotinPlinabulin (NPI-2358); Plitidepsin; Elisidepsin; Zalypsis; Tasidotin, Synthadotin; (ILX- 651); Discodermolide; HT1286; LAF389; Kahalalide F; KRN7000; Bryostatin 1; Hemiasterlin (E7974); Marizomib; Salinosporamide A; NPI-0052); LY355703; CRYPTO 52; Depsipeptide (NSC630176); Ecteinascidin 743; Synthadotin; Kahalalide F; Squalamine; Dehydrodidemnin B; Didemnin B; Cemadotin; Soblidotin; E7389; NVP-LAQ824; Discodermolide; HTI-286; LAF-389; KRN-7000 (Agelasphin derivative); Curacin A; DMMC; Salinosporamide A; Laulimalide; Vitilevuamide; Diazonamide; Eleutherobin; Sarcodictyin; Peloruside A; Salicylihalimides A and B; Thiocoraline; Ascididemin; Variolins; Lamellarin D; Dictyodendrins; ES-285 (Spisulosine); and Halichondrin B.

The following cytotoxic or cytostatic agent are also encompassed by the present invention: Amatoxins (α-amanitin)-bicyclic octapeptides produced by basidiomycetes of the genus *Amanita*, e.g. the Green Deathcap mushroom; Tubulysins; Cytolysins; dolabellanins; Epothilone A, B, C, D, E, F. Epothilones—constitute a class of non-taxane tubulin polymerisation agents and are obtained by natural fermentation of the myxobacterium *Sorangium cellulosum*. These moieties possess potent cytotoxic activity which is linked to the stabilisation of microtubules and results in mitotic arrest at the G2/M transition. Epothilones have demonstrated potent cytotoxicity across a panel of cancer cell lines and has often exhibited greater potency than paclitaxel (X.: Pivot et al, European Oncology, 2008; 4(2), P 42-45). In an embodiment, the drug is amatoxin. In an embodiment, the drug is tubulysin. In an embodiment, the drug is cytolysin. In an embodiment, the drug is dolabellanin. In an embodiment, the drug is epothilone.

The following cytotoxic or cytostatic agent are also encompassed by the present invention. In an embodiment, the drug is selected from: Doxorubicin; Epirubicin; Esorubicin; Detorubicin; Morpholino-doxorubicin; Methotrexate; Methopterin; Bleomycin; Dichloromethotrexate; 5-Fluorouracil; Cytosine-β-D-arabinofuranoside; Taxol; Anguidine; Melphalan; Vinblastine; Phomopsin A; Ribosome-inactivating proteins (RIPs); Daunorubicin; Vinca alkaloids; Idarubicin; Melphalan; Cis-platin; Ricin; Saporin; Anthracyclines; Indolino-benzodiazepines; 6-Mercaptopurine; Actinomycin; Leurosine; Leurosideine; Carminomycin; Aminopterin; Tallysomycin; Podophyllotoxin; Etoposide; Hairpin polyamides; Etoposide phosphate; Vinblastine; Vincristine; Vindesine; Taxotere retinoic acid; N8-acetyl spermidine; Camptothecin; Esperamicin; and Ene-diynes.

In one embodiment, the cell inhibiting agent comprises a binding portion and a cell killing portion, wherein the binding portion is an anti-CD7 antibody or binding portion thereof and wherein the cell killing portion is a peptide toxin, for example an auristatin such as MMAE. In one embodiment, the cell inhibiting agent comprises a binding portion and a cell killing portion, wherein the binding portion is an anti-CD33 antibody or binding portion thereof and wherein the cell killing portion is a peptide toxin, for example an auristatin such as MMAE. In one embodiment, the cell inhibiting agent comprises a binding portion and a cell killing portion, wherein the binding portion is an anti-CD7 anti-CD33 bispecific antibody or binding portion thereof and wherein the cell killing portion is a peptide toxin, for example an auristatin such as MMAE.

In certain embodiments, the cell inhibiting agent comprises a binding portion that is conjugated to a cell killing portion. Such conjugates may be prepared by in vitro methods known to one of ordinary skill in the art. Techniques for conjugating cytotoxic or cytostatic agent to proteins, and in particular to antibodies, are well-known. (See, e.g., Alley et ah, Current Opinion in Chemical Biology 2010 14: 1-9; Senter, Cancer J., 2008, 14(3): 154-169.)

In certain embodiments, a linking group is used to conjugate the binding portion and the cell killing portion.

The linker can be cleavable under intracellular conditions, such that cleavage of the linker releases the cell killing portion from the binding portion in the intracellular environment. The cleavable linker can be, e.g., a peptidyl linker that is cleaved by an intracellular peptidase or protease enzyme, including a lysosomal or endosomal protease. Cleaving agents can include cathepsins B and D and plasmin (see, e.g., Dubowchik and Walker, Pharm. Therapeutics 83:67-123, 1999). Most typical are peptidyl linkers that are cleavable by enzymes that are present in NTB-A-expressing cells. For example, a peptidyl linker that is cleavable by the thiol-dependent protease cathepsin-B, which is highly expressed in cancerous tissue, can be used {e.g., a linker comprising a Phe-Leu or a Val-Cit peptide).

The cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used.

Other linkers are cleavable under reducing conditions (e.g., a disulfide linker). The cleavable linker can also be a malonate linker (Johnson et al, Anticancer Res. 15:1387-93, 1995), a maleimidobenzoyl linker (Lau et al, Bioorg-MedChem. 3: 1299-1304, 1995), or a 3'-N-amide analog (Lau et al, Bioorg-Med-Chem. 3: 1305-12, 1995).

In some embodiments the linker can be a protease cleavable linker, for example a valine-citrulline, which may be cleaved by cathepsin B in the lysosome.

The linker also can be a non-cleavable linker, such as an maleimido-alkylene- or maleimide-aryl linker that is directly attached to the therapeutic agent and released by proteolytic degradation of the binding portion.

In certain embodiments, the cell inhibiting agent comprise a binding portion and a cell killing portion which are administered separately and which bind in vivo to collectively form the cell inhibiting agent. For example, the cell binding portion is administered first and the cell inhibiting agent is administered simultaneously, or preferably subsequently, which binds in vivo to the cell binding portion. Specific binding pairs suitable for providing the cell binding portion and cell inhibiting agent with mutual affinity are well known in the art (e.g. biotin with avidin or streptavidin, antibody binding domains with antigens).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

Example 1: Determining the IC$_{50}$ of 5 Monoclonal Antibodies (Alone and in Combination) in Kasumi-3 Cell Line Experimental Conditions

TABLE A

Overview of experimental conditions tested.

| Cell Line | Primary Antibodies (and combinations) | Secondary Antibody | Readout |
|---|---|---|---|
| Kasumi-3 ATCC ® CRL-2725 ™ | CD(A) CD(B) CD(C) CD(A) and CD(B) CD(A) and CD(C) | Anti-Fc linked to toxin (MMAE) | Cell viability assay |

Note:
CD(A) = CD33; CD(B) = CD 7; CD(C) = CD13

Number of Samples to be Tested
  5 antibodies or combinations*8 concentrations*1 cell line*3 (triplicates)=120 Negative Control (Anti-Fc linked to MMAE)*1 concentration*1 cell line*3 (triplicates)=3
  3 Positive Control (Primary antibodies)*1 concentration*1 cell line*3 (triplicates)=9
  Control (Cells without antibody treatment)*1 cell line*3 (triplicates)=3
TOTAL=135 Tests 2. Materials i. Kasumi-3: ATCC® CRL-2725™
ii. RPMI-1640 Medium: ATCC® 30-2001™
iii. Fetal Bovine Serum (FBS): ATCC® 302020™
iv. Dulbecco's phosphate-buffered saline (DPBS): Gibco™
v. Monoclonal antibodies: o Anti-CD33 antibody o Anti-CD7 antibody o Anti-CD13 antibody
vi. Secondary antibody
  Anti-Mouse IgG Fc-MMAE Antibody with Cleavable Linker (αMFc-CL-MMAE): Moradec
vii. Non-adherent culture flasks
viii. CellTiter-Glo® Luminescent Cell Viability Assay: Promega
ix. 96 well plates (tissue grade-white)

3. Methods 3.1 Cell Culture
Kasumi-3 cells were maintained in suspension with complete growth media (RPMI-1640 with 20% FBS) at 37° C. in a 5% $CO_2$ incubator. The cell density was maintained between $3 \times 10^5$ to $3 \times 10^6$ cells/mi, with media change in intervals of 2-3 days.

3.2 Cytotoxicity Detection Using CellTiter-Glo® Luminescent Cell Viability Assay
i. Freshly split Kasumi-3 cells were seeded into 96-well white plates in culture medium at density of 20,000 cells per well in 100 µl culture media.
ii. The primary monoclonal antibody (CD33, CD7 and CD13) were diluted in culture media and added to the plates to obtain the desired concentration range (0.0001 to 1000 nM).
iii. The cells were then incubated in the presence of the primary antibody for 5 to 10 minutes.
iv. In the meantime, the secondary antibody (αMFc-CL-MMAE) was diluted in culture medium. After incubation with the primary antibodies, the αMFc-CL-MMAE was added to the wells to obtain 13.2 nM per well.
v. Conditions such as Blank, Control, Negative Control and Positive Control were also included in each assay plate. Refer to Tables 1-5 for the plate layouts for Kasumi-3 with Anti-CD33, Anti-CD7, Anti-CD13, Anti-CD33+Anti-CD7 combination and Anti-CD33+Anti-CD13 combination respectively.
  Blank=Culture media only
  Control=Cells with no treatment
  Negative Control=Cells treated with 13.2 nM αMFc-CL-MMAE
  Positive Control=Cells treated with 0.1 nM Primary Antibodies
vi. The plates were incubated for 72 hours.
vii. After 72 hours of incubation the 100 µl of CellTiter-Glo Reagent was added to each well.
viii. The contents were mixed for 2 minutes on an orbital shaker to induce cell lysis and incubated at room temperature for 10 minutes.
ix. The luminescence intensity was measured using the Promega GloMax® Explorer instrument.

3.3 Data Analysis
The average reading of the blank was subtracted from all the other readings. Blank contained only the culture medium and represented as the background for the assay plate. The data were then statistically analysed (One-way ANOVA followed by post-hoc Dunnett's multiple comparisons test) and plotted using GraphPad Prism 7.02 software. The luminescence intensity is represented as Relative Luminescence Unit (RLU) on the y-axis and the different conditions and Primary Antibody concentrations were represented on the x-axis.

The Percentage Viability (% Viability) of the cells were calculated taking Control (untreated) as 100% viable. Percentage Viability of the other cells were normalised to the Control. The data was plotted in GraphPad Prism 7.02 software using the Non-linear regression curve. The IC$_{50}$ is defined as the concentration of the relevant primary antibodies that induces 50% cytotoxic effect in the presence of the secondary antibody drug conjugate (αMFc-CL-MMAE). This was calculated using % Viability curve analysed by non-linear regression curve fit.

4. Results

4.1 Cytotoxicity Profile of Anti-CD33 Antibody to Kasumi-3 Cells

The raw data and data after Blank subtraction for the luminescence intensity for Anti-CD33 treatment are given in Tables 6 and 7 respectively. The graphical representation of Table 7 is given in FIG. 1. FIG. 1 shows a statistically significant decrease in Kasumi-3 cell viability was observed with concentrations above 0.01 nM Anti-CD33 antibody in presence of 13.2 nM αMFc-CL-MMAE when analysed using One-way ANOVA, followed by Dunnett's post-hoc multiple comparison test (*p<0.02; p<0.005; *p<0.0003, <0.0001; ±SEM). The quantifications are expressed as Average (±Standard Error Mean [SEM]).

One-way ANOVA followed by post-hoc Dunnett's multiple comparisons test was performed on Table 7 data. A statistically significant decrease in Kasumi-3 viability was observed with 0.01, 0.1, 1, 10, 100 and 1000 nM Anti-CD33 antibody in presence of αMFc-CL-MMAE when compared to Untreated cells (*p<0.02; p<0.005; *p<0.001).

Figure 2:
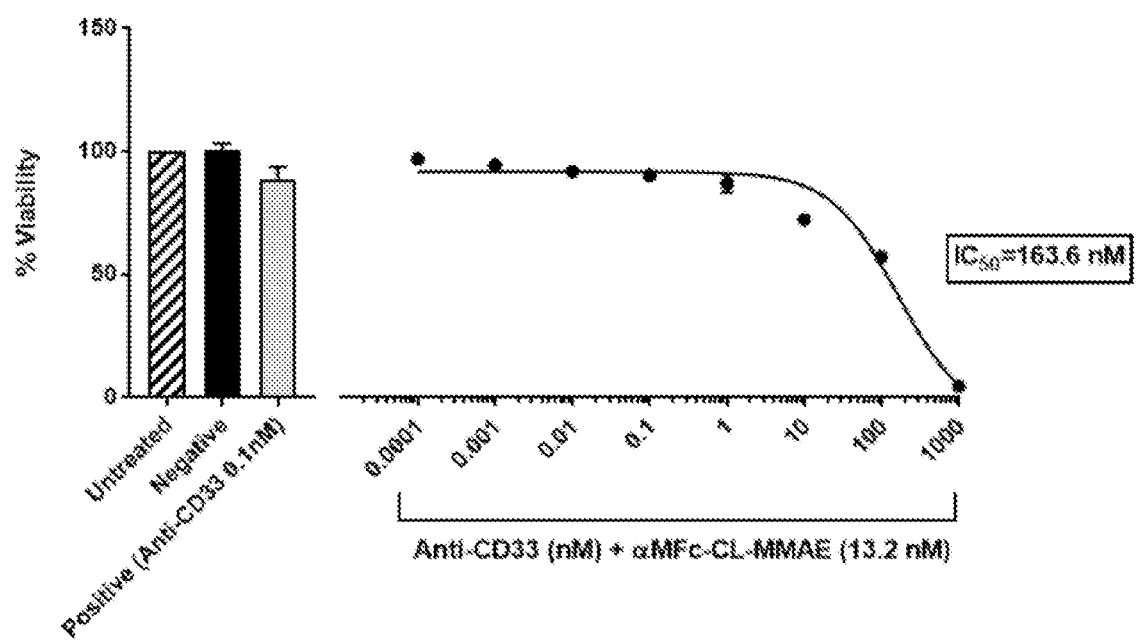
FIG. 2 is a graph showing the percentage viability of Kasumi-3 with Anti-CD33 and αMFc-CL-MMAE Treatment.

The data for % Viability is given in Table 8 and graphically represented in FIG. 2. FIG. 2 shows a non-liner regression curve for Anti-CD33 and αMFc-CL-MMAE Treatment. A $IC_{50}$=163.6 nM was observed.

The $IC_{50}$ of 163.6 nM was obtained from the non-linear regression curve.

4.2 Cytotoxicity Profile of Anti-CD7 Antibody to Kasumi-3 Cells

Figure 3:
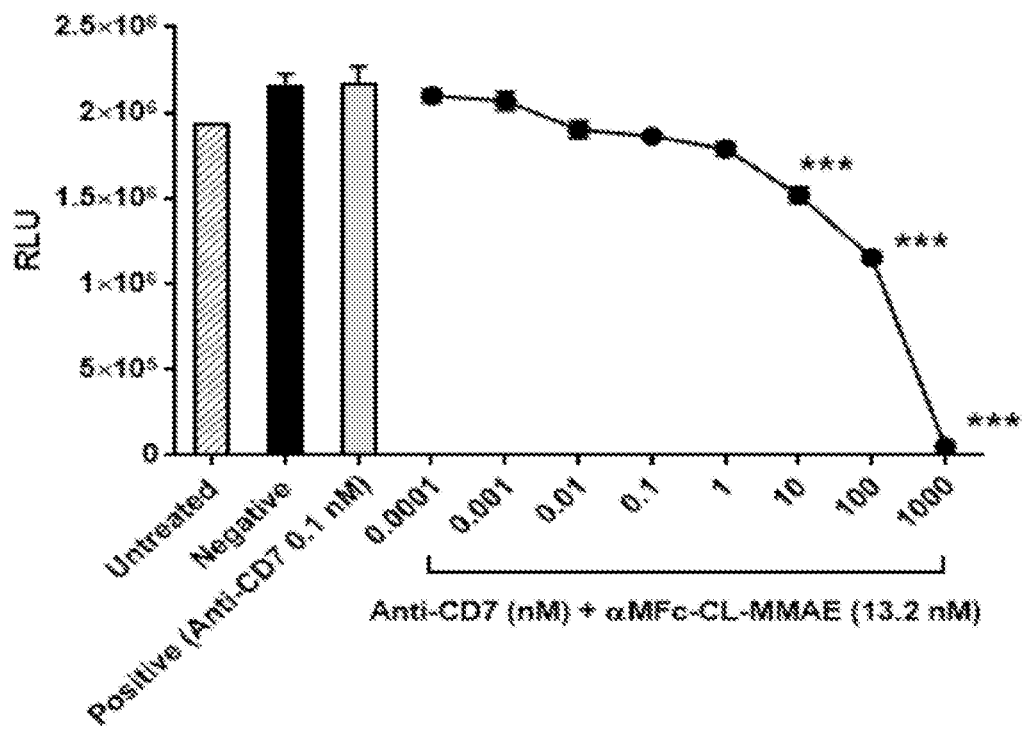
FIG. 3 is a graph showing the cytotoxic profile of Anti-CD7 in the presence of αMFc-CL-MMAE represented as RLU.

The raw data and data after Blank subtraction for the luminescence intensity for Anti-CD7 treatment are given in Table 9 and 10 respectively. The graphical representation of Table 12 is given in FIG. 3. FIG. 3 shows A statistically significant decrease in Kasumi-3 cell viability was observed with 10, 100 and 1000 nM Anti-CD7 antibody in presence of 13.2 nM αMFc-CL-MMAE when analysed using One-way ANOVA, followed by Dunnett's post-hoc multiple comparison test (***p<0.0001; ±SEM). The quantifications are expressed as Average (±Standard Error Mean [SEM]).

One-way ANOVA followed by post-hoc Dunnett's multiple comparisons test was performed on Table 10 data. A statistically significant decrease in Kasumi-3 viability was observed with 10, 100 and 1000 nM Anti-CD7 antibody in presence of αMFc-CL-MMAE when compared to Untreated cells (***p<0.0001).

Figure 4:
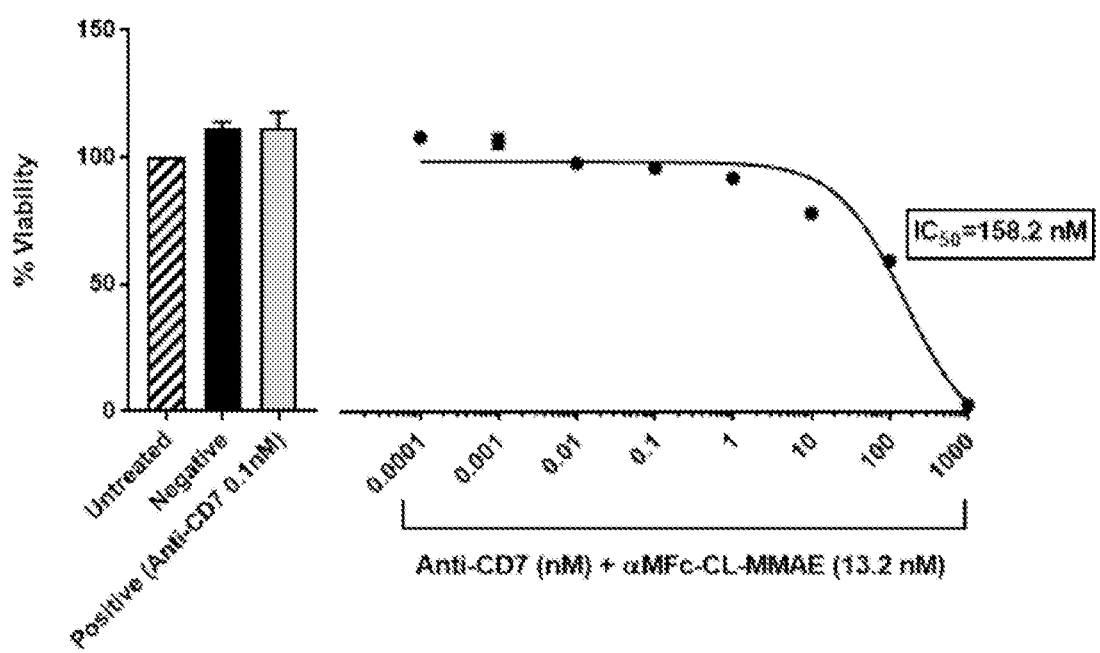
FIG. 4 is a graph showing the percentage viability of Kasumi-3 with Anti-CD7 and αMFc-CL-MMAE treatment.

The data for % Viability is given in Table 11 and graphically represented in FIG. 4.

The $IC_{50}$ of 158.2 nM was obtained from the non-linear regression curve.

4.3 Cytotoxicity Profile of Anti-CD13 Antibody to Kasumi-3 Cells

Figure 5:
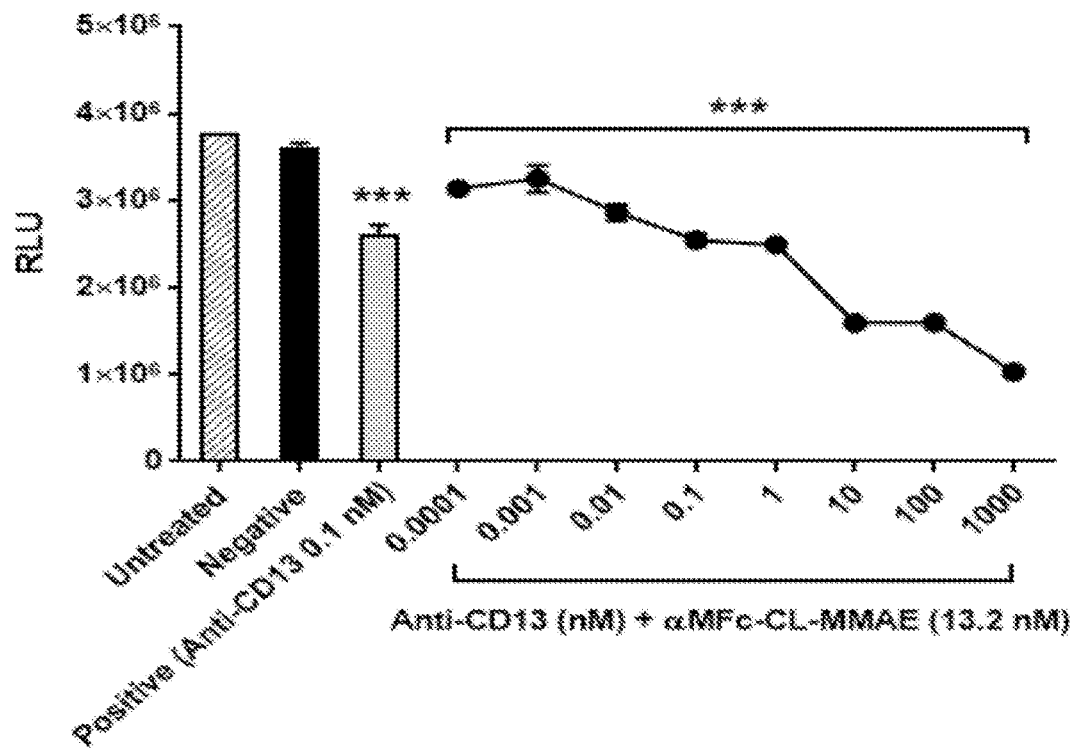
FIG. 5 is a graph showing the cytotoxic profile of Anti-CD13 in the presence of αMFc-CL-MMAE represented as RLU.

The raw data and data after Blank subtraction for the luminescence intensity for Anti-CD13 treatment are given in Table 12 and 13 respectively. The graphical representation of Table 13 is given in FIG. 5. FIG. 5 shows a statistically significant decrease in Kasumi-3 cell viability was observed with all concentrations of Anti-CD13 antibody in presence of 13.2 nM αMFc-CL-MMAE when analysed using One-way ANOVA, followed by Dunnett's post-hoc multiple comparison test (***p<0.0006; ±SEM). The quantifications are expressed as Average (±Standard Error Mean [SEM]).

One-way ANOVA followed by post-hoc Dunnett's multiple comparisons test was performed on Table 13 data. A statistically significant decrease in Kasumi-3 viability was observed with all the concentrations (0.0001-1000 nM) of Anti-CD13 antibody in presence of αMFc-CL-MMAE when compared to Untreated cells (***p<0.0006).

Figure 6:
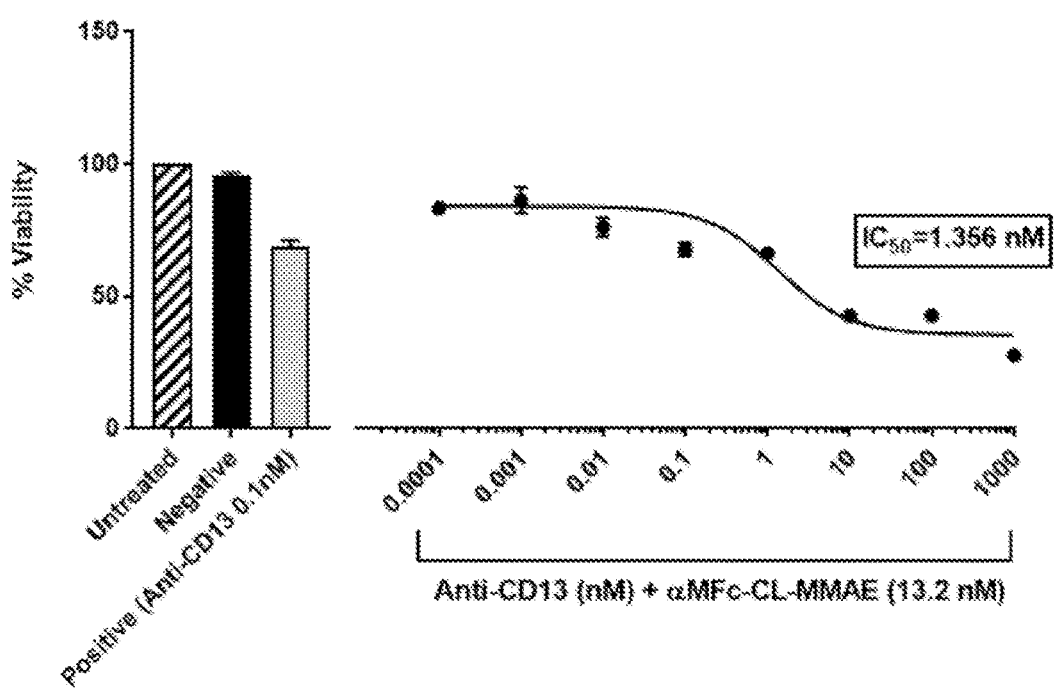
FIG. 6 is a graph showing the percentage viability of Kasumi-3 with Anti-CD13 in presence of αMFc-CL-MMAE treatment.

The data for % Viability is given in Table 14 and graphically represented in FIG. 6. FIG. 6 shows a non-liner regression curve for Anti-CD13 treatment. A $IC_{50}$=1.356 nM. was observed.

The $IC_{50}$ of 1.356 nM was obtained from the non-linear regression curve.

4.4 Cytotoxicity Profile of Anti-CD33+Anti-CD7 Antibodies to Kasumi-3 Cells

Figure 7:
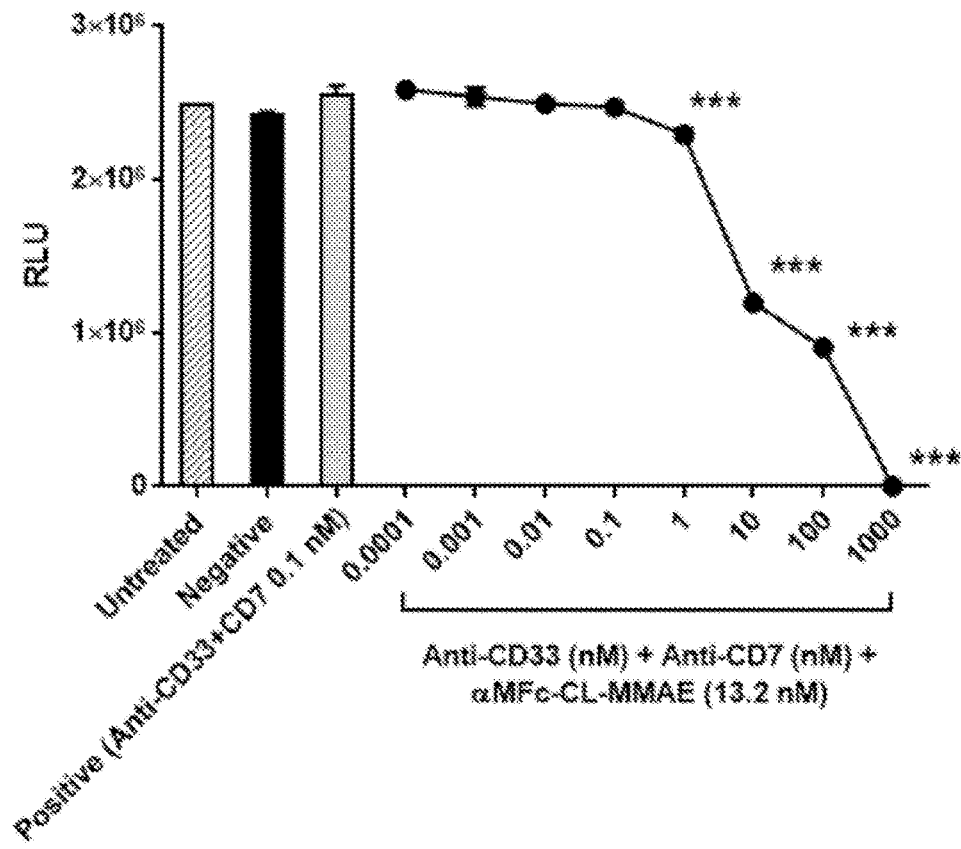
FIG. 7 is a graph showing the cytotoxic profile of Anti-CD33+Anti-CD7 in the presence of αMFc-CL-MMAE represented as RLU.

The raw data and data after Blank subtraction for the luminescence intensity for Anti-CD33+Anti-CD7 combination treatment are given in Table 15 and 16 respectively. The graphical representation of Table 16 is given in FIG. 7. FIG. 7 shows A statistically significant decrease in Kasumi-3 cell viability was observed with 1, 10, 100 and 1000 nM Anti-CD33+Anti-CD7 combination in presence of 13.2 nM αMFc-CL-MMAE when analysed using One-way ANOVA, followed by Dunnett's post-hoc multiple comparison test (***p<0.0007; ±SEM). The quantifications are expressed as Average (±Standard Error Mean [SEM]).

Figure 22:
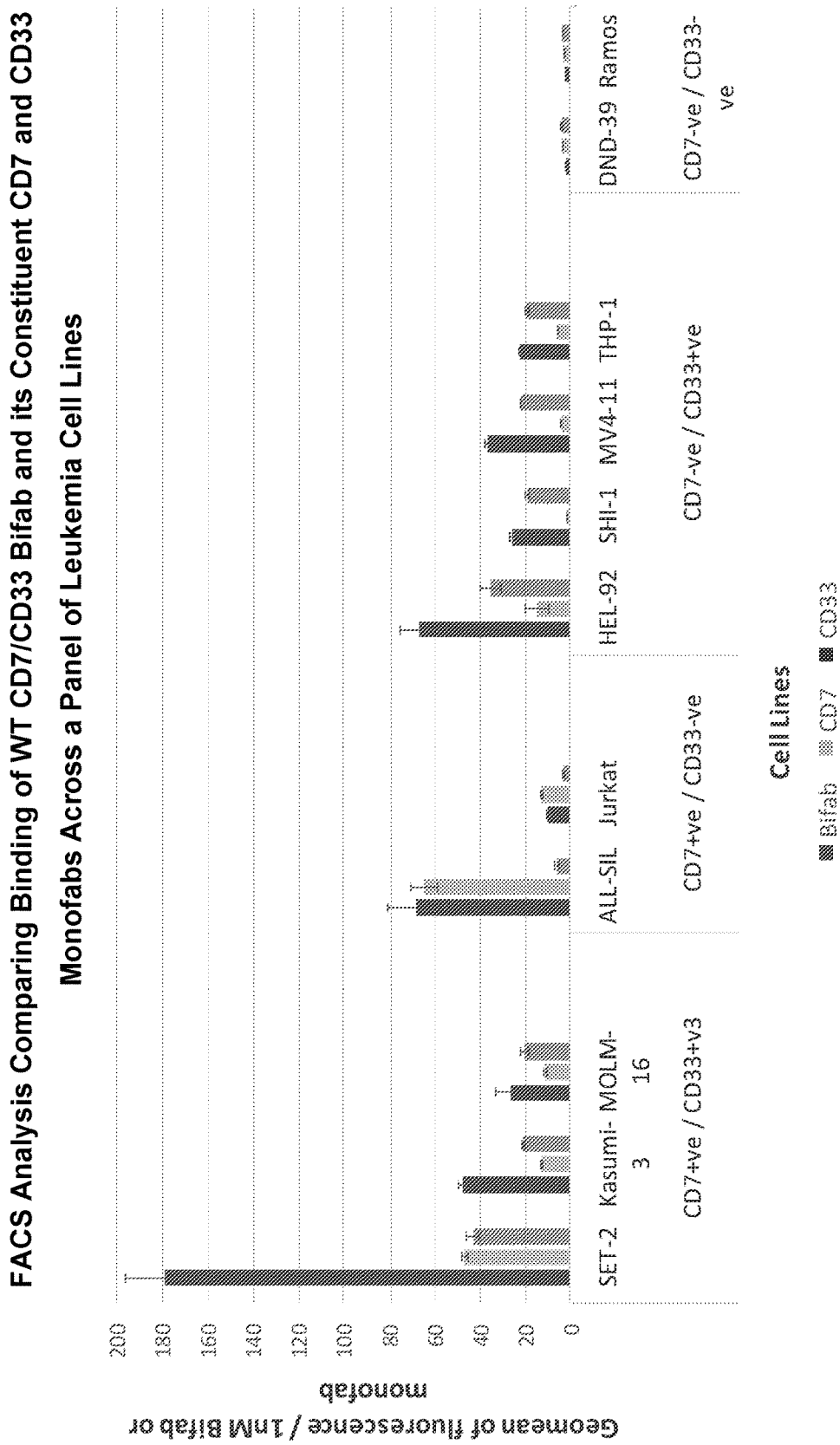
FIG. 22 is a graph representing FACS analysis comparing binding of WT CD7/CD33 Bifab and its constituent CD7 and CD33 Fabs across a panel of Leukemia cell lines, Cells were incubated with 1 nM CD7/CD33 BiFab, CD7 Fab or CD33 Fab for 1 hour at 0° C. A secondary mouse anti-Fab PE antibody was used to detect bi-Fab and Fab binding. Control samples in which cells were incubated with secondary antibody only were also included (Blank). PE labelling on the cells was detected using a FACS Calibur, BD Biosciences. Error bars show the standard deviation of duplicate repeats.

One-way ANOVA followed by post-hoc Dunnett's multiple comparisons test was performed on FIG. 22 data. A statistically significant decrease in Kasumi-3 viability was observed with concentrations above 1 nM of Anti-CD33+Anti-CD7 combination in presence of αMFc-CL-MMAE when compared to Untreated cells (***p<0.0007).

Figure 8:
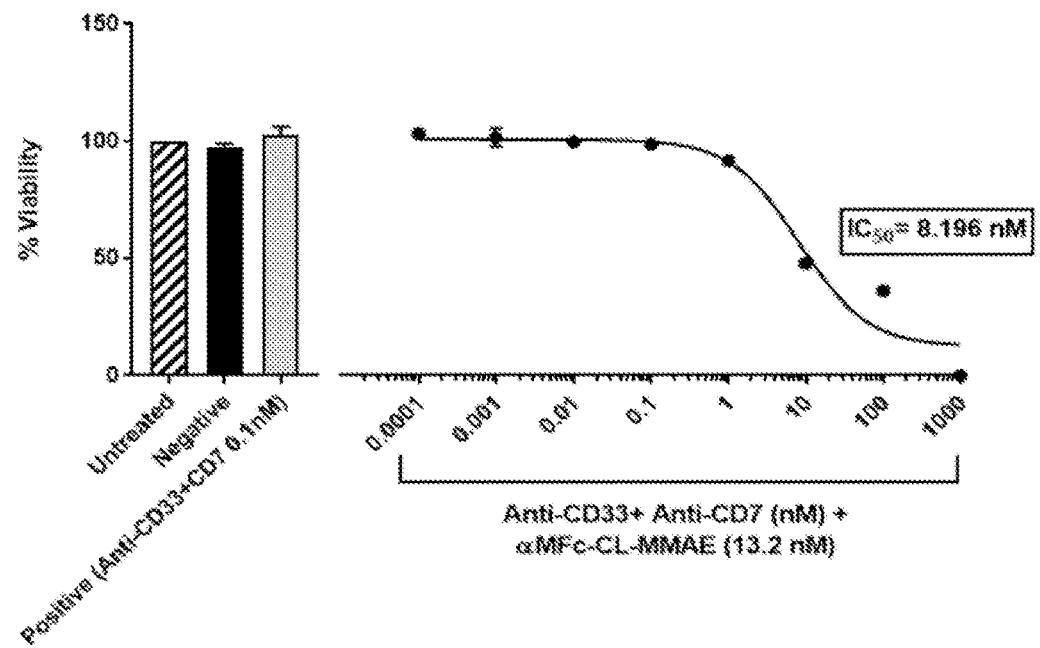
FIG. 8 is a graph showing the percentage viability of Kasumi-3 with Anti-CD33+Anti-CD7 in presence of αMFc-CL-MMAE treatment.

The data for % Viability is given in Table 17 and graphically represented in FIG. 8. FIG. 8 shows a non-liner regression curve for Anti-CD33+Anti-CD7 treatment. A $IC_{50}$=8.196 nM was observed.

The $IC_{50}$ of 8.196 nM was obtained from the non-linear regression curve.

Figure 9:
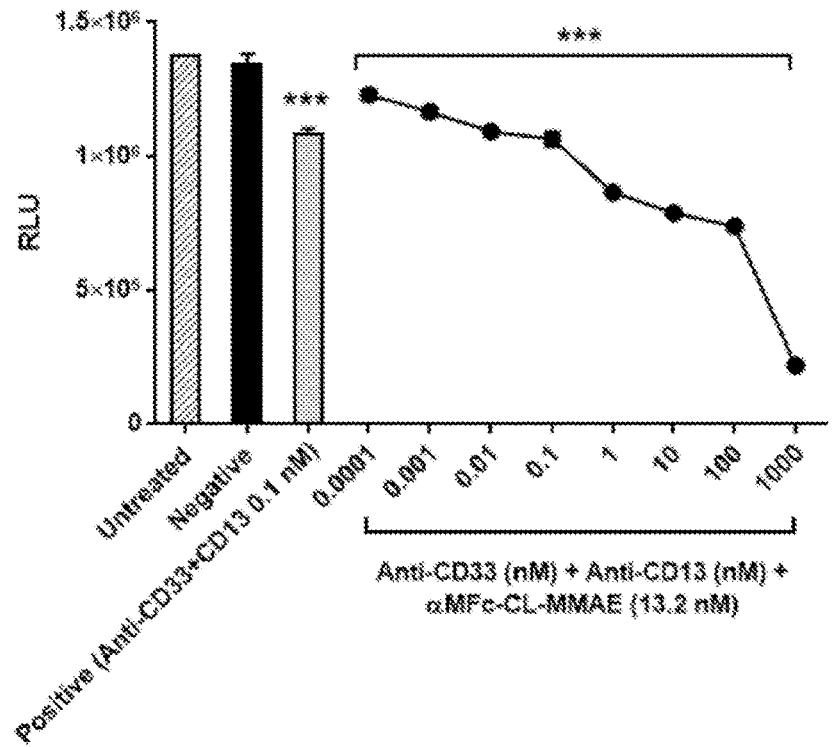
FIG. 9 is a graph showing the cytotoxic profile of Anti-CD33+Anti-CD13 in the presence of αMFc-CL-MMAE represented as RLU.

4.5 Cytotoxicity Profile of Anti-CD33+Anti-CD13 Antibodies to Kasumi-3 Cells The raw data and data after Blank subtraction for the luminescence intensity for Anti-CD33+Anti-CD13 treatment are given in Table 18 and 19 respectively. The graphical representation of Table 19 is given in FIG. 9. FIG. 9 shows a statistically significant decrease in Kasumi-3 cell viability was observed with all the concentrations of Anti-CD33+Anti-CD13 combination in presence of 13.2 nM αMFc-CL-MMAE when analysed using One-way ANOVA, followed by Dunnett's post-hoc multiple comparison test (***p<0.0001; ±SEM). The quantifications are expressed as Average (±Standard Error Mean [SEM]).

One-way ANOVA followed by post-hoc Dunnett's multiple comparisons test was performed on Table 19 data. A statistically significant decrease in Kasumi-3 viability was observed with all the concentrations of Anti-CD33+Anti-CD13 combination in presence of αMFc-CL-MMAE when compared to Untreated cells (***p<0.0001).

Figure 10:
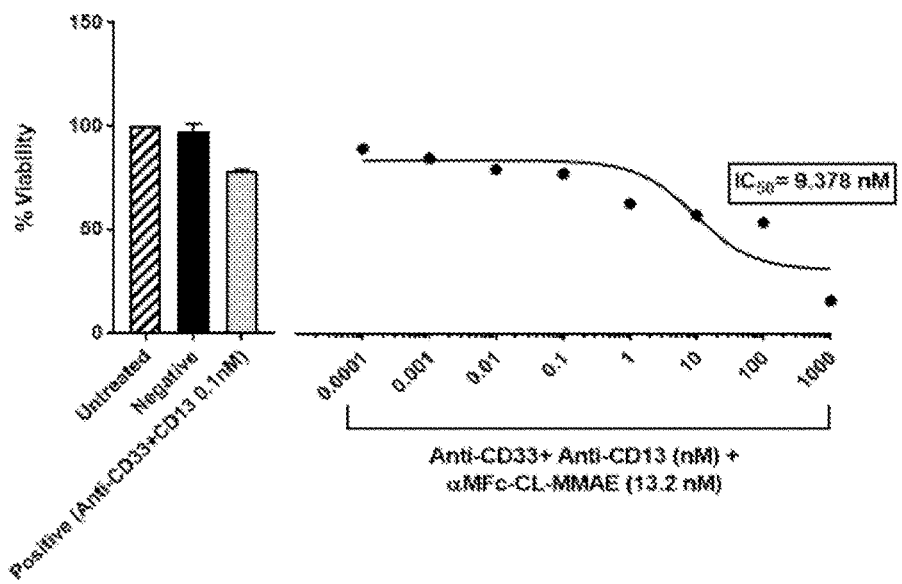
FIG. 10 is a graph showing the percentage viability of Kasumi-3 with Anti-CD33+Anti-CD13 in presence of αMFc-CL-MMAE treatment.

The data for % Viability is given in Table 20 and graphically represented in FIG. 10. FIG. 10 shows a non-liner regression curve for Anti-CD33+Anti-CD13 treatment. A $IC_{50}$=9.378 nM was observed.

The $IC_{50}$ of 9.378 nM was obtained from the non-linear regression curve.

5. Conclusion

The Kasumi-3 cells when treated with Anti-CD33 antibody in presence of αMFc-CL-MMAE showed statistically significant decrease in cell viability with 0.01, 0.1, 1, 10, 100 and 1000 nM concentrations (*<0.02; p<0.005; *<0.001). The $IC_{50}$=163.6 nM was calculated from the % Viability curve.

The Kasumi-3 cells when treated with Anti-CD7 antibody in presence of αMFc-CL-MMAE showed statistically significant decrease in cell viability with 10, 100 and 1000 nM concentrations (***p<0.0001). The $IC_{50}$=158.2 nM was calculated from the % Viability curve.

The Kasumi-3 cells when treated with Anti-CD13 antibody in presence of αMFc-CL-MMAE showed statistically significant decrease in cell viability with all the concentrations (***p<0.0006). The $IC_{50}$=1.356 nM was calculated from the % Viability curve.

The Kasumi-3 cells when treated with combination of Anti-CD33 and Anti-CD7 antibodies in presence of αMFc-CL-MMAE showed statistically significant decrease in cell viability with 1, 10, 100 and 1000 nM concentrations (***p<0.0007). The $IC_{50}$=8.196 nM was calculated from the % Viability curve.

The Kasumi-3 cells when treated with combination of Anti-CD33 and Anti-CD13 antibodies in presence of αMFc-CL-MMAE showed statistically significant decrease in cell viability with all concentrations (***p<0.0001). The $IC_{50}$=9.378 nM was calculated from the % Viability curve.

These results are summarised in Table B below:

| Cell Line | Antibody | $IC_{50}$ (nM) |
|---|---|---|
| Kasumi-3 | CD7 | 158.2 |
|  | CD13 | 1.356 |
|  | CD33 | 163.6 |
|  | CD33 + CD7 | 8.196 |
|  | CD33 + CD13 | 9.378 |

6. Summary

The Kasumi-3 cells when treated with secondary antibody-drug conjugate αMFc-CL-MMAE alone (Negative Control) showed minimal toxicity.

The primary antibody (Anti-CD7) at concentration of 0.1 nM concentration showed no toxicity to the Kasumi-3 cells. The mid-concentration of 0.1 nM of primary antibodies was selected to test as Positive Control.

However, the Anti-CD33 and Anti-CD13 antibodies without αMFc-CL-MMAE showed significant toxicity to Kasumi-3 cells at 0.1 nM concentration.

A dose dependent reduction in cell viability was observed when Kasumi-3 cells were treated with αMFc-CL-MMAE in presence of Anti-CD33, Anti-CD7, Anti-CD13 and combinations. This suggests the specificity of the primary antibody binding to the over-expressed cell surface markers.

An unexpected and synergistic reduction in cell viability was observed when Kasumi-3 cells were treated with αMFc-CL-MMAE in presence of both anti-CD7 and anti-CD33 antibodies.

Example 2: Determining the $IC_{50}$ of 3 Monoclonal Antibodies (Alone and in Combination) in the Double Antigen Cell Line HEL 92.1.7

Experimental Conditions

TABLE C

Overview of experimental conditions tested

| Cell Line | Primary Antibodies (and combinations) | Secondary Antibody | Readout |
|---|---|---|---|
| HEL 92.1.7 ATCC ® TIB-180 | CD(A) CD(D) CD(A) and CD(D) | Anti-Fc linked to toxin (MMAE) | Cell viability assay |

Note:
CD(A) = CD33; CD(D) = CD56

Number of Samples to be Tested
   3 antibodies or combinations*8 concentrations*1 cell line*3 (triplicates)=72
   Negative Control (Anti-Fc linked to MMAE)*1 concentration*1 cell line*3 (triplicates)=3
   2 Positive Control (Primary antibodies)*1 concentration*1 cell line*3 (triplicates)=6
   Control (Cells without antibody treatment)*1 cell line*3 (triplicates)=3
TOTAL=84 Tests 2. Materials i. HEL 92.1.7: ATCC® TIB-180
ii. RPMI-1640 Medium: ATCC® 30-2001™
iii. Fetal Bovine Serum (FBS): ATCC® 302020™
iv. Dulbecco's phosphate-buffered saline (DPBS): Gibco™
v. Monoclonal antibodies:
   Anti-CD33 antibody
   Anti-CD56 antibody
vi. Secondary antibody
   Anti-Mouse IgG Fc-MMAE Antibody with cleavable linker (αMFc-CL-MMAE): Moradec
vii. Non-adherent culture flasks
viii. CellTiter-Glo® Luminescent Cell Viability Assay: Promega
ix. 96 well plates (tissue grade-white)

3. Methods 3.1 Cell Culture
HEL 92.1.7 cells were maintained in suspension with complete growth media (RPMI-1640 with 10% FBS) at 37° C. in a 5% CO2 incubator. The cell density was maintained between $1\times10^5$ to $1\times10^6$ cells/ml with media change in intervals of 2-3 days.

3.2 Cytotoxicity Detection Using CellTiter-Glo® Luminescent Cell Viability Assay
i. Freshly split HEL 92.1.7 cells were seeded into 96-well white plates in culture medium at density of 5,000 cells per well in 100 μl culture media.
ii. The primary monoclonal antibody (CD33, CD56) were diluted in culture media and added to the plates to obtain the desired concentration range (0.0001 to 1000 nM).
iii. The cells were then incubated in the presence of the primary antibody for 5 to 10 minutes.
iv. In the meantime, the secondary antibody (αMFc-CL-MMAE) was diluted in culture medium. After incubation with the primary antibodies, the αMFc-CL-MMAE was added to the wells to obtain 13.2 nM per well.

v. Conditions such as Blank, Control, Negative Control and Positive Control were also included in each assay plate. See Table 21, 22 and 23 for the plate layouts for HEL 92.1.7 with Anti-CD33, Anti-CD56 and Anti-CD33+Anti-CD56 combination respectively.

Blank=Culture media only
Control=Cells with no treatment
Negative Control=Cells treated with 13.2 nM αMFc-CL-MMAE
Positive Control=Cells treated with 0.1 nM Primary Antibodies vi. The plates were incubated for 72 hours.

vii. After 72 hours of incubation the 100 μl of CellTiter-Glo Reagent was added to each well.

viii. The contents were mixed for 2 minutes on an orbital shaker to induce cell lysis and incubated at room temperature for 10 minutes.

ix. The luminescence intensity was measured using the Promega GloMax® Explorer instrument.

3.3 Data Analysis

The average reading of the Blank was subtracted from all the other readings. Blank contained only the culture medium and represented as the background for the assay plate. The data were then statistically analysed (One-way ANOVA followed by post-hoc Dunnett's multiple comparisons test) and plotted using GraphPad Prism 7.02 software. The luminescence intensity is represented as Relative Luminescence Unit (RLU) on the y-axis and the different conditions and Primary Antibody concentrations were represented on the x-axis.

The Percentage Viability (% Viability) of the cells were calculated taking Control (untreated) as 100% viable. Percentage Viability of the other cells were normalised to the Control. The data was plotted in GraphPad Prism 7.02 software using the Non-linear regression curve. The $IC_{50}$ is defined as the concentration of the relevant primary antibodies (CD33, CD56 alone or CD33+CD56 in combination) that induces 50% cytotoxic effect in the presence of the secondary antibody drug conjugate (αMFc-CL-MMAE). This was calculated using % Viability curve analysed by non-linear regression curve fit.

4. Results 4.1 Cytotoxicity Profile of Anti-CD33 Antibody to HEL 92.1.7

Figure 11:
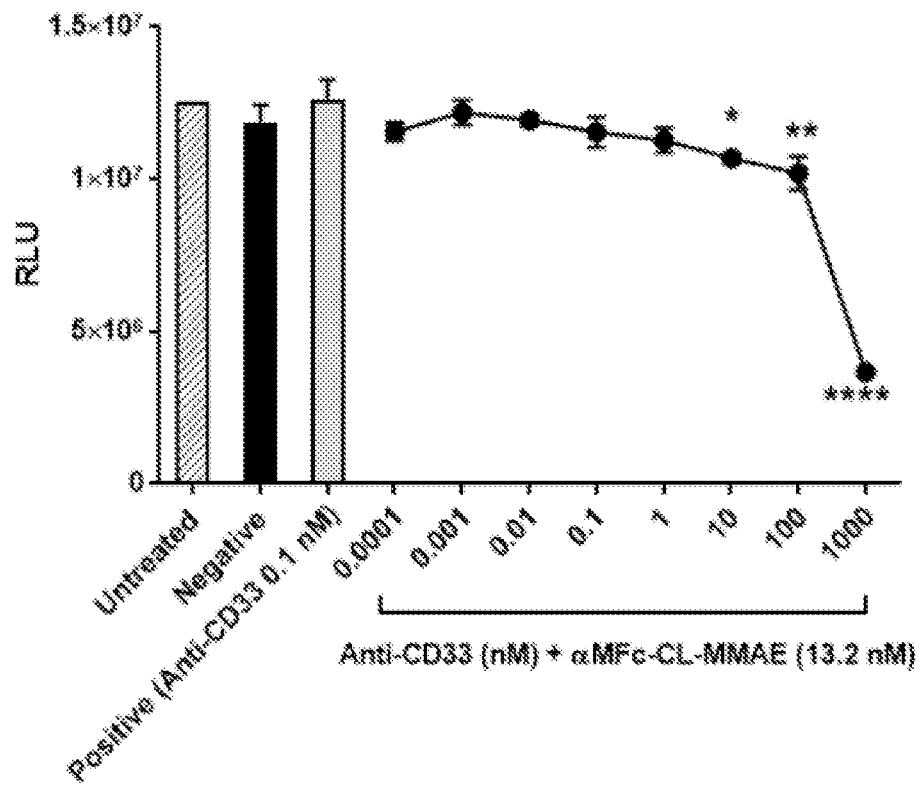
FIG. 11 is a graph showing the cytotoxic profile of Anti-CD33 in the presence of αMFc-CL-MMAE represented as RLU.

The raw data and data after Blank subtraction for the luminescence intensity for Anti-CD33 treatment are given in Table 24 and 25 respectively. The graphical representation of Table 25 is given in FIG. 11. FIG. 11 shows a statistically significant decrease in HEL 92.1.7 cell viability was observed with 10, 100 and 1000 nM Anti-CD33 antibody in presence of 13.2 nM αMFc-CL-MMAE when analysed using One-way ANOVA followed by Dunnett's post-hoc multiple comparison test (*p<0.05; p<0.01; **p<0.0001; ±SEM). The quantifications are expressed as Average (±Standard Error Mean [SEM]).

One-way ANOVA followed by post-hoc Dunnett's multiple comparisons test was performed on Table 25 data. A statistically significant decrease in HEL 92.1.7 viability was observed with 10, 100 and 1000 nM Anti-CD33 antibody in presence of αMFc-CL-MMAE when compared to Untreated cells (*p<0.05; P<0.01; **P<0.0001).

Figure 12:
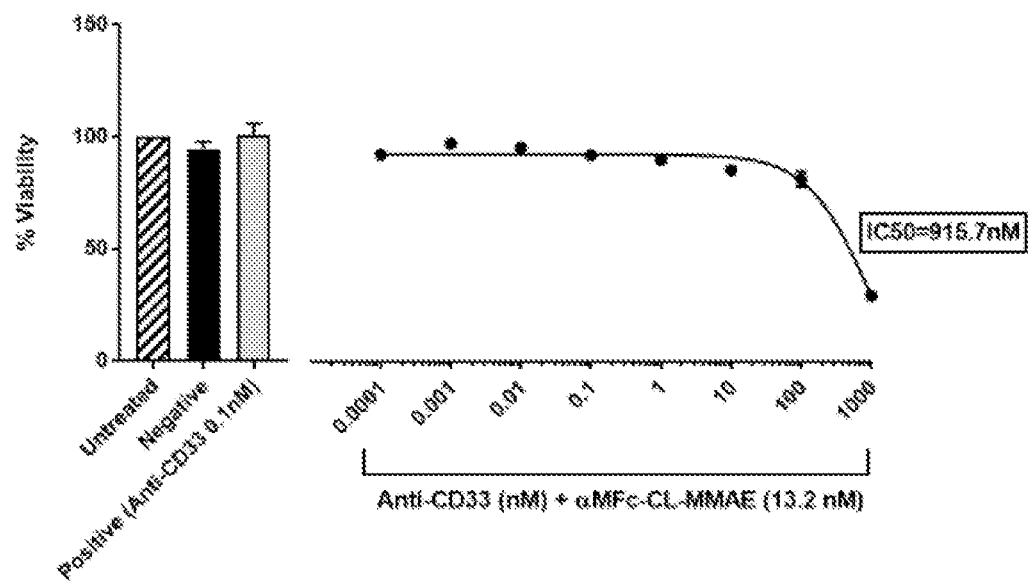
FIG. 12 is a graph showing the percentage viability of HEL 92.1.7 with Anti-CD33 and αMFc-CL-MMAE treatment.

The data for % Viability is given in Table 26 and graphically represented in FIG. 12. FIG. 12 shows a non-liner regression curve for Anti-CD33 and αMFc-CL-MMAE Treatment. A $IC_{50}$=915.7 nM was observed.

The $IC_{50}$ of 915.7 nM was obtained from the non-linear regression curve.

4.2 Cytotoxicity Profile of Anti-CD56 Antibody to HEL 92.1.7

Figure 13:
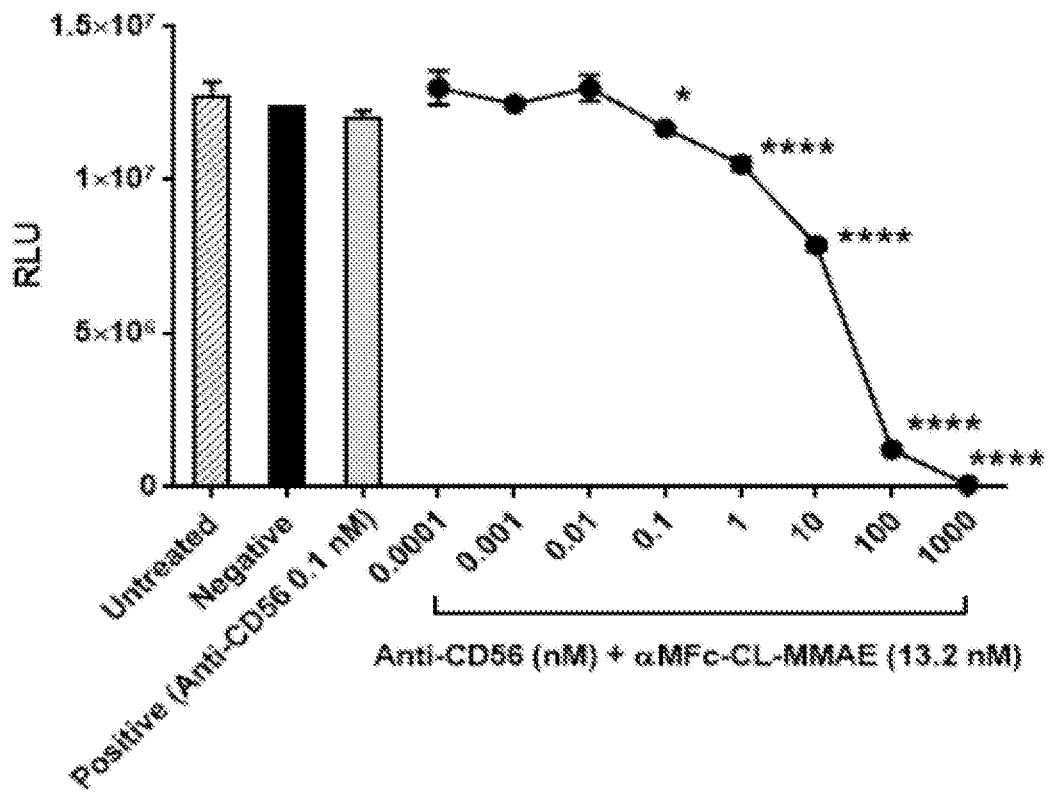
FIG. 13 is a graph showing the cytotoxic profile of Anti-CD56 in the presence of αMFc-CL-MMAE represented as RLU.

The raw data and data after blank subtraction for the luminescence intensity for Anti-CD56 treatment are given in Tables 27 and 28 respectively. The graphical representation of Table 28 is given in FIG. 13. FIG. 13 shows a statistically significant decrease in HEL 92.1.7 cell viability was observed with 0.1, 1, 10, 100 and 1000 nM Anti-CD33 antibody in presence of 13.2 nM αMFc-CL-MMAE when analysed using One-way ANOVA followed by Dunnett's post-hoc multiple comparison test (*p<0.05; ****p<0.0001; ±SEM). The quantifications are expressed as Average (±Standard Error Mean [SEM]).

One-way ANOVA followed by post-hoc Dunnett's multiple comparisons test was performed on FIG. 40 data. A statistically significant decrease in HEL 92.1.7 viability was observed with 0.1, 1, 10, 100 and 1000 nM Anti-CD56 antibody in presence of αMFc-CL-MMAE when compared to Untreated cells (*p<0.05; ****p<0.0001).

Figure 14:
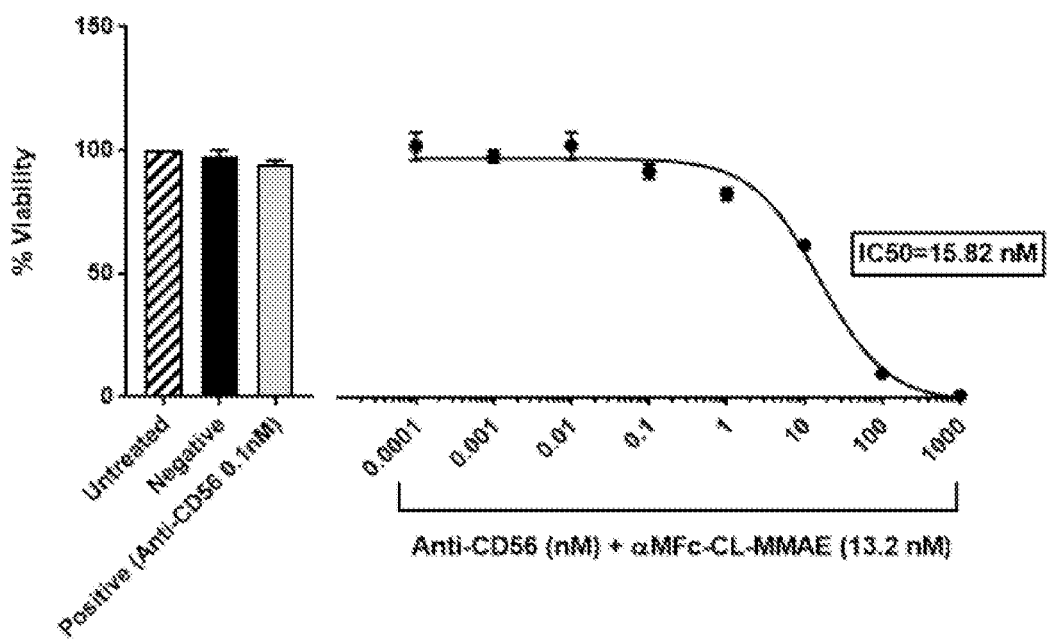
FIG. 14 is a graph showing the percentage viability of HEL 92.1.7 with Anti-CD56 and αMFc-CL-MMAE treatment.

The data for % Viability is given in Table 29 and graphically represented in FIG. 14. FIG. 14 shows a non-liner regression curve for Anti-CD56 and αMFc-CL-MMAE Treatment. A $IC_{50}$=15.82 nM was observed.

The $IC_{50}$ of 15.82 nM was obtained from the non-linear regression curve.

4.3 Cytotoxicity Profile of Anti-CD33 and Anti-CD56 Antibodies in Combination to HEL 92.1.7

Figure 15:
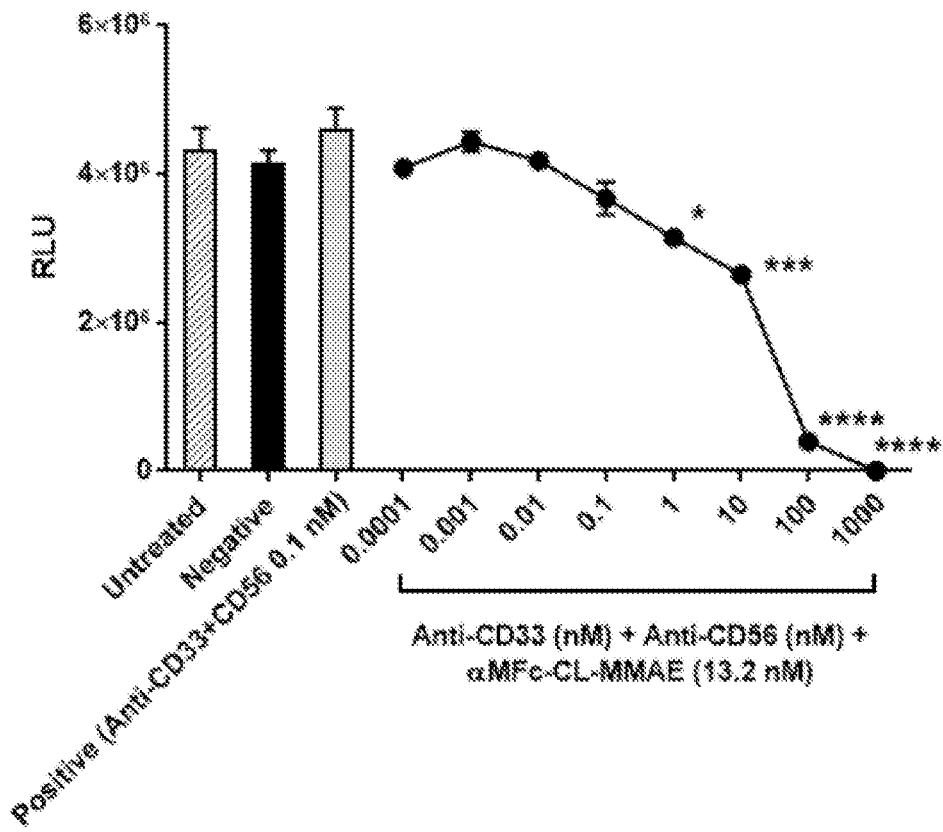
FIG. 15 is a graph showing the cytotoxic profile of Anti-CD33+Anti-CD56 combination in the presence of αMFc-CL-MMAE represented as RLU.

The raw data and data after Blank subtraction for the luminescence intensity for Anti-CD33 and Anti-CD56 combination treatment are given in Table 30 and 31 respectively. The graphical representation of Table 31 is given in FIG. 15. FIG. 15 shows a statistically significant decrease in HEL 92.1.7 cell viability was observed with 1, 10, 100 and 1000 nM Anti-CD33+Anti-CD56 antibody combinations in presence of 13.2 nM αMFc-CL-MMAE when analysed using One-way ANOVA followed by Dunnett's post-hoc multiple comparison test (*p<0.05; *p<0.001; **p<0.0001; ±SEM). The quantifications are expressed as Average (±Standard Error Mean [SEM]).

One-way ANOVA followed by post-hoc Dunnett's multiple comparisons test was performed on Table 31 data. A statistically significant decrease in HEL 92.1.7 viability was observed with 1, 10, 100 and 1000 nM Anti-CD56 antibody in presence of αMFc-CL-MMAE when compared to Untreated cells (*p<0.05; *p<0.001; **p<0.0001).

Figure 16:
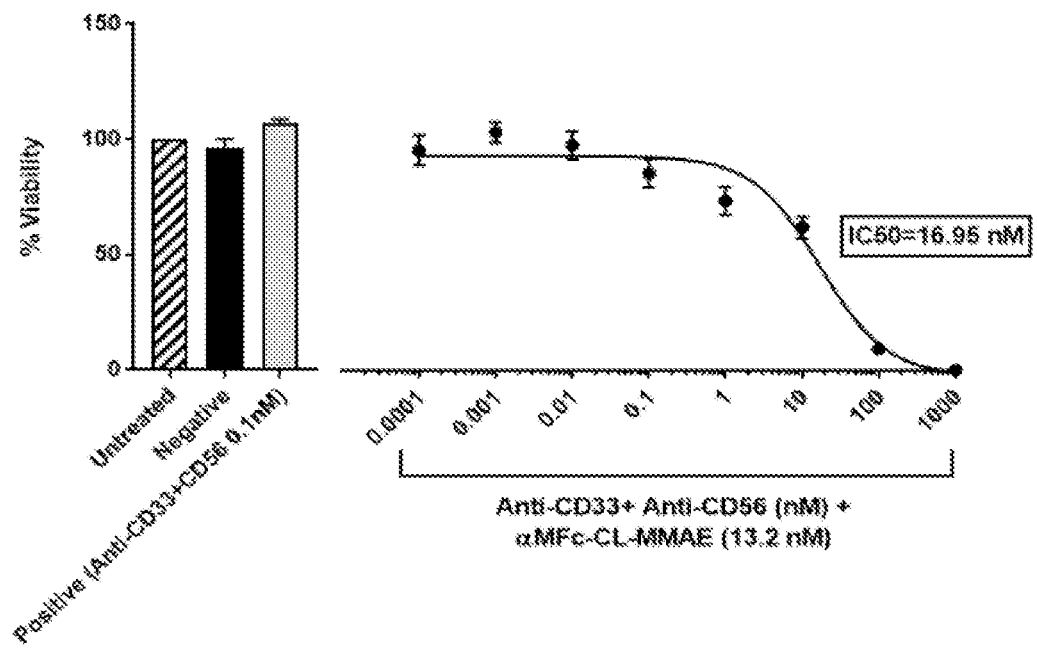
FIG. 16 is a graph showing the percentage viability of HEL 92.1.7 with Anti-CD33+ Anti-CD56 combination in presence of αMFc-CL-MMAE treatment.

The data for % Viability is given in Table 32 and graphically represented in FIG. 16. FIG. 16 shows a non-liner regression curve for Anti-CD33+Anti-CD56 combination treatment. A $IC_{50}$=16.95 nM was observed.

The $IC_{50}$ of 16.95 nM was obtained from the non-linear regression curve.

5. Conclusion

The HEL 92.1.7 cells when treated with Anti-CD33 antibody in presence of αMFc-CL-MMAE showed statistically significant decrease in cell viability with 10, 100 and 1000 nM concentrations (*p<0.05; p<0.01; **p<0.0001). The IC$_{50}$=915.7 nM was calculated from the % Viability curve.

The HEL 92.1.7 cells when treated with Anti-CD56 antibody in presence of αMFc-CL-MMAE showed statistically significant decrease in cell viability with 0.1, 1, 10, 100 and 1000 nM concentrations (*p<0.05; ****p<0.0001). The IC$_{50}$=15.82 nM was calculated from the % Viability curve.

The HEL 92.1.7 cells when treated with combination of Anti-CD33 and Anti-CD56 antibodies in presence of αMFc-CL-MMAE showed statistically significant decrease in cell viability with 1, 10, 100 and 1000 nM concentrations (*p<0.05; *p<0.001; **p<0.0001). The IC$_{50}$=16.95 nM was calculated from the % Viability curve.

These results are summarised in Table D below:

| Cell Line | Antibody | IC$_{50}$ (nM) |
|---|---|---|
| HEL-92.1.7 | CD56 | 15.82 |
|  | CD33 | 915.7 |
|  | CD33 + CD56 | 16.95 |

6. Summary

The HEL 92.1.7 cells when treated with secondary antibody-drug conjugate αMFc-CL-MMAE alone (Negative Control) showed minimal toxicity.

The primary antibodies (Anti-CD33, Anti-CD56 and combination) at concentration of 0.1 nM concentration showed no toxicity to the HEL 92.1.7 cells. The mid-concentration of 0.1 nM of primary antibodies was selected to test as Positive Control.

A dose dependent reduction in cell viability was observed when HEL 92.1.7 cells were treated with αMFc-CL-MMAE in presence of Anti-CD33, Anti-CD56 and combination primary antibodies. This suggests the specificity of the primary antibody binding to the over-expressed cell surface markers.

The HEL 92.1.7 cell line when treated with Anti-CD56 antibody in presence of αMFc-CL-MMAE showed lower IC$_{50}$ (15.82 nM) when compared to Anti-CD33 (915.7 nM) and combination (16.95 nM) treatment. This could be due to higher expression of CD56 markers on HEL 92.1.7 on the cell surface when compared to CD33 markers.

Example 3: Repeat of Secondary Cell Kill Assay Using BiFab Against Kasumi-3

An experiment was conducted so as to repeat the secondary cell kill assay using BiFab against the Kasumi-3 cell line.
Reagents

| | |
|---|---|
| KASUMI-3 cells | DSMZ ACC 714 |
| RPMI-1640 medium | Gibco, Life Technologies 21875034 |
| GlutaMAX ™ Supplement | Gibco, Life Technologies 35050061 |
| Fetal Bovine Serum. Heat inactivated. | Gibco, Life Technologies 10500064 |
| Anti-Human IgG Fab-MMAE Antibody | Moradec LLC AH-122AE |
| 96 well clear flat bottom microplates | Corning cat #3997 |
| CellTiter 96 ® AQueous One Solution Assay | Promega G3580 |
| Wild Type BiFab (WT Bifab) | ADCBio SON-150-20 7D-33N (Bi-Fab) |

Figure 17:
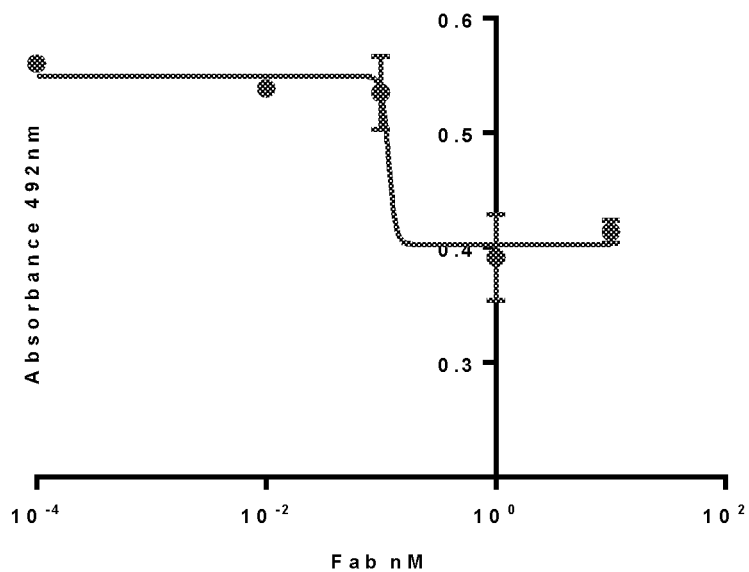
FIG. 17 is a graph showing the results of a cell kill assay conducted using a 5-point dose response of wild type BiFab and anti-human Fab-MMAE, to a concentration of 6 nM MMAE per well, on $2 \times 10^4$ cells Kasumi-3 cells per well. Cells were treated at 37° C., 5% $CO_2$ for 72 hours. Following incubation CellTiter 96 AQueous One Solution was added and the plates incubated at 37° C., 5% $CO_2$ for a further 3 hours. The absorbance was read at 492 and 690 nm. The OD 690 nm was subtracted from the OD 492 nm and the data plotted using GraphPad PRISM software. $IC_{50}$ was ~0.1169 nM. Error bars represent the standard deviation of triplicate repeats.

Growth Media
RPMI-1640 medium
10% Foetal Bovine Serum
1% GlutaMAX supplement
Method Kasumi-3 cells were harvested, counted and seeded at 2×10$^4$ cells in 100 μl growth media per well into a 96-well plate. A 5-point dose response of WT Bifab was prepared in growth media at 50 times the final assay concentration. 2 μl of WT Bifab titration was pipetted onto the seeded cells with each concentration being assayed across triplicate wells. The cells were incubated at room temperature for 10 minutes to allow the Bifab to bind. Meanwhile, Anti-Human IgG Fab-MMAE antibody was diluted in growth media to give a final assay concentration of 6 nM MMAE per well, as described in the manufactures protocol. 2 μl of diluted MMAE antibody was pipetted per well. Control wells without Bifab or MMAE conjugated antibody were included. The plates were incubated at 37° C., 5% CO$_2$ for 72 hours. Following 72 hours, CellTiter 96 AQueous One Solution was added and the plates incubated at 37° C., 5% CO$_2$ for a further 3 hours. The absorbance was read at 492 and 690 nm. The OD 690 nm was subtracted from the OD 492 nm and the data plotted using GraphPad PRISM software and shown in FIG. 17.
Results The OD 492-690 nm plotted in FIG. 17 is a measure of the viable Kasumi-3 cells remaining following 96 hours treatment of cells with a bi-Fab/anti-human Fab-MMAE complex. Increasing concentrations of bi-Fab resulted in increased cell killing reflected by a decrease in viable cells. Treatment of Kasumi-3 cells with anti-human Fab-MMAE in the absence of CD7/CD33 bi-Fab does not cause cell kill.

Conclusion

Binding of CD7/CD33 bi-Fab/anti-human Fab-MMAE complex to CD7/CD33 double antigen positive cells results in internalisation of the complex and subsequent cell killing reflected by a reduction in the number of viable cells.

Example 4: Repeat of Cell Kill Assay Using Directly Conjugated BiFab

An experiment was conducted so as to repeat cell kill assay using directly conjugated BiFab.
Reagents

| | |
|---|---|
| KASUMI-3 cells | DSMZ ACC 714 |
| RPMI-1640 medium | Gibco, Life Technologies 21875034 |
| GlutaMAX ™ Supplement | Gibco, Life Technologies 35050061 |
| Fetal Bovine Serum. Heat inactivated. | Gibco, Life Technologies 10500064 |
| Penicillin-Streptomycin (10,000 U/mL) | Gibco, Life Technologies 15140122 |
| 96 well clear flat bottom microplates | Corning cat #3997 |
| CellTiter 96 ® AQueous One Solution Assay | Promega G3580 |
| Wild Type BiFab (WT Bifab)-MMAE | ADCBio SON-150-27_BIFAB-MMAE |

Growth Media
RPMI-1640 medium
10% Foetal Bovine Serum
1% GlutaMAX supplement
1% Penicillin-Streptomycin
Method Kasumi-3 cells were harvested, counted and resuspended at $2\times10^4$ cells per 90 μl growth media. An 8-point dose response of the Bifab-MMAE was prepared in growth media at 10 times the final assay concentration. 10 μl of WT Bifab-MMAE titration was pipetted into a 96-well plate and each concentration was tested across duplicate wells. 90 μl of cells were pipetted into the wells and the plates incubated at 37° C., 5% $CO_2$ for 96 hours. Following incubation, CellTiter 96 AQueous One Solution was added and the plates incubated at 37° C., 5% $CO_2$ for a further 3 hours. The absorbance was read at 492 and 690 nm. The OD 690 nm was subtracted from the OD 492 nm and the data plotted using GraphPad PRISM software and shown in FIG. 18.

Results

Figure 18:
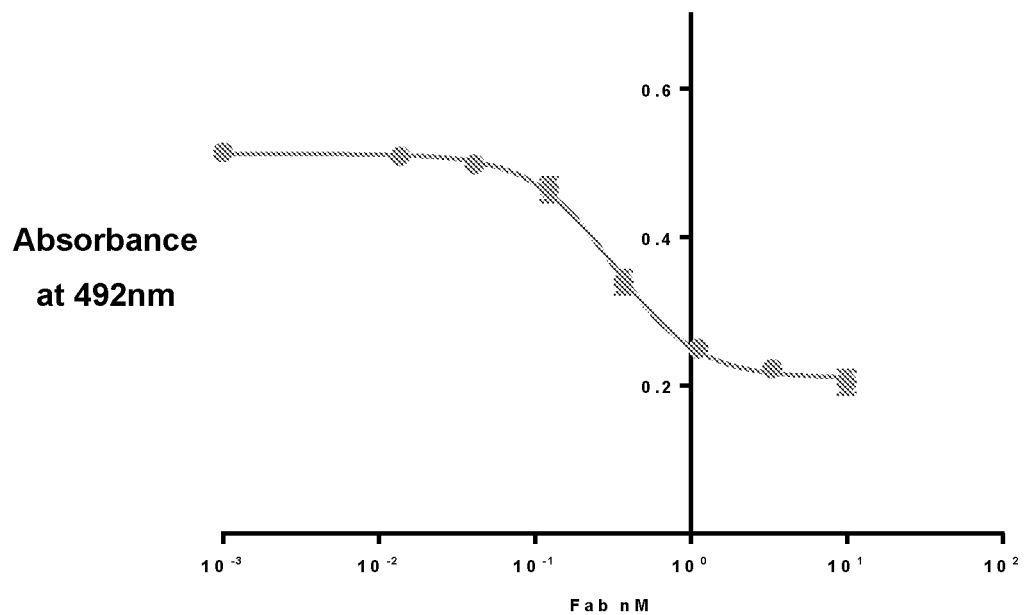
FIG. 18 is a graph showing the result of a cell kill assay conducted using an 8-point dose response of directly conjugated BiFab-MMAE on $2 \times 10^4$ Kasumi-3 cells per well. Cells were treated at 37° C., 5% $CO_2$ for 72 hours. Following incubation, CellTiter 96 AQueous One Solution was added and the plates incubated at 37° C., 5% $CO_2$ for a further 3 hours. The absorbance was read at 492 and 690 nm. The OD 690 nm was subtracted from the OD 492 nm and the data plotted using GraphPad PRISM software. $IC_{50}$ was 0.3211 nM. Error bars represent the standard deviation of duplicate repeats.

The OD 492-690 nm plotted in FIG. 18 is a measure of the viable Kasumi-3 cells remaining following 96 hours treatment of cells with anti CD7/CD33 bi-Fab-MMAE conjugate. Increasing concentrations of bi-Fab-MMAE resulted in increased cell killing reflected by a decrease in viable cells.

Conclusion

Binding of CD7/CD33 bi-Fab-MMAE to CD7/CD33 double antigen positive cells results in internalisation of the complex and subsequent cell killing reflected by a reduction in the number of viable cells.

Example 5: Repeat of Cell Kill Assay Using Commercial Antibodies and Anti-Mouse Fc-MMAE An experiment was conducted so as to repeat the cell kill assay using commercial antibodies and anti-mouse Fc-MMAE.

Reagents

| | |
|---|---|
| KASUMI-3 cells | DSMZ ACC 714 |
| SET-2 cells | DSMZ ACC 608 |
| RPMI-1640 medium | Gibco, Life Technologies 21875034 |
| GlutaMAX ™ Supplement | Gibco, Life Technologies 35050061 |
| Fetal Bovine Serum. Heat inactivated. | Gibco, Life Technologies 10500064 |
| Anti-Mouse IgG Fc-MMAE Antibody | Moradec LLC AM-102AE |
| 96 well clear flat bottom microplates | Corning cat #3997 |
| CellTiter 96 ® AQueous One Solution Assay | Promega G3580 |
| Mouse monoclonal [124-1D1] to CD7 | AbCam ab213014 |
| Mouse anti-CD33 [hP67.6 (Gemtuzumab)] | Absolute antibodies Ab00283-1.1; |

Growth Media
RPMI-1640 medium
10% Foetal Bovine Serum
1% GlutaMAX supplement
Method Kasumi-3 cells (FIG. 19) and SET-2 cells (FIG. 20) were harvested, counted and resuspended at $2\times10^4$ cells per 80 μl growth media for each cell line. A 5-point dose response of each of the CD7 and CD33 antibodies was prepared in growth media at 10 times the final assay concentration. 10 μl of antibody titration and 10 μl of growth media were pipetted into a 96-well plate, and each concentration of CD7 or CD33 antibody was tested across triplicate wells. For the antibody combinations 10 μl of both CD7 antibody and CD33 antibody, at the same concentration, were added to the wells. 80 μl of cells were pipetted into the wells and the plates and the cells were incubated at room temperature for 10 minutes to allow the antibodies to bind. Anti-Murine Fc-MMAE antibody was diluted in growth media to give a final assay concentration of 13.2 nM MMAE per well, as described in the manufactures protocol. 2 μl of diluted MMAE antibody was pipetted per well. Control wells without antibody or MMAE conjugated antibody were included. The plates were incubated at 37° C., 5% $CO_2$ for 96 hours. Following 96 hours, CellTiter 96 AQueous One Solution was and the plates incubated at 37° C., 5% $CO_2$ for a further 3 hours. The absorbance was read at 492 and 690 nm. The OD 690 nm was subtracted from the OD 492 nm and the data plotted using GraphPad PRISM software and shown in FIGS. 19 and 20.

Results

Figure 19:
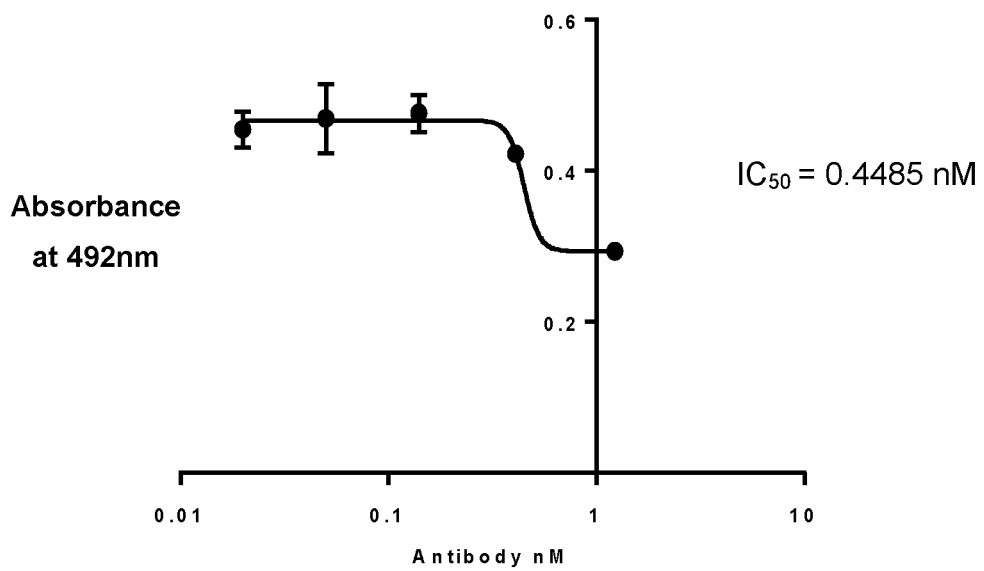
FIG. 19 are graphs showing the results of cell kill assays conducted on Kasumi-3 cells treated with a 5-point dose response of each of the CD7 and CD33 antibodies in the presence of 13.2 nM anti-Murine Fc-MMAE antibody. Control wells without antibody or MMAE conjugated antibody were included. The plates were incubated at 37° C., 5% $CO_2$ for 96 hours. Following incubation CellTiter 96 AQueous One Solution was added and the plates incubated at 37° C., 5% $CO_2$ for a further 3 hours. The absorbance was read at 492 and 690 nm. The OD 690 nm was subtracted from the OD 492 nm and the data plotted using GraphPad PRISM software. Error bars represent the standard deviation of triplicate repeats A) anti-CD7 ab213014. $IC_{50}$ was 0.4485 nM. B) anti-CD33 ab00283-1.1. $IC_{50}$ was 0.323 nM. C) anti-CD7+anti-CD33. $IC_{50}$ was 0.3661 nM.
Figure 19:
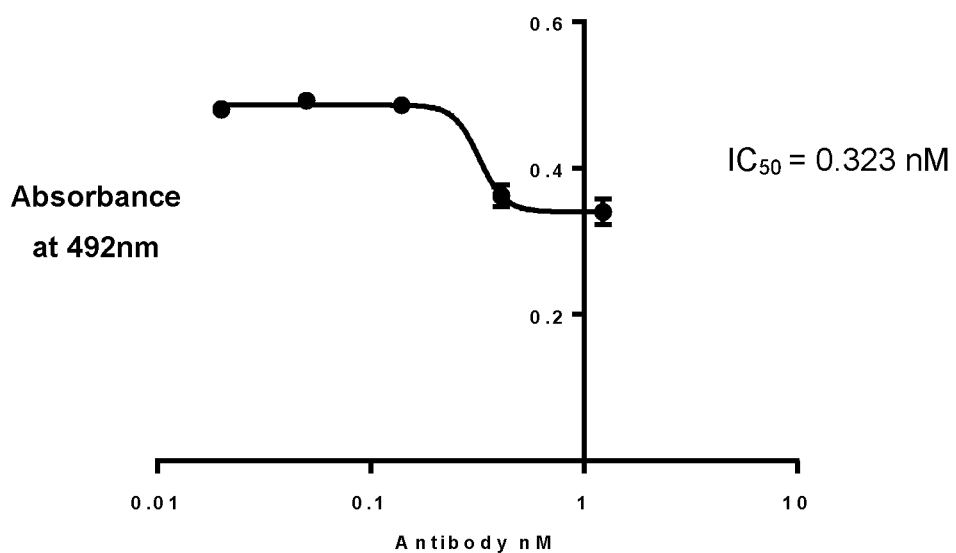
Figure 19:
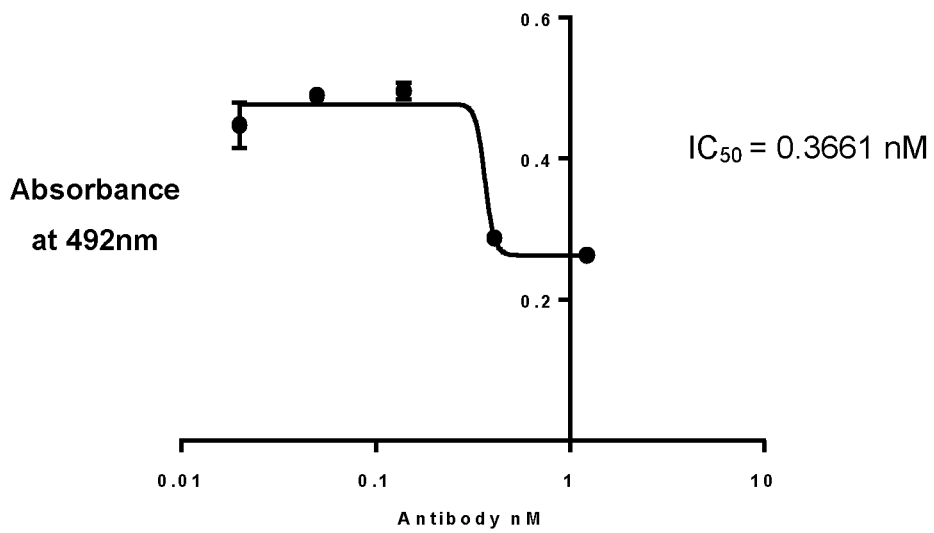
Figure 20:
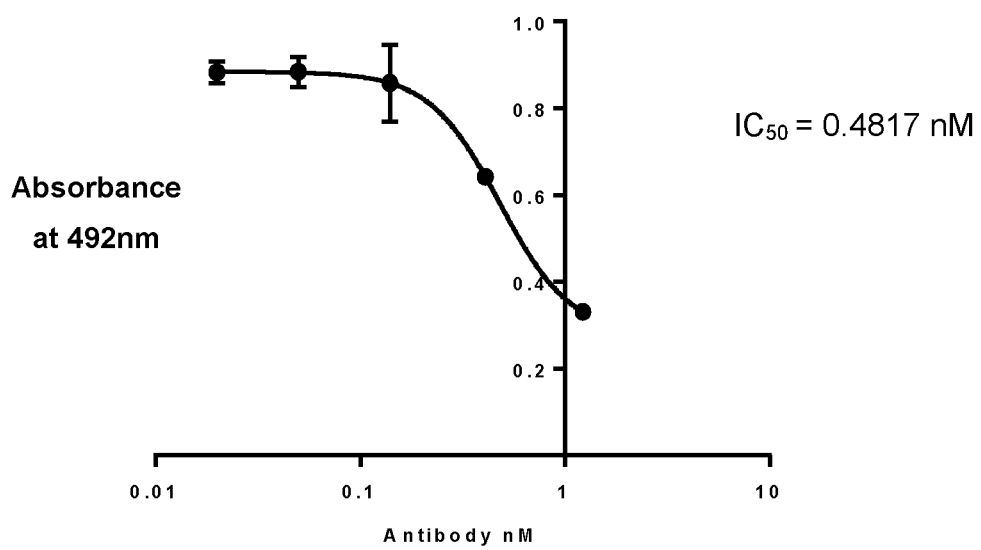
FIG. 20 are graphs showing the results of cell kill assays conducted on SET-2 cells treated with a 5-point dose response of each of the CD7 and CD33 antibodies in the presence of 13.2 nM anti-murine Fc-MMAE. Control wells without antibody or MMAE conjugated antibody were included. The plates were incubated at 37° C., 5% $CO_2$ for 96 hours. Following incubation CellTiter 96 AQueous One Solution was added and the plates incubated at 37° C., 5% $CO_2$ for a further 3 hours. The absorbance was read at 492 and 690 nm. The OD 690 nm was subtracted from the OD 492 nm and the data plotted using GraphPad PRISM software. Error bars represent the standard deviation of triplicate repeats; A) anti-CD7 ab213014. $IC_{50}$ was 0.4817 nM. B) anti-CD33 ab00283-1.1. $IC_{50}$ was non-calculatable. C) anti-CD7+anti-CD33. $IC_{50}$ was 0.206 nM.
Figure 20:
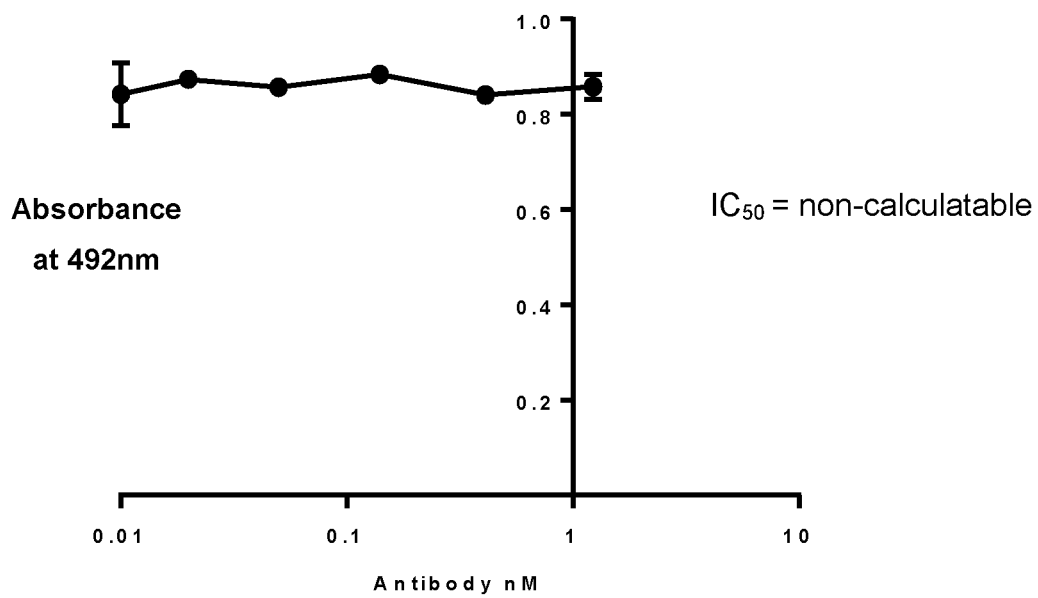
Figure 20:
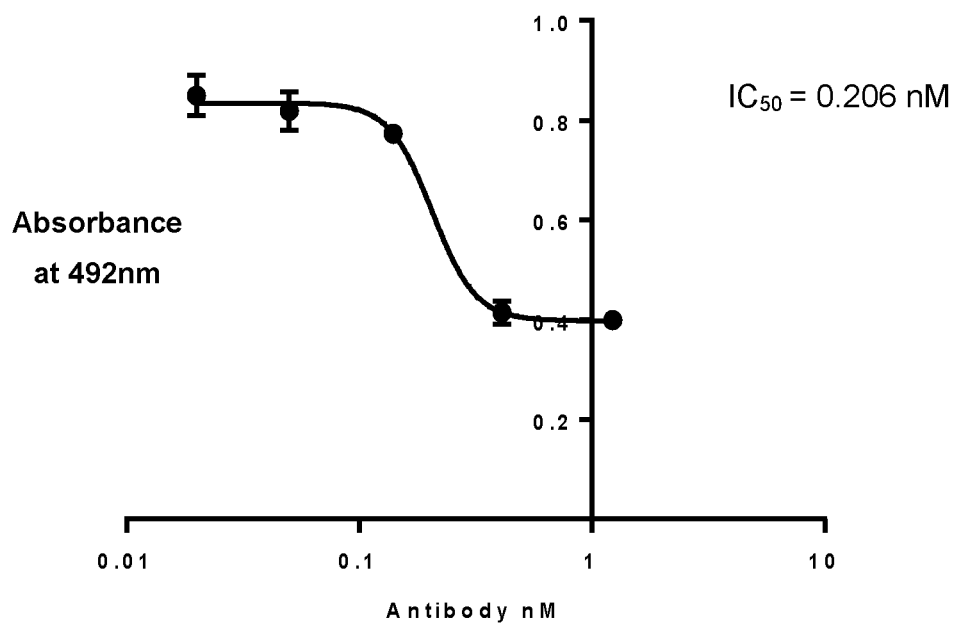

The OD 492-690 nm plotted in FIGS. 19 and 20 is a measure of the viable Kasumi-3 cells (FIG. 19) and SET-2 (FIG. 20) remaining following 96 hours treatment of cells with anti CD7 alone, anti-CD33 alone or anti-CD7+anti-CD33 antibodies, conjugated to anti-Mouse Fc-MMAE. Increasing cell kill was observed with increasing concentrations of anti-CD7 and anti-CD33/anti-mouse Fc-MMAE complexes. Anti-mouse Fc-MMAE alone did not cause any cell kill.

Conclusion

Binding of anti-CD7 and anti-CD33 antibodies complexed with anti-mouse Fc-MMAE, to double antigen positive cells results in cell kill through antigen internalisation. In the Kasumi-3 and SET-2 cells addition of both anti-CD7 and anti-CD33 antibodies resulted in more potent cell kill than adding anti-CD7 antibody alone.

Example 6: Confirmation of Whether Synergy Exists Between Targeting CD7 and CD33 in Binding Assays An experiment was conducted so as to confirm whether synergy exists between targeting CD7 and CD33 in binding assays.

Reagents

| | |
|---|---|
| Kasumi-3 cells | DSMZ ACC 714 |
| SET-2 cells | DSMZ ACC 608 |
| MOLM-16 cells | DSMZ ACC 555 |
| ALL-SIL cells | DSMZ ACC 511 |
| Jurkat cells | DSMZ ACC 282 |
| HEL-92 | DSMZ ACC 11 |
| SHI-1 | DSMZ ACC 645 |
| MV4-11 | DSMZ ACC 102 |
| THP-1 | DSMZ ACC 16 |
| DND-39 | DSMZ ACC 525 |
| Ramos | DSMZ ACC 603 |
| Dulbeccos Phosphate buffered saline (PBS) | Gibco, Life Technologies 14190144 |
| Bovine Serum Albumin (BSA)Fraction V 7.5% solution 15260037 | Gibco, Life Technologies |
| Falcon 5 mL Round Bottom Polystyrene FACS Tube | Falcon 352054 |
| Mouse anti-Human IgG Fab Secondary Antibody, PE | Invitrogen MA110377 |

| | |
|---|---|
| CD7 Monofab | SON-150-24 CD7 Fab ADCBio |
| CD7 Monofab | SON-150-24 CD33 Fab ADCBio |
| WT CD7/CD33 Bifab | SON-150-20 7D-33N (Bi-Fab) ADCBio |

Method

Kasumi-3, SET-2, MOLM-16, ALL-SIL, Jurkat, HEL-92, SHI-1, MV4-11, THP-1, DND-39 and Ramos cells were harvested and counted. $3 \times 10^6$ cells of each cell line were pelleted by centrifugation at 1000 rpm for 5 minutes. The supernatant was poured off and the cells re-suspended in 10 mls of PBS. 1 ml aliquots of the cell suspension were transferred into 5 ml FACS tubes. The tubes were capped and the cells re-pelleted by centrifugation at 1000 rpm for 5 minutes at 4° C. The supernatant was poured off and the cells resuspended in 100 μl of 1 nM WT CD7/CD33 Bifab, CD7 monofab or CD33 monofab or a combination of 1 nM of each CD7 and CD33 monofab, prepared in ice cold PBS/1% BSA. Each antibody condition was tested in duplicate. Control samples in which cells were incubated with secondary antibody only were also included. The cells were incubated on ice for one hour to allow the Fabs to bind. Following incubation unbound Fab was removed by addition of 4 ml of ice cold PBS to each FACS tube. The cells were pelleted by centrifugation at 1000 rpm for 5 minutes at 4° C. The supernatant was poured off and as much PBS removed as possible by inverting the tubes onto tissue. Meanwhile secondary mouse anti-Fab PE antibody was prepared in PBS/1% BSA to give a final concentration of 6.6 μg as described in the manufactures protocol. The cells were incubated on ice for a further 45 minutes. Excess secondary antibody was removed by washing the cells with PBS and centrifugation as described above. The supernatant was poured off and the cell pellet resuspended in 300 μl of PBS. PE labelling on the cells was detected in FL2 using a FACS Calibur, BD Biosciences. The Geomean for each fab condition was plotted and shown in FIGS. 21 and 22.

Results

Using a secondary anti-human Fab-PE antibody FACS analysis was used to detect binding of CD7/CD33 bi-Fab, CD7 Fab, CD33 Fab or CD7+CD33 Fab to leukemia cell lines. The graphs in FIGS. 21 and 22 show the Geomean of the fluorescence measured for 1 nM of each Fab arm bound to the cells.

Conclusion

Figure 21:
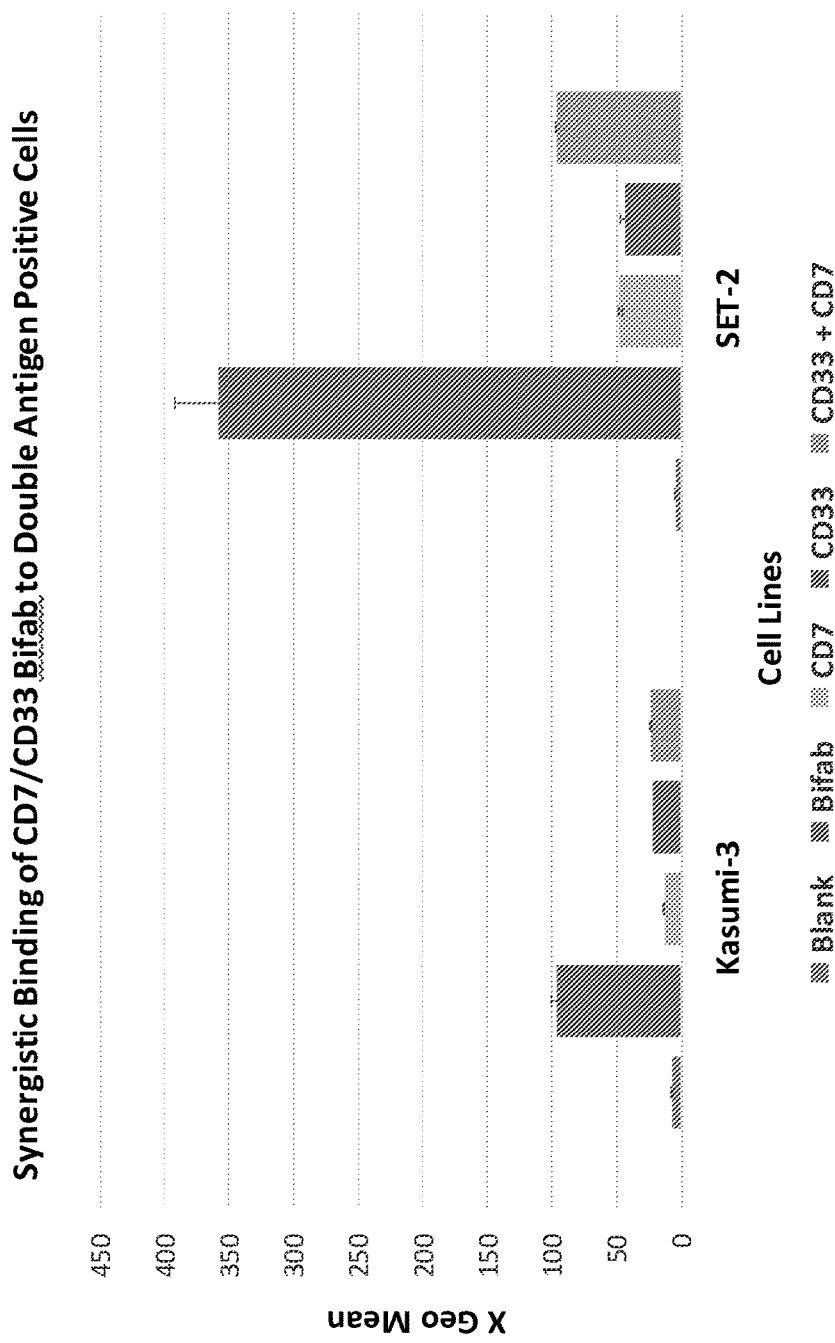
FIG. 21 is a graph representing results of Fluorescence Activated Cell Sorting (FACS) experiments investigating synergistic binding between CD7 and CD33 when targeted together with a bi-Fab compared to individually with separate Fabs. Double antigen positive cell lines, Kasumi-3 and SET-2, were treated with 1 nM CD7/CD33 BiFab, CD7 Fab, CD33 Fab or both CD7 Fab+CD33 at 0° C. for one hour. A secondary anti-Fab PE antibody was added, incubated with the cells on ice for 45 mins and the excess removed. Control samples in which cells were incubated with secondary antibody only were also included (Blank). PE labelling on the cells was detected using a FACS Calibur, BD Biosciences. Error bars show the standard deviation of duplicate repeats.

The FACS analysis shows in FIG. 21 that for double antigen positive cells lines Kasumi-3 and SET-2 that more of the bi-Fab binds to the cells than the individual Fab arms when incubated alone or in combination. In contrast the FACS data plotted in FIG. 22 indicates when the cells only express one antigen the bi-Fab binds to a similar extent as the CD7 Fab in CD7+ve/CD33−ve cells and the CD33 Fab in the CD7−ve/CD33+ve cell lines. The exceptions are the MOLM-16 and the HEL-92 cell lines which were subsequently shown to contain subpopulations of CD33 only and CD7/CD33 double positive cells.

Example 7: Cell Kill Assay: Double Antigen Positive Cell Lines Treated with CD7, CD33, CD7+CD33 and Bifab A cell kill experiment was conducted so as to assess double antigen positive cell lines treated with CD7, CD33, CD7+CD33 and Bifab.

Reagents

| | |
|---|---|
| KASUMI-3 cells | DSMZ ACC 714 |
| SET-2 cells | DSMZ ACC 608 |
| RPMI-1640 medium | Gibco, Life Technologies 21875034 |
| GlutaMAX ™ Supplement | Gibco, Life Technologies 35050061 |
| Fetal Bovine Serum. Heat inactivated. | Gibco, Life Technologies 10500064 |
| Penicillin-Streptomycin (10,000 U/mL) | Gibco, Life Technologies 15140122 |
| 96 well clear flat bottom microplates | Corning cat #3997 |
| CellTiter 96 ® AQueous One Solution Assay | Promega G3580 |
| Wild Type BiFab (WT Bifab)-MMAE Gemtuzumab-MMAE | ADCBio SON-150-27_BIFAB-MMAE |

Growth Media
RPMI-1640 medium
10% Foetal Bovine Serum
1% GlutaMAX supplement
1% Penicillin-Streptomycin Method Kasumi-3 cells and SET-2 cells were harvested, counted and resuspended at 2×104 cells per 90 μl growth media for each cell line. A 7-point dose response of the Bifab-MMAE, CD7-MMAE, CD33-MMAE, CD7-MMAE+CD33-MMAE or Gemtuzumab-MMAE were each prepared in growth media at 10 times the final assay concentration. 10 μl of each titration was pipetted separately into a 96-well plate and each concentration was tested across duplicate wells. 90 μl of cells were pipetted into the wells and the plates incubated at 37° C., 5% $CO_2$ for 96 hours. Following incubation CellTiter 96 AQueous One Solution was added and the plates incubated at 37° C., 5% CO2 for a further 3 hours. The absorbance was read at 492 and 690 nm. The OD 690 nm was subtracted from the OD 492 nm and the data plotted using GraphPad PRISM software and shown in FIGS. 23 to 25.

Results

Figure 23:
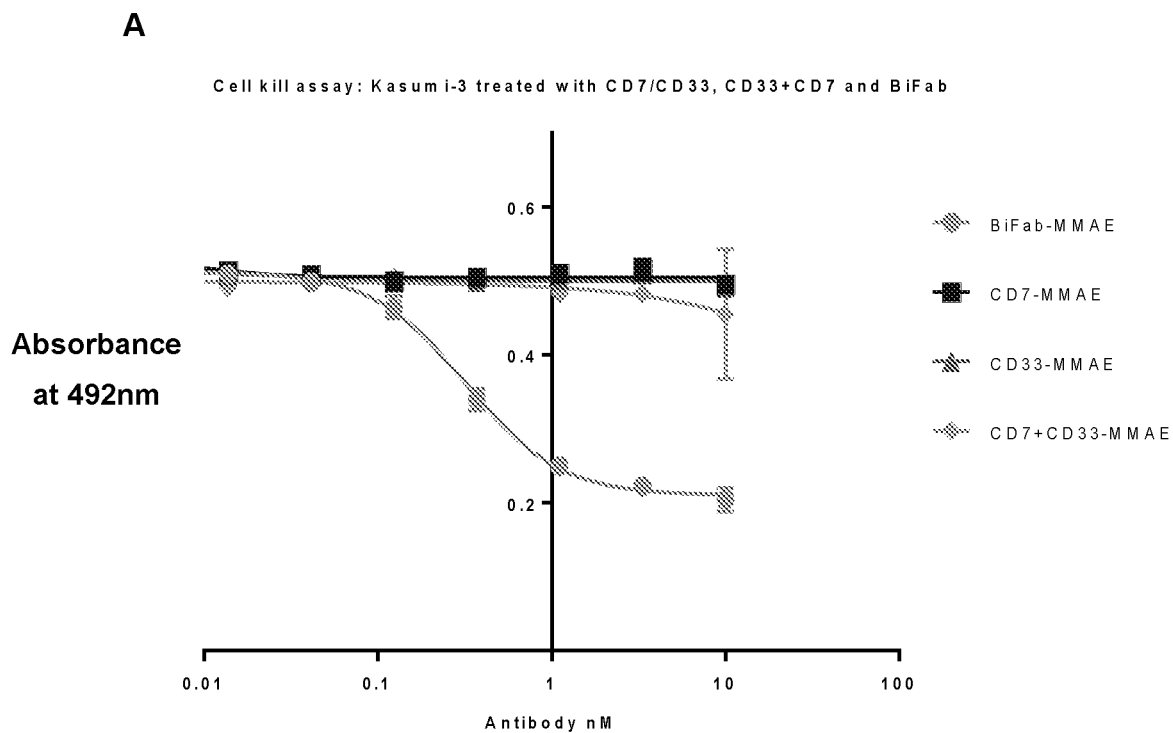
FIG. 23 are graphs showing the results of a cell kill assay conducted on A) Kasumi-3 cells and B) SET-2 cells, treated with titrations of BiFab-MMAE, CD7-MMAE, CD33-MMAE and CD7+CD33-MMAE. Cells were treated at 37° C., 5% $CO_2$ for 96 hours. Following incubation CellTiter 96 AQueous One Solution was added and the plates incubated at 37° C., 5% $CO_2$ for a further 3 hours. The absorbance was read at 492 and 690 nm. The OD 690 nm was subtracted from the OD 492 nm and the data plotted using GraphPad PRISM software. Error bars represent the standard deviation of duplicate repeats; $IC_{50}$ values for the BiFab-MMAE were: A) 0.3211 nM B) 1.453 nM
Figure 23:
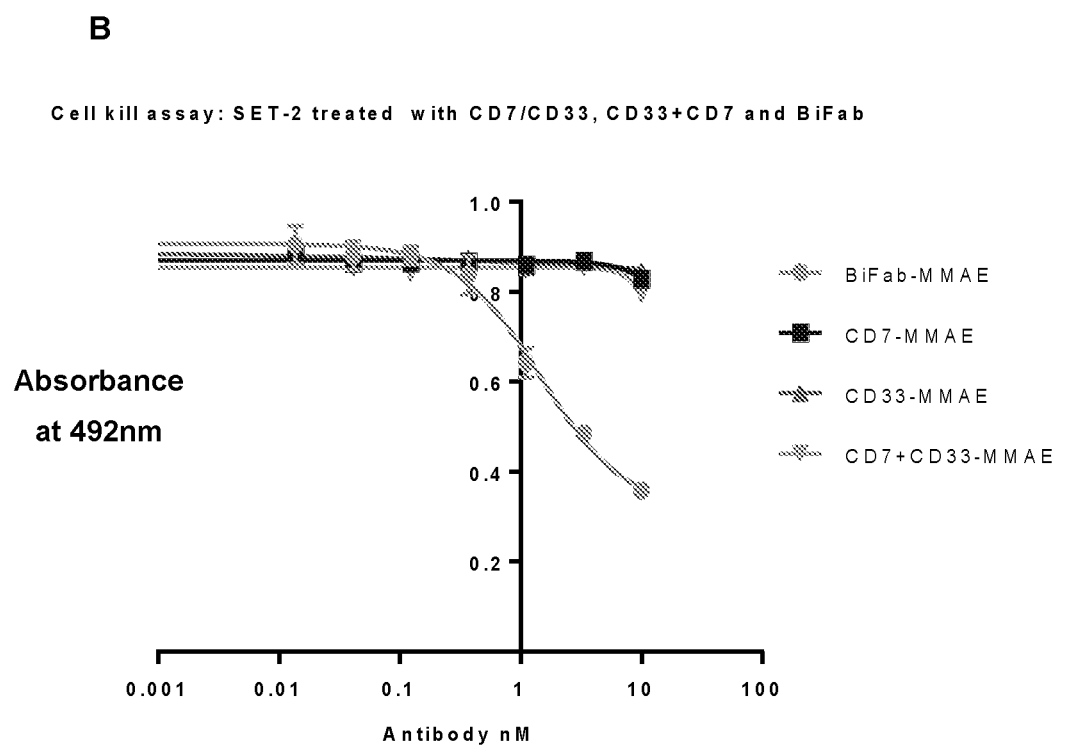
Figure 24:
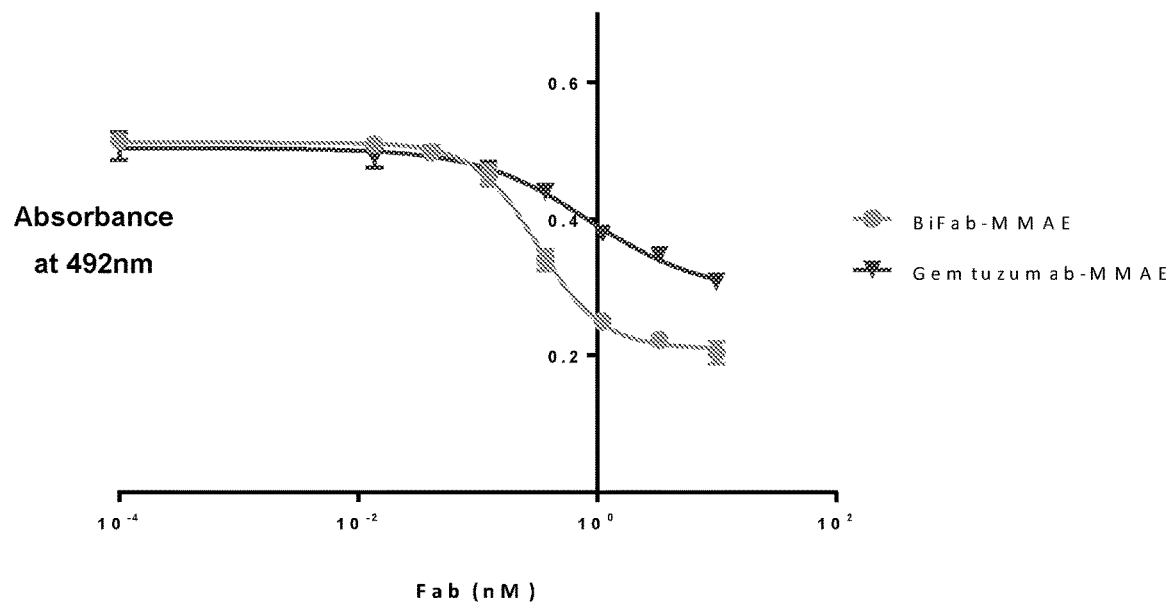
FIG. 24 is a graph showing the results of a cell kill assay conducted on Kasumi-3 cells, treated with titrations of BiFab-MMAE or Gemtuzumab-MMAE. Cells were treated at 37° C., 5% $CO_2$ for 96 hours. Following incubation CellTiter 96 AQueous One Solution was added and the plates incubated at 37° C., 5% $CO_2$ for a further 3 hours. The absorbance was read at 492 and 690 nm. The OD 690 nm was subtracted from the OD 492 nm and the data plotted using GraphPad PRISM software. Error bars represent the standard deviation of duplicate repeats; $IC_{50}$ of BiFab-MMAE was 0.3211 nM and $IC_{50}$ of Gemtuzumab-MMAE was 0.8781 nM.
Figure 25:
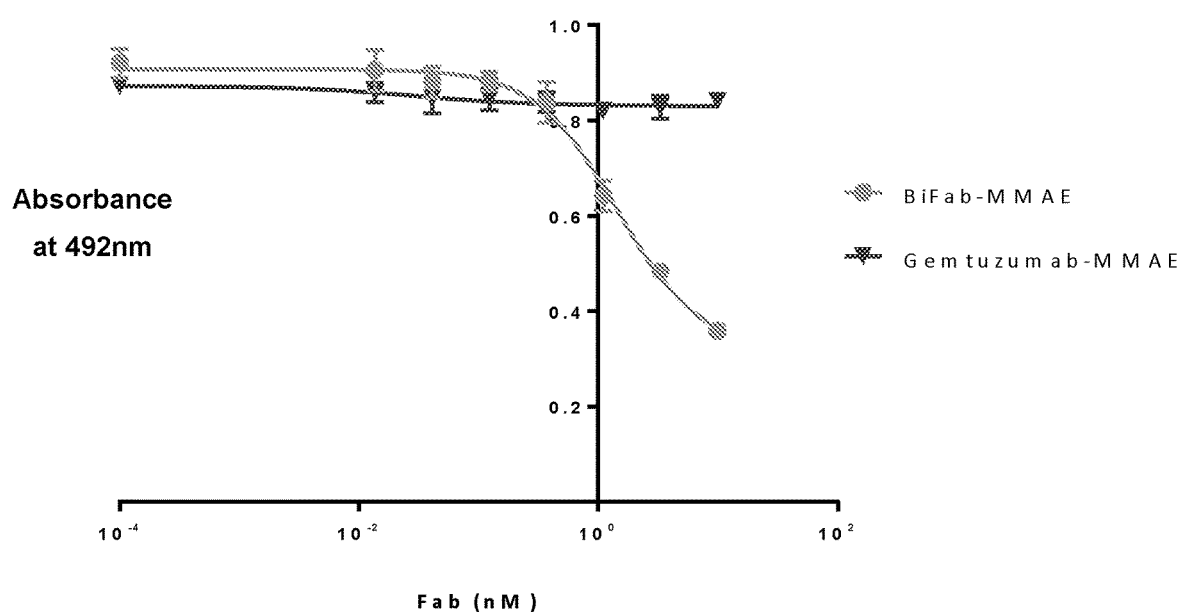
FIG. 25 is a graph showing the results of a cell kill assay conducted on SET-2 cells, treated with 10 μl of BiFab-MMAE and Gemtuzumab-MMAE. Cells were treated at 37° C., 5% $CO_2$ for 96 hours. Following incubation CellTiter 96 AQueous One Solution was pipetted per well and the plates incubated at 37° C., 5% $CO_2$ for a further 3 hours. The absorbance was read at 492 and 690 nm. The OD 690 nm was subtracted from the OD 492 nm and the data plotted using GraphPad PRISM software. Error bars represent the standard deviation of duplicate repeats; $IC_{50}$ of BiFab-MMAE was 1.453 nM and $IC_{50}$ of Gemtuzumab-MMAE was non-calculatable.

The OD 492-690 nm plotted in FIGS. 23-25 is a measure of the viable Kasumi-3 (FIGS. 23A and 24) and SET-2 (FIGS. 23B and 25) cells remaining following 96 hours treatment of cells with the indicated bi-Fab, Fab or antibody MMAE conjugates. A decrease in cell viability reflects internalisation and cell kill by the MMAE conjugate. The results for Kasumi-3 cells shows that although the CD7/CD33 biFab-MMAE and Gemtuzumab-MMAE result in potent cell kill however no cell kill at the concentrations tested was seen with the individual Fab-MMAE conjugates. The results for the SET-2 cells show that only treatment with the bi-Fab-MMAE conjugate resulted in cell kill.

Conclusion

Although previous data indicated that the individual CD7 and CD33 Fabs could bind to the Kasumi-3 and SET-2 cells no cell kill was observed with the MMAE conjugates of these Fabs. In contrast the CD7/CD33 bi-Fab causes potent cell kill in both the Kasumi-3 and SET-2 cells.

Example 7: Specific Cell Kill of CD7/CD33 Double Positive Subpopulations

A cell kill experiment was conducted so as to assess CD7/CD33 double positive subpopulations.

Reagents

| | |
|---|---|
| HEL-92 | DSMZ ACC 11 |
| MOLM-16 | DSMZ ACC 555 |
| RPMI-1640 medium | Gibco, Life Technologies 21875034 |
| GlutaMAX ™ Supplement | Gibco, Life Technologies 35050061 |
| Fetal Bovine Serum. Heat inactivated. | Gibco, Life Technologies 10500064 |
| Penicillin-Streptomycin (10,000 U/mL) | Gibco, Life Technologies 15140122 |
| Costar 24 Well Clear TC plates | SLS 3526 |
| Greiner 96 V well microplate polystyrene | SLS G651101 |
| Wild Type BiFab (WT Bifab)-MMAE | ADCBio SON-150-27_BIFAB-MMAE |
| Dulbeccos Phosphate buffered saline (PBS) | Gibco, Life Technologies 14190144 |
| Bovine Serum Albumin (BSA)Fraction V 7.5% solution | Gibco, Life Technologies 15260037 |
| Falcon 5 mL Round Bottom Polystyrene FACS Tube | Falcon 352054 |
| CD33 Monoclonal Antibody (P67.6), FITC | Thermofisher 11-0337-42 |
| CD7 Monoclonal (eBio124-1D1 (124-1D1))-PE | Thermofisher 12-0079-42 |
| Mouse anti-Human IgG Fab Secondary-PE | Thermofisher MA110377 |

Growth Media
RPMI-1640 medium
10% Foetal Bovine Serum
1% GlutaMAX supplement
1% Penicillin-Streptomycin Method HEL-92 and MOLM-16 cells were harvested and seeded into a 24 well plate at 300,000 cells per well in 1.5 ml RPMI growth media. WT bi-Fab titrations were prepared in growth media at 10× the final assay concentration, with a top final concentration of 0.3 nM. 150 µl of bi-Fab titration was pipetted per well so that both cell lines were tested with each concentration of bi-Fab. The cells were incubated at 37° C., 5% $CO_2$ for 72 hours. Following incubation the cells from each test well were harvested into and pelleted at 1000 rpm for 5 minutes at 4° C. The cells were resuspended in 300 µl of ice cold PBS/1% BSA.

Each sample was then split into 6 equal samples, approximately 50,000 cells per sample, to be analysed for binding of either anti-human Fab-PE, anti-CD7-PE, anti-CD33 FITC, anti-CD7-PE+anti-CD33 FITC or no secondary antibody. 50 µl samples were pipetted into wells of a V-bottomed 96 well plate for secondary antibody incubations and incubated on ice for 1 hour. Cells were washed 1× in ice cold PBS, pelleted and resuspended in 300 µl of PBS in a FACS tube and fluorescence analysed using the FACS Calibur, BD Biosciences. Samples were analysed for events in 2 regions representing the CD33 antigen only cells and the CD7/CD33 double antigen cells. The effect of the WT bi-Fab-MMAE on the number of events in each region was plotted and shown in FIG. 26.

Results

Figure 26:
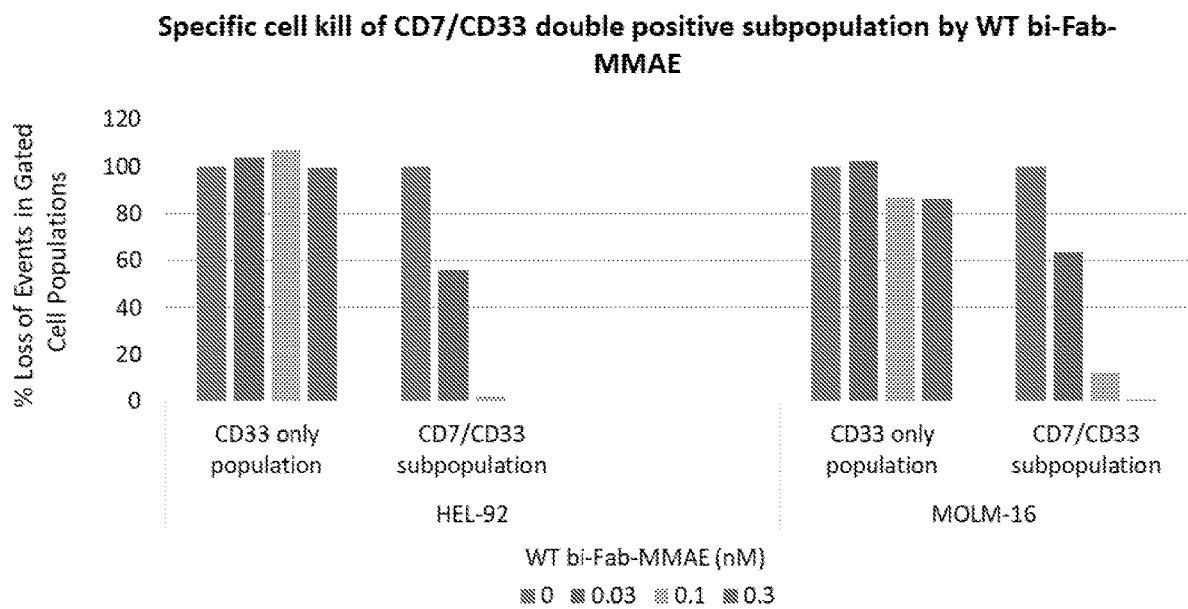
FIG. 26 are graphs showing the results of specific cell kill assays of CD7/CD33 double positive subpopulations, HEL-92 and MOLM-16 cell lines, both containing a subpopulation of CD33+/CD7+ cells, were incubated with titrations of WT biFab-MMAE at 0, 0.03, 0.1 and 0.3 nM. at 37° C., 5% $CO_2$ for 72 hours. Following incubation cells were harvested and separate samples incubated on ice for 1 hour with anti-human Fab-PE, anti-CD7-PE, anti-CD33 FITC, anti-CD7-PE+anti-CD33 FITC or no secondary antibody. Excess secondary antibody was removed and fluorescence detected using a FACS Calibur, BD Biosciences. Samples were analysed for events in 2 regions representing the CD33 antigen only cells and the CD7/CD33 double antigen cells.

FACS analysis of binding of anti-CD7-PE and anti-CD33-FITC antibodies to HEL-92 and MOLM-16 cell lines indicated that subpopulations are present within these cell lines expressing either CD7 and CD33 or CD33 only. Samples of the cell lines treated with increasing concentrations of the bi-Fab-MMAE were subsequently treated with anti-CD7-PE and anti-CD33 FITC. The CD33 only and CD7/CD33 cell subpopulations were gated and the number of cells within each gated area for each sample recorded by FACS. The percent loss of cells with increasing concentrations of bi-Fab-MMAE was calculated and the data plotted as shown in FIG. 26.

Conclusion

FACS analysis of these subpopulations following treatment of samples of the cells with CD7/CD33-biFab-MMAE indicated that the bi-Fab-MMAE can specifically kill the CD7/CD33 subpopulation only.

Example 8: Cell Kill Analysis of WT Bi-Fab-MMAE Across Further CD7/CD33 Double Positive AML Lines An experiment was conducted so as to analyse the cell kill of WT bi-Fab-MMAE across further CD7/CD33 double positive AML lines.

Reagents

| | |
|---|---|
| UOC-M1 | ACC 775 |
| HNT-34 | ACC 600 |
| RPMI-1640 medium | Gibco, Life Technologies 21875034 |
| GlutaMAX ™ Supplement | Gibco, Life Technologies 35050061 |
| Fetal Bovine Serum. Heat inactivated. | Gibco, Life Technologies 10500064 |
| Penicillin-Streptomycin (10,000 U/mL) | Gibco, Life Technologies 15140122 |
| 96 well clear flat bottom microplates | Corning cat #3997 |
| CellTiter 96 ® AQueous One Solution Assay | Promega G3580 |
| Wild Type BiFab (WT Bifab)-MMAE | ADCBio SON-150-27_BIFAB-MMAE |

Growth Media
RPMI-1640 medium
10% Foetal Bovine Serum
1% GlutaMAX supplement
1% Penicillin-Streptomycin Method UOC-M1 and HNT-34 cells were harvested, counted and resuspended at $2×10^4$ cells per 90 µl growth media. An 8 point dose response of the Bifab-MMAE was prepared in growth media at 10 times the final assay concentration. 10 µl of WT Bifab-MMAE titration was pipetted into a 96 well plate so that each concentration was tested across duplicate wells. 90 µl of cells were pipetted into the wells and the plates incubated at 37° C., 5% $CO_2$ for 96 hours.

Figure 27:
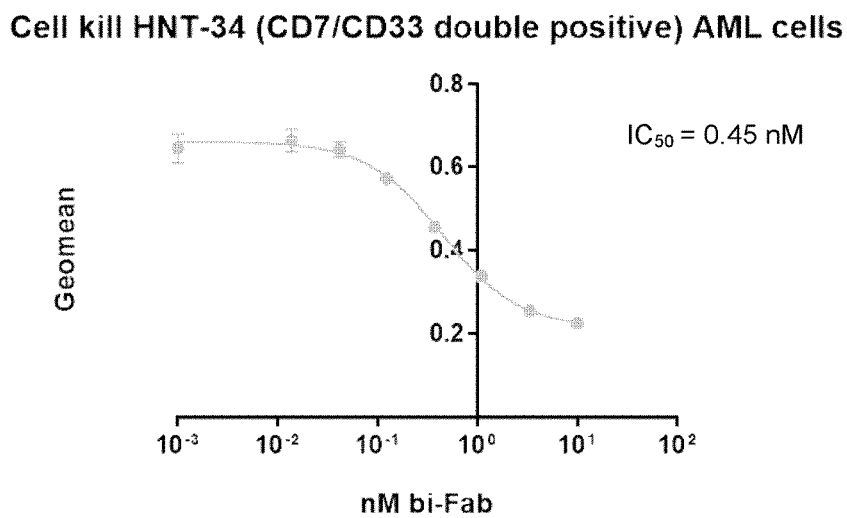
FIG. 27 is a graph showing the results of a cell kill assay conducted on HNT-34 cells, treated with titrations of BiFab-MMAE. Cells were treated at 37° C., 5% $CO_2$ for 96 hours. Following incubation CellTiter 96 AQueous One Solution was added and the plates incubated at 37° C., 5% $CO_2$ for a further 3 hours. The absorbance was read at 492 and 690 nm. The OD 690 nm was subtracted from the OD 492 nm and the data plotted using GraphPad PRISM software. Error bars represent the standard deviation of duplicate repeats. $IC_{50}$ of BiFab-MMAE was 0.45 nM.
Figure 28:
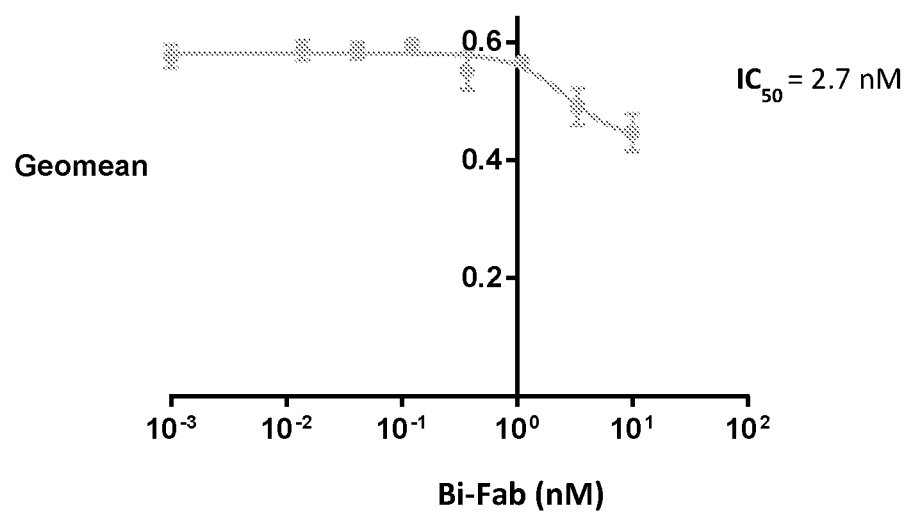
FIG. 28 is a graph showing the results of a cell kill assay conducted on UOC-M1 cells, treated with titrations of BiFab-MMAE. Cells were treated at 37° C., 5% $CO_2$ for 96 hours. Following incubation CellTiter 96 AQueous One Solution was added and the plates incubated at 37° C., 5% $CO_2$ for a further 3 hours. The absorbance was read at 492 and 690 nm. The OD 690 nm was subtracted from the OD 492 nm and the data plotted using GraphPad PRISM software. Error bars represent the standard deviation of duplicate repeats. $IC_{50}$ of BiFab-MMAE was 2.7 nM.

Following 96 hours incubation 10 µl of CellTiter 96 AQueous One Solution was pipetted per well and the plates incubated at 37° C., 5% $CO_2$ for a further 3 hours. The absorbance was read at 492 and 690 nm. The OD 690 nm was subtracted from the OD 492 nm and the data plotted using GraphPad PRISM software and shown in FIGS. 27 and 28.

Results

The OD 492-690 nm plotted in FIG. 18 is a measure of the viable HNT-34 (FIG. 27) and UOC-M1 (FIG. 28) cells remaining following 96 hours treatment of cells with anti CD7/CD33 bi-Fab-MMAE conjugate. Increasing concentrations of bi-Fab-MMAE resulted in increased cell killing reflected by a decrease in viable cells.

Conclusion

Binding of CD7/CD33 bi-Fab-MMAE to CD7/CD33 double antigen positive cells results in internalisation of the complex and subsequent cell killing reflected by a reduction in the number of viable cells.

The forgoing embodiments are not intended to limit the scope of the protection afforded by the claims, but rather to describe examples of how the invention may be put into practice.

Data Tables

|   | 1 | 2 | 3 | 4 | 5 | 6 | 7 | 8 | 9 | 10 | 11 | 12 |
|---|---|---|---|---|---|---|---|---|---|---|---|---|
| A | Blank | Control | Negative Control | Positive Control 0.1 nM (CD33) | 0.0001 nM CD33 | 0.001 nM CD33 | 0.01 nM CD33 | 0.1 nM CD33 | 1 nM CD33 | 10 nM CD33 | 100 nM CD33 | 1000 nM CD33 |
| B | Blank | Control | Negative Control | Positive Control 0.1 nM (CD33) | 0.0001 nM CD33 | 0.001 nM CD33 | 0.01 nM CD33 | 0.1 nM CD33 | 1 nM CD33 | 10 nM CD33 | 100 nM CD33 | 1000 nM CD33 |
| C | Blank | Control | Negative Control | Positive Control 0.1 nM (CD33) | 0.0001 nM CD33 | 0.001 nM CD33 | 0.01 nM CD33 | 0.1 nM CD33 | 1 nM CD33 | 10 nM CD33 | 100 nM CD33 | 1000 nM CD33 |
| D | | | | | | | | | | | | |
| E | | | | | | | | | | | | |
| F | | | | | | | | | | | | |
| G | | | | | | | | | | | | |
| H | | | | | | | | | | | | |

Table 1 shows the plate layout for the Kasumi-3 Cell Line treated with Anti-CD33 in presence of αMFc-CL-MMAE.

|   | 1 | 2 | 3 | 4 | 5 | 6 | 7 | 8 | 9 | 10 | 11 | 12 |
|---|---|---|---|---|---|---|---|---|---|---|---|---|
| A | Blank | Control | Negative Control | Positive Control 0.1 nM (CD7) | 0.0001 nM CD7 | 0.001 nM CD7 | 0.01 nM CD7 | 0.1 nM CD7 | 1 nM CD7 | 10 nM CD7 | 100 nM CD7 | 1000 nM CD7 |
| B | Blank | Control | Negative Control | Positive Control 0.1 nM (CD7) | 0.0001 nM CD7 | 0.001 nM CD7 | 0.01 nM CD7 | 0.1 nM CD7 | 1 nM CD7 | 10 nM CD7 | 100 nM CD7 | 1000 nM CD7 |
| C | Blank | Control | Negative Control | Positive Control 0.1 nM (CD7) | 0.0001 nM CD7 | 0.001 nM CD7 | 0.01 nM CD7 | 0.1 nM CD7 | 1 nM CD7 | 10 nM CD7 | 100 nM CD7 | 1000 nM CD7 |
| D | | | | | | | | | | | | |
| E | | | | | | | | | | | | |
| F | | | | | | | | | | | | |
| G | | | | | | | | | | | | |
| H | | | | | | | | | | | | |

Table 2 shows the plate layout for the Kasumi-3 Cell Line treated with Anti-CD7 in presence of αMFc-CL-MMAE.

|   | 1 | 2 | 3 | 4 | 5 | 6 | 7 | 8 | 9 | 10 | 11 | 12 |
|---|---|---|---|---|---|---|---|---|---|---|---|---|
| A | Blank | Control | Negative Control | Positive Control 0.1 nM (CD13) | 0.0001 nM CD13 | 0.001 nM CD13 | 0.01 nM CD13 | 0.1 nM CD13 | 1 nM CD13 | 10 nM CD13 | 100 nM CD13 | 1000 nM CD13 |
| B | Blank | Control | Negative Control | Positive Control 0.1 nM (CD13) | 0.0001 nM CD13 | 0.001 nM CD13 | 0.01 nM CD13 | 0.1 nM CD13 | 1 nM CD13 | 10 nM CD13 | 100 nM CD13 | 1000 nM CD13 |
| C | Blank | Control | Negative Control | Positive Control 0.1 nM (CD13) | 0.0001 nM CD13 | 0.001 nM CD13 | 0.01 nM CD13 | 0.1 nM CD13 | 1 nM CD13 | 10 nM CD13 | 100 nM CD13 | 1000 nM CD13 |
| D | | | | | | | | | | | | |
| E | | | | | | | | | | | | |
| F | | | | | | | | | | | | |
| G | | | | | | | | | | | | |
| H | | | | | | | | | | | | |

Table 3 shows the plate layout for the Kasumi-3 Cell Line treated with Anti-CD13 in presence of αMFc-CL-MMAE.

|   | 1 | 2 | 3 | 4 | 5 | 6 | 7 | 8 | 9 | 10 | 11 | 12 |
|---|---|---|---|---|---|---|---|---|---|----|----|----|
| A | Blank | Control | Negative Control | Positive Control 0.1 nM (CD33 + CD7) | 0.0001 nM CD33 + CD7 | 0.001 nM CD33 + CD7 | 0.01 nM CD33 + CD7 | 0.1 nM CD33 + CD7 | 1 nM CD33 + CD7 | 10 nM CD33 + CD7 | 100 nM CD33 + CD7 | 1000 nM CD33 + CD7 |
| B | Blank | Control | Negative Control | Positive Control 0.1 nM (CD33 + CD7) | 0.0001 nM CD33 + CD7 | 0.001 nM CD33 + CD7 | 0.01 nM CD33 + CD7 | 0.1 nM CD33 + CD7 | 1 nM CD33 + CD7 | 10 nM CD33 + CD7 | 100 nM CD33 + CD7 | 1000 nM CD33 + CD7 |
| C | Blank | Control | Negative Control | Positive Control 0.1 nM (CD33 + CD7) | 0.0001 nM CD33 + CD7 | 0.001 nM CD33 + CD7 | 0.01 nM CD33 + CD7 | 0.1 nM CD33 + CD7 | 1 nM CD33 + CD7 | 10 nM CD33 + CD7 | 100 nM CD33 + CD7 | 1000 nM CD33 + CD7 |
| D | | | | | | | | | | | | |
| E | | | | | | | | | | | | |
| F | | | | | | | | | | | | |
| G | | | | | | | | | | | | |
| H | | | | | | | | | | | | |

Table 4 shows the plate layout for the Kasumi-3 Cell Line treated with Anti-CD33+Anti-CD7 combination in presence of αMFc-CL-MMAE.

|   | 1 | 2 | 3 | 4 | 5 | 6 | 7 | 8 | 9 | 10 | 11 | 12 |
|---|---|---|---|---|---|---|---|---|---|----|----|----|
| A | Blank | Control | Negative Control | Positive Control 0.1 nM (CD33 + CD13) | 0.0001 nM CD33 + CD13 | 0.001 nM CD33 + CD13 | 0.01 nM CD33 + CD13 | 0.1 nM CD33 + CD13 | 1 nM CD33 + CD13 | 10 nM CD33 + CD13 | 100 nM CD33 + CD13 | 1000 nM CD33 + CD13 |
| B | Blank | Control | Negative Control | Positive Control 0.1 nM (CD33 + CD13) | 0.0001 nM CD33 + CD13 | 0.001 nM CD33 + CD13 | 0.01 nM CD33 + CD13 | 0.1 nM CD33 + CD13 | 1 nM CD33 + CD13 | 10 nM CD33 + CD13 | 100 nM CD33 + CD13 | 1000 nM CD33 + CD13 |
| C | Blank | Control | Negative Control | Positive Control 0.1 nM (CD33 + CD13) | 0.0001 nM CD33 + CD13 | 0.001 nM CD33 + CD13 | 0.01 nM CD33 + CD13 | 0.1 nM CD33 + CD13 | 1 nM CD33 + CD13 | 10 nM CD33 + CD13 | 100 nM CD33 + CD13 | 1000 nM CD33 + CD13 |
| D | | | | | | | | | | | | |
| E | | | | | | | | | | | | |
| F | | | | | | | | | | | | |
| G | | | | | | | | | | | | |
| H | | | | | | | | | | | | |

Table 5 shows the plate layout for the Kasumi-3 Cell Line treated with Anti-CD33+Anti-CD13 combination in presence of αMFc-CL-MMAE.

| BLANK | CONTROL | NEGATIVE CONTROL | POSITIVE CONTROL (CD33 0.1 nM) |
|---|---|---|---|
| 643.00 | 3,912,000.00 | 3,960,000.00 | 3,830,000.00 |
| 686.00 | 4,175,000.00 | 4,037,000.00 | 3,626,000.00 |
| 603.00 | 4,079,000.00 | 4,269,000.00 | 3,345,000.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 3,894,000.00 | 3,882,000.00 | 3,723,000.00 | 3,585,000.00 | 3,634,000.00 | 2,957,000.00 | 2,253,000.00 | 182,900.00 |
| 4,058,000.00 | 3,847,000.00 | 3,740,000.00 | 3,599,000.00 | 3,355,000.00 | 3,007,000.00 | 2,386,000.00 | 200,300.00 |
| 3,841,000.00 | 3,738,000.00 | 3,685,000.00 | 3,787,000.00 | 1,574,000.00 | 2,817,000.00 | 2,315,000.00 | 189,800.00 |

Table 6 shows the results from raw data for cytotoxicity profile of Anti-CD33 antibody in presence of αMFc-CL-MMAE to Kasumi-3.

| CONTROL | NEGATIVE CONTROL | POSITIVE CONTROL (CD33 0.1 nM) |
|---|---|---|
| 3,911,356.00 | 3,959,356.00 | 3,829,356.00 |
| 4,174,356.00 | 4,036,356.00 | 3,625,356.00 |
| 4,078,356.00 | 4,268,356.00 | 3,344,356.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 3,893,356.00 | 3,881,356.00 | 3,722,356.00 | 3,584,356.00 | 3,633,356.00 | 2,956,356.00 | 2,252,356.00 | 182,256.00 |
| 4,057,356.00 | 3,846,356.00 | 3,739,356.00 | 3,598,356.00 | 3,354,356.00 | 3,006,356.00 | 2,385,356.00 | 199,656.00 |
| 3,840,356.00 | 3,737,356.00 | 3,684,356.00 | 3,786,356.00 | 3,573,356.00 | 2,816,356.00 | 2,314,356.00 | 189,156.00 |

Table 7 shows the data after blank subtraction for cytotoxicity profile of Anti-CD33 antibody in presence of αMFc-CL-MMAE to Kasumi-3.

| CONTROL | NEGATIVE CONTROL | POSITIVE CONTROL (CD33 0.1 nM) |
|---|---|---|
| 100.00 | 101.23 | 97.90 |
| 100.00 | 96.69 | 86.85 |
| 100.00 | 104.66 | 82.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 99.54 | 99.23 | 95.17 | 91.64 | 92.89 | 75.58 | 57.59 | 4.66 |
| 97.20 | 92.14 | 89.58 | 86.20 | 80.36 | 72.02 | 57.14 | 4.78 |
| 94.16 | 91.64 | 90.34 | 92.84 | 87.62 | 69.06 | 56.75 | 4.64 |

Table 8 shows the percentage of Kasumi-3 viability with Anti-CD33 antibody in presence of αMFc-CL-MMAE treatment.

| BLANK | CONTROL | NEGATIVE CONTROL | POSITIVE CONTROL (CD7 0.1 nM) |
|---|---|---|---|
| 463.00 | 1,904,000.00 | 2,064,000.00 | 2,249,000.00 |
| 440.00 | 1,954,000.00 | 2,271,000.00 | 2,291,000.00 |
| 446.00 | 1,980,000.00 | 2,167,000.00 | 1,979,000.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 2,042,000.00 | 2,103,000.00 | 1,839,000.00 | 1,869,000.00 | 1,771,000.00 | 1,541,000.00 | 1,099,000.00 | 49,020.00 |
| 2,091,000.00 | 1,962,000.00 | 1,866,000.00 | 1,833,000.00 | 1,859,000.00 | 1,433,000.00 | 1,184,000.00 | 54,210.00 |
| 2,163,000.00 | 2,140,000.00 | 1,996,000.00 | 1,885,000.00 | 1,735,000.00 | 1,580,000.00 | 1,184,000.00 | 48,320.00 |

Table 9 shows the raw data for cytotoxicity profile of Anti-CD7 antibody in presence of αMFc-CL-MMAE to Kasumi-3.

| CONTROL | NEGATIVE CONTROL | POSITIVE CONTROL (CD7 0.1 nM) |
|---|---|---|
| 1,903,550.33 | 2,063,550.33 | 2,248,550.33 |
| 1,953,550.33 | 2,270,550.33 | 2,290,550.33 |
| 1,979,550.33 | 2,166,550.33 | 1,978,550.33 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 2,041,550.33 | 2,102,550.33 | 1,838,550.33 | 1,868,550.33 | 1,770,550.33 | 1,540,550.33 | 1,098,550.33 | 48,570.33 |
| 2,090,550.33 | 1,961,550.33 | 1,865,550.33 | 1,832,550.33 | 1,858,550.33 | 1,432,550.33 | 1,183,550.33 | 53,760.33 |
| 2,162,550.33 | 2,139,550.33 | 1,995,550.33 | 1,884,550.33 | 1,734,550.33 | 1,579,550.33 | 1,183,550.33 | 47,870.33 |

Table 10 shows the data after blank subtraction for cytotoxicity profile of Anti-CD7 antibody in presence of αMFc-CL-MMAE to Kasumi-3.

| CONTROL | NEGATIVE CONTROL | POSITIVE CONTROL (CD7 0.1 nM) |
|---|---|---|
| 100.00 | 108.41 | 118.12 |
| 100.00 | 116.23 | 117.25 |
| 100.00 | 109.45 | 99.95 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 107.25 | 110.45 | 96.59 | 98.16 | 93.01 | 80.93 | 57.71 | 2.55 |
| 107.01 | 100.41 | 95.50 | 93.81 | 95.14 | 73.33 | 60.58 | 2.75 |
| 109.24 | 108.08 | 100.81 | 95.20 | 87.62 | 79.79 | 59.79 | 2.42 |

Table 11 shows the percentage of Kasumi-3 viability with Anti-CD7 antibody in presence of αMFc-CL-MMAE treatment.

| BLANK | CONTROL | NEGATIVE CONTROL | POSITIVE CONTROL (CD13 0.1 nM) |
|---|---|---|---|
| 543.00 | 3,835,000.00 | 3,710,000.00 | 2,534,000.00 |
| 633.00 | 3,844,000.00 | 3,579,000.00 | 2,830,000.00 |
| 570.00 | 3,677,000.00 | 3,556,000.00 | 2,459,000.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 3,142,000.00 | 2,952,000.00 | 2,755,000.00 | 2,437,000.00 | 2,478,000.00 | 1,657.000.00 | 1,542,000.00 | 978,600.00 |
| 3,163,000.00 | 3,326,000.00 | 2,791,000.00 | 2,539,000.00 | 2,533,000.00 | 1,566,000.00 | 1,610,000.00 | 1,070,000.00 |
| 3,100,000.00 | 3,470,000.00 | 3,043,000.00 | 2,658,000.00 | 2,564,000.00 | 1,909,000.00 | 1,637,000.00 | 1,051,000.00 |

Table 12 shows raw data for cytotoxicity profile of Anti-CD13 antibody in presence of αMFc-CL-MMAE to Kasumi-3.

| CONTROL | NEGATIVE CONTROL | POSITIVE CONTROL (CD13 0.1 nM) |
|---|---|---|
| 3,834,418.00 | 3,709,418.00 | 2,533,418.00 |
| 3,843,418.00 | 3,578,418.00 | 2,829,418.00 |
| 3,676,418.00 | 3,555,418.00 | 2,458,418.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 3,141,418.00 | 2,951,418.00 | 2,754,418.00 | 2,436,418.00 | 2,477,418.00 | 1,656,418.00 | 1,541,418.00 | 978,018.00 |
| 3,162,418.00 | 3,325,418.00 | 2,790,418.00 | 2,538,418.00 | 2,532,418.00 | 1,565,418.00 | 1,609,418.00 | 1,069,418.00 |
| 3,099,418.00 | 3,469,418.00 | 3,042,418.00 | 2,657,418.00 | 2,563,418.00 | 1,908,418.00 | 1,636,418.00 | 1,050,418.00 |

Table 13 shows the data after blank subtraction for cytotoxicity profile of Anti-CD13 antibody in presence of αMFc-CL-MMAE to Kasumi-3.

| CONTROL | NEGATIVE CONTROL | POSITIVE CONTROL (CD13 0.1 nM) |
|---|---|---|
| 100.00 | 96.74 | 66.07 |
| 100.00 | 93.11 | 73.62 |
| 100.00 | 96.71 | 66.87 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 81.93 | 76.97 | 71.83 | 63.54 | 64.61 | 43.20 | 40.20 | 25.51 |
| 82.28 | 86.52 | 72.60 | 66.05 | 65.89 | 40.73 | 41.87 | 27.82 |
| 84.31 | 94.37 | 82.75 | 72.28 | 69.73 | 51.91 | 44.51 | 28.57 |

Table 14 shows the percentage of Kasumi-3 viability with Anti-CD13 antibody in presence of αMFc-CL-MMAE treatment.

| BLANK | CONTROL | NEGATIVE CONTROL | POSITIVE CONTROL (CD33 + CD7 0.1 nM) |
|---|---|---|---|
| 393.00 | 2,487,000.00 | 2,446,000.00 | 2,617,000.00 |
| 473.00 | 2,429,000.00 | 2,418,000.00 | 2,601,000.00 |
| 370.00 | 2,578,000.00 | 2,434,000.00 | 2,462,000.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 2,567,000.00 | 2,628,000.00 | 2,486,000.00 | 2,480,000.00 | 2,362,000.00 | 1,179,000.00 | 892,600.00 | 1,020.00 |
| 2,588,000.00 | 2,564,000.00 | 2,464,000.00 | 2,466,000.00 | 2,224,000.00 | 1,207,000.00 | 913,900.00 | 1,056.00 |
| 2,590,000.00 | 2,420,000.00 | 2,522,000.00 | 2,456,000.00 | 2,286,000.00 | 1,202,000.00 | 900,500.001 | 1,026.00 |

Table 15 shows the raw data for cytotoxicity profile of Anti-CD33+Anti-CD7 antibodies in presence of αMFc-CL-MMAE to Kasumi-3.

| CONTROL | NEGATIVE CONTROL | POSITIVE CONTROL (CD33 + CD7 0.1 nM) |
|---|---|---|
| 2,486,588.00 | 2,445,588.00 | 2,616,588.00 |
| 2,428,588.00 | 2,417,588.00 | 2,600,588.00 |
| 2,577,588.00 | 2,433,588.00 | 2,461,588.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 2,566,588.00 | 2,627,588.00 | 2,485,588.00 | 2,479,588.00 | 2,361,588.00 | 1,178,588.00 | 892,188.00 | 608.00 |
| 2,587,588.00 | 2,563,588.00 | 2,463,588.00 | 2,465,588.00 | 2,223,588.00 | 1,206,588.00 | 913,488.00 | 644.00 |
| 2,589,588.00 | 2,419,588.00 | 2,521,588.00 | 2,455,588.00 | 2,285,588.00 | 1,201,588.00 | 900,088.00 | 614.00 |

Table 16 shows the data after blank subtraction for cytotoxicity profile of Anti-CD33+Anti-CD7 antibodies in presence of αMFc-CL-MMAE to Kasumi-3.

| CONTROL | NEGATIVE CONTROL | POSITIVE CONTROL (CD33 + CD7 0.1 nM) |
|---|---|---|
| 100.00 | 98.35 | 105.23 |
| 100.00 | 99.55 | 107.08 |
| 100.00 | 94.41 | 95.50 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 103.22 | 105.67 | 99.96 | 99.72 | 94.97 | 47.40 | 35.88 | 0.02 |
| 106.55 | 105.56 | 101.44 | 101.52 | 91.56 | 49.68 | 37.61 | 0.03 |
| 100.47 | 93.87 | 97.83 | 95.27 | 88.67 | 46.62 | 34.92 | 0.02 |

Table 17 shows the percentage of Kasumi-3 viability with Anti-CD33+Anti-CD7 antibodies in presence of αMFc-CL-MMAE treatment.

| BLANK | CONTROL | NEGATIVE CONTROL | POSITIVE CONTROL (CD33 + CD13 0.1 nM) |
|---|---|---|---|
| 346.00 | 1,398,000.00 | 1,283,000.00 | 1,105,000.00 |
| 373.00 | 1,395,000.00 | 1,383,000.00 | 1,104,000.00 |
| 376.00 | 1,346,000.00 | 1,380,000.00 | 1,055,000.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 1,196,000.00 | 1,168,000.00 | 1,095,000.00 | 1,099,000.00 | 872,300.00 | 768,900.00 | 735,900.00 | 234,000.00 |
| 1,248,000.00 | 1,194,000.00 | 1,078,000.00 | 1,086,000.00 | 880,600.00 | 803,900.00 | 744,100.00 | 209,000.00 |
| 1,249,000.00 | 1,141,000.00 | 1,107,000.00 | 1,011,000.00 | 844,700.00 | 792,200.00 | 735,500.00 | 218,100.00 |

Table 18 shows the raw data for cytotoxicity profile of Anti-CD33+Anti-CD13 antibodies in presence of αMFc-CL-MMAE to Kasumi-3.

| CONTROL | NEGATIVE CONTROL | POSITIVE CONTROL (CD33 + CD13 0.1 nM) |
|---|---|---|
| 1,397,635.00 | 1,282,635.00 | 1,104,635.00 |
| 1,394,635.00 | 1,382,635.00 | 1,103,635.00 |
| 1,345,635.00 | 1,379,635.00 | 1,054,635.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 1,195,635.00 | 1,167,635.00 | 1,094,635.00 | 1,098,635.00 | 871,935.00 | 768,535.00 | 735,535.00 | 233,635.00 |
| 1,247,635.00 | 1,193,635.00 | 1,077,635.00 | 1,085,635.00 | 880,235.00 | 803,535.00 | 743,735.00 | 208,635.00 |
| 1,248,635.00 | 1,142,635.00 | 1,106,635.00 | 1,010,635.00 | 844,335.00 | 791,835.00 | 735,135.00 | 217,735.00 |

Table 19 shows the data after blank subtraction for cytotoxicity profile of Anti-CD33+Anti-CD13 antibodies in presence of αMFc-CL-MMAE to Kasumi-3.

| CONTROL | NEGATIVE CONTROL | POSITIVE CONTROL (CD33 + CD13 0.1 nM) |
|---|---|---|
| 100.00 | 91.77 | 79.04 |
| 100.00 | 99.14 | 79.13 |
| 100.00 | 102.53 | 78.37 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 85.55 | 83.54 | 78.32 | 78.61 | 62.39 | 54.99 | 52.63 | 16.72 |
| 89.46 | 85.59 | 77.27 | 77.84 | 63.12 | 57.62 | 53.33 | 14.96 |
| 92.79 | 84.77 | 82.24 | 75.10 | 62.75 | 58.84 | 54.63 | 16.18 |

Table 20 shows the percentage of Kasumi-3 viability with Anti-CD33+Anti-CD13 antibodies in presence of αMFc-CL-MMAE treatment.

| | 1 | 2 | 3 | 4 | 5 | 6 | 7 | 8 | 9 | 10 | 11 | 12 |
|---|---|---|---|---|---|---|---|---|---|---|---|---|
| A | Blank | Control | Negative Control | Positive Control 0.1 nM (CD33) | 0.0001 nM CD33 | 0.001 nM CD33 | 0.01 nM CD33 | 0.1 nM CD33 | 1 nM CD33 | 10 nM CD33 | 100 nM CD33 | 1000 nM CD33 |
| B | Blank | Control | Negative Control | Positive Control 0.1 nM (CD33) | 0.0001 nM CD33 | 0.001 nM CD33 | 0.01 nM CD33 | 0.1 nM CD33 | 1 nM CD33 | 10 nM CD33 | 100 nM CD33 | 1000 nM CD33 |
| C | Blank | Control | Negative Control | Positive Control 0.1 nM (CD33) | 0.0001 nM CD33 | 0.001 nM CD33 | 0.01 nM CD33 | 0.1 nM CD33 | 1 nM CD33 | 10 nM CD33 | 100 nM CD33 | 1000 nM CD33 |
| D | | | | | | | | | | | | |
| E | | | | | | | | | | | | |
| F | | | | | | | | | | | | |
| G | | | | | | | | | | | | |
| H | | | | | | | | | | | | |

Table 21 shows the plate layout for the HEL 92.1.7 Cell Line treated with Anti-CD33 in presence of αMFc-CL-MMAE.

| | 1 | 2 | 3 | 4 | 5 | 6 | 7 | 8 | 9 | 10 | 11 | 12 |
|---|---|---|---|---|---|---|---|---|---|---|---|---|
| A | Blank | Control | Negative Control | Positive Control 0.1 nM (CD56) | 0.0001 nM CD56 | 0.001 nM CD56 | 0.01 nM CD56 | 0.1 nM CD56 | 1 nM CD56 | 10 nM CD56 | 100 nM CD56 | 1000 nM CD56 |
| B | Blank | Control | Negative Control | Positive Control 0.1 nM (CD56) | 0.0001 nM CD56 | 0.001 nM CD56 | 0.01 nM CD56 | 0.1 nM CD56 | 1 nM CD56 | 10 nM CD56 | 100 nM CD56 | 1000 nM CD56 |
| C | Blank | Control | Negative Control | Positive Control 0.1 nM (CD56) | 0.0001 nM CD56 | 0.001 nM CD56 | 0.01 nM CD56 | 0.1 nM CD56 | 1 nM CD56 | 10 nM CD56 | 100 nM CD56 | 1000 nM CD56 |
| D | | | | | | | | | | | | |
| E | | | | | | | | | | | | |
| F | | | | | | | | | | | | |
| G | | | | | | | | | | | | |
| H | | | | | | | | | | | | |

Table 22 shows the plate layout for the HEL 92.1.7 Cell Line treated with Anti-CD56 in presence of αMFc-CL-MMAE.

| | 1 | 2 | 3 | 4 | 5 | 6 | 7 | 8 | 9 | 10 | 11 | 12 |
|---|---|---|---|---|---|---|---|---|---|---|---|---|
| A | Blank | Control | Negative Control | Positive Control 0.1 nM (CD33 + CD56) | 0.0001 nM CD33 + CD56 | 0.001 nM CD33 + CD56 | 0.01 nM CD33 + CD56 | 0.1 nM CD33 + CD56 | 1 nM CD33 + CD56 | 10 nM CD33 + CD56 | 100 nM CD33 + CD56 | 1000 nM CD33 + CD56 |
| B | Blank | Control | Negative Control | Positive Control 0.1 nM (CD33 + CD56) | 0.0001 nM CD33 + CD56 | 0.001 nM CD33 + CD56 | 0.01 nM CD33 + CD56 | 0.1 nM CD33 + CD56 | 1 nM CD33 + CD56 | 10 nM CD33 + CD56 | 100 nM CD33 + CD56 | 1000 nM CD33 + CD56 |
| C | Blank | Control | Negative Control | Positive Control 0.1 nM (CD33 + CD56) | 0.0001 nM CD33 + CD56 | 0.001 nM CD33 + CD56 | 0.01 nM CD33 + CD56 | 0.1 nM CD33 + CD56 | 1 nM CD33 + CD56 | 10 nM CD33 + CD56 | 100 nM CD33 + CD56 | 1000 nM CD33 + CD56 |
| D | | | | | | | | | | | | |
| E | | | | | | | | | | | | |
| F | | | | | | | | | | | | |
| G | | | | | | | | | | | | |
| H | | | | | | | | | | | | |

Table 23 shows the plate layout for the HEL 92.1.7 Cell Line treated with Anti-CD33+Anti-CD56 combination in presence of αMFc-CL-MMAE.

| BLANK | CONTROL | NEGATIVE CONTROL | POSITIVE CONTROL (CD33 0.1 nM) |
|---|---|---|---|
| 1,456.00 | 12,140,000.00 | 10,750,000.00 | 13,190,000.00 |
| 1,370.00 | 12,980,000.00 | 12,470,000.00 | 13,340,000.00 |
| 1,703.00 | 12,500,000.00 | 12,390,000.00 | 11,370,000.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 11,290,000.00 | 11,390,000.00 | 11,610,000.00 | 10,570,000.00 | 10,460,000.00 | 10,520,000.00 | 9,096,000.00 | 3,746,000.00 |
| 23,140,000.00 | 12,420,000.00 | 12,250,000.00 | 12,140,000.00 | 11,770,000.00 | 10,550,000.00 | 10,660,000.00 | 3,685,000.00 |
| 11,250,000.00 | 12,740,000.00 | 11,940,000.00 | 11,910,000.00 | 11,590,000.00 | 10,980,000.00 | 10,820,000.00 | 3,568,000.00 |

Table 24 shows the raw data for cytotoxicity profile of Anti-CD33 antibody in presence of αMFc-CL-MMAE to HEL 92.1.7.

| CONTROL | NEGATIVE CONTROL | POSITIVE CONTROL (CD33 0.1 nM) |
|---|---|---|
| 12,138,490.33 | 10,798,490.33 | 13,188,490.33 |
| 12,978,490.33 | 12,468,490.33 | 13,338,490.33 |
| 12,498,490.33 | 12,388,490.33 | 11,368,490.33 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 11,288,490.33 | 11388490.33 | 11608490.33 | 105684490.33 | 10458490.33 | 10518490.33 | 9094490.333 | 3744490.333 |
| 12,138,490.33 | 12418490.33 | 12248490.33 | 121384490.33 | 11768490.33 | 10548490.33 | 10658490.33 | 3683490.333 |
| 11,248,490.33 | 12738490.33 | 11938490.33 | 119084490.33 | 11588490.33 | 10978490.33 | 10818490.33 | 3566490.333 |

Table 25 shows the data after blank subtraction for cytotoxicity profile of Anti-CD33 antibody in presence of αMFc-CL-MMAE to HEL 92.1.7.

| CONTROL | NEGATIVE CONTROL | POSITIVE CONTROL (CD33 0.1 nM) |
|---|---|---|
| 100.00 | 88.55 | 108.65 |
| 100.00 | 96.07 | 102.77 |
| 100.00 | 99.12 | 90.96 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 93.00 | 93.82 | 95.63 | 87.07 | 86.16 | 86.65 | 74.92 | 30.85 |
| 93.56 | 95.69 | 94.38 | 93.53 | 90.68 | 81.28 | 82.12 | 28.38 |
| 90.00 | 101.92 | 95.52 | 95.28 | 92.72 | 87.84 | 86.56 | 28.54 |

Table 26 shows the percentage of HEL 92.1.7 viability with Anti-CD33 antibody in presence of αMFc-CL-MMAE treatment.

| BLANK | | CONTROL | | NEGATIVE CONTROL | | POSITIVE CONTROL (CD56 0.1 nM) | |
|---|---|---|---|---|---|---|---|
| 1,386.00 | | 12,830,000.00 | | 12,290,000.00 | | 12,040,000.00 | |
| 1,636.00 | | 13,410,000.00 | | 12,610,000.00 | | 12,360,000.00 | |
| 1,363.00 | | 12,040,000.00 | | 12,380,000.00 | | 11,710,000.00 | |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 11,880,000.00 | 12,450,000.00 | 12,130,000.00 | 11,570,000.00 | 10,910,000.00 | 7,583,000.00 | 1,293,000.00 | 82,150.00 |
| 13,570,000.00 | 12,550,000.00 | 13,180,000.00 | 11,680,000.00 | 10,350,000.00 | 8,122,000.00 | 1,252,000.00 | 85,990.00 |
| 13,450,000.00 | 12,330,000.00 | 13,570,000.00 | 11,700,000.00 | 10,210,000.00 | 7,849,000.00 | 1,132,000.00 | 115,200.00 |

Table 27 shows the raw data for cytotoxicity profile of Anti-CD56 antibody in presence of αMFc-CL-MMAE to HEL 92.1.7.

| CONTROL | NEGATIVE CONTROL | POSITIVE CONTROL (CD56 0.1 nM) |
|---|---|---|
| 12,828,538.33 | 12,288,538.33 | 12,038,538.33 |
| 13,408,538.33 | 12,608,538.33 | 12,358,538.33 |
| 12,038,538.33 | 12,378,538.33 | 11,707,538.33 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 11878538.33 | 12448538.33 | 12128538.33 | 11568538.33 | 10908538.33 | 7581538.333 | 1291538.333 | 80688.33333 |
| 13568538.33 | 12548538.33 | 13178538.33 | 11678538.33 | 10348538.33 | 8120538.333 | 1250538.333 | 84528.33333 |
| 13448538.33 | 12328538.33 | 13568538.33 | 11698538.33 | 10208538.33 | 7847538.333 | 1130538.333 | 113738.3333 |

Table 28 shows the data after blank subtraction for cytotoxicity profile of Anti-CD56 antibody in presence of αMFc-CL-MMAE to HEL 92.1.7.

| CONTROL | NEGATIVE CONTROL | POSITIVE CONTROL (CD56 0.1 nM) |
|---|---|---|
| 100.00 | 95.79 | 93.84 |
| 100.00 | 94.03 | 92.17 |
| 100.00 | 102.82 | 97.26 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 92.59 | 97.01 | 94.54 | 90.18 | 85.03 | 59.10 | 10.07 | 0.63 |
| 101.19 | 93.59 | 98.28 | 87.10 | 77.18 | 60.56 | 9.33 | 0.63 |
| 111.71 | 102.41 | 112.71 | 97.18 | 84.80 | 65.19 | 9.39 | 0.94 |

Table 29 shows the percentage of HEL 92.1.7 viability with Anti-CD56 antibody in presence of αMFc-CL-MMAE treatment.

| BLANK | CONTROL | NEGATIVE CONTROL | POSITIVE CONTROL (CD33 + CD56 0.1 nM) |
|---|---|---|---|
| 450.00 | 4293000.00 | 4051000.00 | 4712000.00 |
| 576.00 | 4854000.00 | 4466000.00 | 5028000.00 |
| 456.00 | 3824000.00 | 3947000.00 | 4126000.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 4057000.00 | 4550000.00 | 4114000.00 | 3270000.00 | 3108000.00 | 2627000.00 | 3939000.00 | 7085.00 |
| 4100000.00 | 4586000.00 | 4267000.00 | 4025000.00 | 3084000.00 | 2622000.00 | 4065000.00 | 2943.00 |
| 4088000.00 | 4173000.00 | 4157000.00 | 3711000.00 | 3229000.00 | 2684000.00 | 3916000.00 | 2963.00 |

Table 30 shows the raw data for cytotoxicity profile of Anti-CD33+Anti-CD56 antibodies in presence of αMFc-CL-MMAE to HEL 92.1.7.

| CONTROL | NEGATIVE CONTROL | POSITIVE CONTROL (CD33 + CD56 0.1 nM) |
|---|---|---|
| 4292506.00 | 4050506.00 | 4711506.00 |
| 4853506.00 | 4465506.00 | 5027506.00 |
| 3823506.00 | 3945506.00 | 4125506.00 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 4056506.00 | 4549506.00 | 4113506.00 | 3269506.00 | 3107506.00 | 2626506.00 | 393406.00 | 6591.00 |
| 4099506.00 | 4585506.00 | 4266506.00 | 4024506.00 | 3083506.00 | 2621506.00 | 406006.00 | 2449.00 |
| 4087506.00 | 4172506.00 | 4156506.00 | 3710506.00 | 3228506.00 | 2683506.00 | 391106.00 | 2469.00 |

Table 31 shows the data after blank subtraction for cytotoxicity profile of Anti-CD33+Anti-CD56 antibodies in presence of αMFc-CL-MMAE to HEL 92.1.7.

| CONTROL | NEGATIVE CONTROL | POSITIVE CONTROL (CD33 + CD56 0.1 nM) |
|---|---|---|
| 100.00 | 94.36 | 109.76 |
| 100.00 | 92.01 | 103.59 |
| 100.00 | 103.22 | 107.90 |

| 0.0001 nM TEST | 0.001 nM TEST | 0.01 nM TEST | 0.1 nM TEST | 1 nM TEST | 10 nM TEST | 100 nM TEST | 1000 nM TEST |
|---|---|---|---|---|---|---|---|
| 94.50 | 105.99 | 95.83 | 76.17 | 72.39 | 61.19 | 9.16 | 0.15 |
| 84.46 | 94.48 | 87.91 | 82.92 | 63.53 | 54.01 | 8.37 | 0.05 |
| 106.90 | 109.13 | 108.71 | 97.04 | 84.44 | 70.18 | 10.23 | 0.06 |

Table 32 shows the percentage of HEL 92.1.7 viability with Anti-CD33+Anti-CD56 antibodies in presence of αMFc-CL-MMAE treatment.

The invention claimed is:

1. A method of treating a CD7+CD33+ hematological malignancy by administering a cell inhibiting agent that bispecifically binds to CD33 and CD7, wherein said cell inhibiting agent comprises a cytotoxin linked to a bispecific antibody or antigen binding portion thereof, including a CD7 binding portion and a CD33 binding portion.

2. The method of treating the CD7+CD33+ hematological malignancy according to claim 1, wherein said cell inhibiting agent is capable of inducing a CD33 and/or CD7 receptor mediated internalization of said cell inhibiting agent into a CD33+ and CD7+ cell.

3. The method of treating the CD7+CD33+ hematological malignancy according to claim 2, wherein the CD33+ and CD7+ cell is an AML cell.

4. The method of treating the CD7+CD33+ hematological malignancy according to claim 1, wherein said CD33 binding portion comprises an antigen binding fragment of an antibody.

5. The method of treating the CD7+CD33+ hematological malignancy according to claim 1, wherein said CD7 binding portion comprises an antigen binding fragment of an antibody.

6. The method of treating the CD7+CD33+ hematological malignancy according to claim 1, wherein said cell inhibiting agent further comprises a linking portion.

7. The method of treating the CD7+CD33+ hematological malignancy according to claim 1, wherein said cytotoxin is selected from: i) a peptide toxin or ii) a chemical toxin.

8. The method of treating the CD7+CD33+ hematological malignancy according to claim 1, wherein the cytotoxin is an auristatin.

9. The method of treating the CD7+CD33+ hematological malignancy according to claim 8, wherein the auristatin is auristatin E, monomethylauristatin E, or monomethylauristatin F.

* * * * *